United States Patent
Otten et al.

(10) Patent No.: US 6,291,682 B1
(45) Date of Patent: *Sep. 18, 2001

(54) PYRAZOL-4-YLBENZOYL DERIVATIVES AND THEIR USE AS HERBICIDES

(75) Inventors: Martina Otten, Ludwigshafen; Wolfgang von Deyn, Neustadt; Stefan Engel, Idstein; Regina Luise Hill, Speyer; Uwe Kardorff; Marcus Vossen, both of Mannheim; Peter Plath, Frankenthal; Norbert Götz, Worms; Helmut Walter, Obrigheim; Karl-Otto Westphalen, Speyer; Ulf Misslitz, Neustadt, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,124
(22) PCT Filed: Aug. 29, 1996
(86) PCT No.: PCT/EP96/03794
  § 371 Date: Feb. 24, 1998
  § 102(e) Date: Feb. 24, 1998
(87) PCT Pub. No.: WO97/09327
  PCT Pub. Date: Mar. 13, 1997

(30) Foreign Application Priority Data

Sep. 1, 1995 (DE) .............................. 195 32 312

(51) Int. Cl.[7] ..................... C07D 409/06; C07D 335/06; A01N 43/56; A01N 43/50
(52) U.S. Cl. .................. 548/364.4; 504/280; 548/252
(58) Field of Search ............. 504/280; 548/282, 548/364.4, 311.4, 333.15, 316.4, 320.1

(56) References Cited

U.S. PATENT DOCUMENTS 5,468,722 * 11/1995 Shibata et al. .................. 504/282
5,506,194 * 4/1996 Nasuno et al. .................. 504/282
5,607,898 * 3/1997 Nakamura et al. ............... 504/282

FOREIGN PATENT DOCUMENTS

93/18031 * 9/1993 (WO) ........................... 504/282
94/01431 * 1/1994 (WO) ........................... 504/282

* cited by examiner

Primary Examiner—Floyd D. Higel
(74) Attorney, Agent, or Firm—Keil & Weinkauf

(57) ABSTRACT

Pyrazol-4-ylbenzoyl derivatives

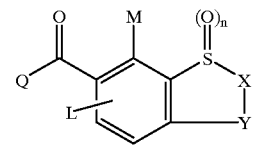

I where the substituents L, M, X, Y and n have the meanings given in claim 1 and Q is a pyrazole ring, linked in the 4-position, of the formula II

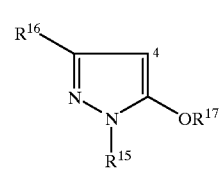

II where $R^{15}$ is $C_1$–$C_4$-alkyl, $R^{16}$ is hydrogen, $C_1$–$C_4$-alkyl or $C_1$–$C_4$-haloalkyl and $R^{17}$ is hydrogen, $C_1$–$C_4$-alkylsulfonyl, phenylsulfonyl or alkylphenylsulfonyl, where, in the event that Y=C=O, X is other than $NR^{23}$, agriculturally useful salts, a process for their preparation, and their use as herbicides.

18 Claims, No Drawings

PYRAZOL-4-YLBENZOYL DERIVATIVES AND THEIR USE AS HERBICIDES

The present invention relates to novel herbicidally active pyrazol-4-ylbenzoyl derivatives, to processes for the preparation of the pyrazol-4-ylbenzoyl derivatives, to compositions which comprise them, and to the use of these derivatives or of the compositions comprising them for controlling weeds.

Herbicidally active pyrazolebenzoyl derivatives have been disclosed in the literature, for example in EP 352543, WO 93/15060, WO 94/01431 and WO 93/18031.

However, the herbicidal properties of the known compounds and the compatibility with crop plants are only moderately satisfactory.

It was an object of the present invention to find novel pyrazolebenzoyl derivatives which have improved properties.

We have found that this object is achieved by pyrazol-4-ylbenzoyl derivatives of the formula I

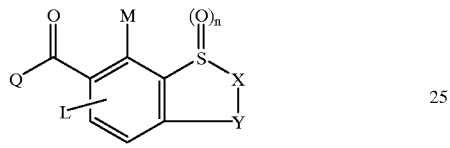

where the substituents have the following meanings:

L,M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro, a group —$(A)_m$—$S(O)_n R^1$ or a group —$(A)_m$—CO—$R^2$;

Y is a group consisting of C=O, C=N—$R^3$, $CR^7$—$NR^5R^6$, $CR^7$—$OR^8$, $CR^{10}R^{11}$, $CR^7$—$SR^8$; 1,3-dioxanyl or 1,3-dioxolanyl, each of which is substituted by hydrogen or $C_1$–$C_4$-alkyl; a hetero atom selected from the group consisting of oxygen, sulfur and nitrogen;

X is a chain (—$CR^{12}R^{13}$—), (—$CR^{12}R^{13}$—$CR^{21}R^{22}$—), (—$CR^{12}$=$CR^{13}$—), (—$CR^{12}R^{13}$—$CR^{12}$=$CR^{13}$—); $NR^{23}$;

the bond between X and Y can be saturated or unsaturated;

A is oxygen or $NR^{14}$;

m is zero or one;

n is zero, one or two;

$R^1$ is $C_1$–$C_4$-alkyl, $C_1$–$C_4$-haloalkyl or $NR^{14}$;

$R^2$ is $C_1$–$C_4$ alkyl, $C_1$–$C_4$-haloalkyl, $C_1$–$C_4$-alkoxy or $NR^{14}$;

$R^3$ is hydrogen, —$NR^9R^4$; $C_1$–$C_6$-alkyl, $C_1$–$C_6$-haloalkyl, $C_1$–$C_6$-alkoxy, $C_1$–$C_6$-haloalkoxy, $C_2$–$C_6$-alkenyl, $C_2$–$C_6$-haloalkenyl, $C_2$–$C_6$-alkynyl;
    mono- to polysubstituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro; mono- to polysubstituted benzyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;
    mono- to polysubstituted benzyloxy, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^4$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;
    mono- to polysubstituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;
    mono- to polysubstituted benzyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^9$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;
    mono- to polysubstituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;
    mono- to polysubstituted benzyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^5,R^6$ independently of one another are hydrogen, $C_1$–$C_6$-alkyl, $C_2$–$C_6$-alkenyl, $C_1$–$C_4$ haloalkyl, $C_2$–$C_6$ haloalkenyl, $C_1$–$C_6$-alkoxy, $C_1$–$C_6$-haloalkoxy;
    mono- to polysubstituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;
    mono- to polysubstituted benzyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^7$ is hydrogen, $C_1$–$C_6$-alkyl, $C_1$–$C_4$-alkoxy, $C_1$–$C_4$-haloalkyl, $C_1$–$C_4$-haloalkoxy; unsubstituted or substituted phenyl, it being possible for the substituents to be from the series consisting of one to three halogens, $C_1$–$C_4$-alkyl, $C_1$–$C_4$-alkoxy, $C_1$–$C_4$-haloalkoxy, nitro; $R^7$ and $R^{21}$ or $R^7$ and $R^{23}$ or $R^7$ and $R^{12}$ can form a bond;

$R^8$ is hydrogen, $C_1$–$C_6$ alkyl, $C_1$–$C_4$-haloalkyl, substituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;
    substituted benzyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{10},R^{11}$ independently of one another are hydrogen, $C_1$–$C_6$-alkyl; phenyl which is unsubstituted or substituted by one to three halogens, $C_1$–$C_4$-alkyl, $C_1$–$C_4$-alkoxy, $C_1$–$C_4$-haloalkoxy, nitro; $R^{10}$ and $R^{12}$ or $R^{10}$ and $R^{23}$ or $R^{10}$ and $R^{21}$ can form a bond;

$R^{12},R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy;
    unsubstituted or substituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{14}$ is $C_1$–$C_4$-alkyl;

$R^{21}$ is hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{22}$ is hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, it being possible for the substituents to be from the series consisting of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{23}$ is hydrogen, $C_1$–$C_6$-alkyl, $C_2$–$C_6$-alkenyl, $C_1$–$C_6$-alkoxy; phenyl or benzyl, each of which is unsubstituted or substituted by $C_1$–$C_4$-alkyl, $C_1$–$C_4$-alkoxy, $C_1$–$C_4$-haloalkoxy, $C_1$–$C_4$-haloalkyl, halogen, cyano, nitro;

Q is a pyrazole ring, linked in the 4-position, of the formula II

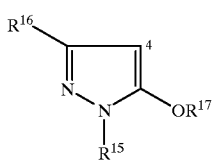

where $R^{15}$ is $C_1$–$C_4$-alkyl, $R^{16}$ is hydrogen, $C_1$–$C_4$-alkyl or $C_1$–$C_4$-haloalkyl and $R^{17}$ is hydrogen, $C_1$–$C_4$-alkylsulfonyl, phenylsulfonyl or alkylphenylsulfonyl, where, in the event that Y=C=O, X is other than $NR^{23}$, and agriculturally useful salts of the compound I.

Compounds of the formula I are obtained by reacting 5-hydroxypyrazoles of the formula IIa with a benzoic acid derivative of the formula III and subjecting the products to a rearrangement reaction to give pyrazol-4-ylbenzoyl derivatives of the formula I:

DIAGRAM 1

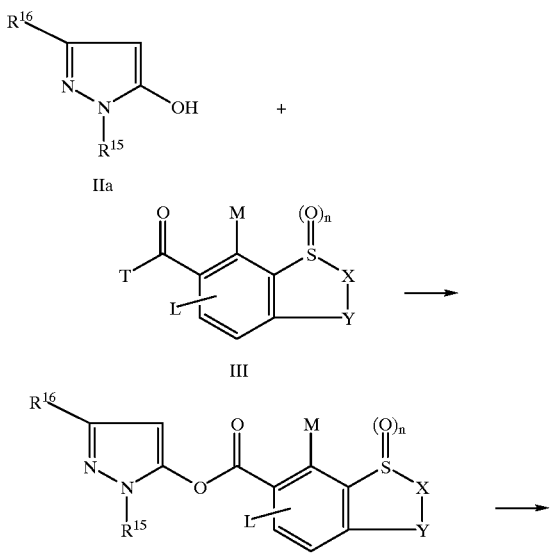

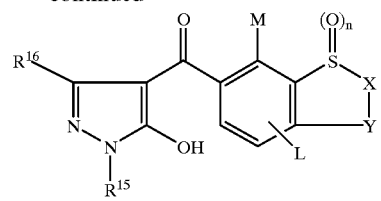

In the above diagram 1, T in the abovementioned formulae has the meanings of halogen or OH and $R^{15}$, $R^{16}$, L, M, X, Y and n have the abovementioned meanings.

The first step of the reaction sequence, ie. the acylation, is carried out in the generally known manner, for example by adding an acid chloride of the formula III (T=Cl) or a carboxylic acids III (T=OH) which has been activated using, for example, DCC (dicyclocarbodiimides) or similar agents known from the literature, eg. triphenylphosphine/DEAD=diethyl azodicarboxylate, 2-pyridine disulfide/triphenylphosphine, to the solution or suspension of a cyclohexanedione II, in the presence or absence of an auxiliary base. The reactants and the auxiliary base are expediently employed in equimolar amounts. Under certain circumstances, a slight excess, for example, 1.2 to 1.5 mol equivalents of the auxiliary base, based on II, may be advantageous.

Useful auxiliary bases are tertiary alkylamines, pyridine or alkali metal carbonates. Solvents which can be employed are, for example, methylene chloride, dioxane, diethyl ether, toluene, acetonitrile or ethyl acetate.

While the acid chloride is added, the reaction mixture is preferably cooled to 0 to 10° C., and it is then stirred at from 20 to 100° C., in particular 25 to 50° C., until the reaction has ended. Work-up is carried out in the customary manner, for example the reaction mixture is poured into water and the product of interest is extracted, for example using methylene chloride. After drying of the organic phase and removal of the solvent, the crude enol ester can be employed in the rearrangement reaction without further purification. Preparation examples of benzoic esters of 5-hydroxypyrazoles can be found, for example, [lacuna] EP-A-282 944 or U.S. Pat. No. 4,643,757.

The rearrangement of the 5-hydroxypyrazoylbenzoic [sic] esters to the compounds of the formula I is expediently carried out at from 20 to 40° C. in a solvent and in the presence of an auxiliary base and, if desired, with the aid of a cyano compound as catalyst.

Examples of solvents which can be used are acetonitrile, methylene chloride, tert-amyl alcohol, dioxane, 1,2-dichloroethane, ethyl acetate or toluene. Preferred solvents are acetonitrile and dioxane. Useful auxiliary bases are tertiary alkylamines, pyridine or alkali metal carbonates, and these are preferably employed in equimolar amounts or up to an excess of four times based on the 5-hydroxypyrazolebenzoic [sic] ester. Preferred auxiliary bases are triethylamine and alkali metal carbonate in twice the amount.

Useful catalysts are potassium cyanide, acetone cyanohydrin and trimethylsilyl cyanide, preferably in an amount of 1 to 50 mol percent based on the enol ester. It is preferred to add acetone cyanohydrin, for example in an amount of 5 to 15, in particular 10, mol percent.

Examples of the rearrangement of benzoic esters of 5-hydroxypyrazoles can be found, for example, in EP-A 282

944 or U.S. Pat. No. 4,643,757, but these publications only mention the use of potassium carbonate or sodium carbonate in dioxane as catalyst. While the use of potassium cyanide or acetone cyanohydrin has been disclosed in connection with the similar rearrangement of enol esters of cyclohexane-1,3-diones (U.S. Pat. No. 4,695,673), the literature does not disclose any examples of cyanide compounds being especially useful for a Fries rearrangement of O-acyl derivatives of 5-hydroxypyrazole.

Work-up is carried out in a manner known per se, for example the reaction mixture is acidified with dilute mineral acids such as 5% strength hydrochloric acid or sulfuric acid and extracted using an organic solvent such as methylene chloride or ethyl acetate. For purification, the extract is extracted using cold 5 to 10% strength alkali metal carbonate solution, the end product being concentrated in the aqueous phase. The product of the formula Ia-Ie is precipitated by acidifying the aqueous solution or reextracted using methylene chloride or ethyl acetate, dried and subsequently freed from the solvent.

Those 5-hydroxypyrazoles of the formula II, used as starting material, which are not already known can be prepared by processes known per se (cf. EP-A 240 001 and J. Prakt. Chem. 315, 382 (1973)). 1,3-Dimethyl-5-hydroxypyrazole is a commercially available compound.

Benzoic acids of the formula III can be prepared as follows:

Benzoyl halides such as, for example, benzoyl chlorides of the formula III (T=Cl) are prepared in a manner known per se by reacting the benzoic acids of the formula III (T=OH) with thionyl chloride.

The benzoic acids of the formula III (T=OH) can be prepared in a known manner from the corresponding esters of the formula III (T=$C_1$–$C_4$-alkoxy) by means of acidic or basic hydrolysis.

Those intermediates of the formula III which are not already known can be prepared by processes known from the literature.

DIAGRAM 2

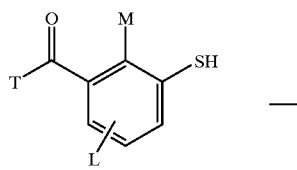

IV

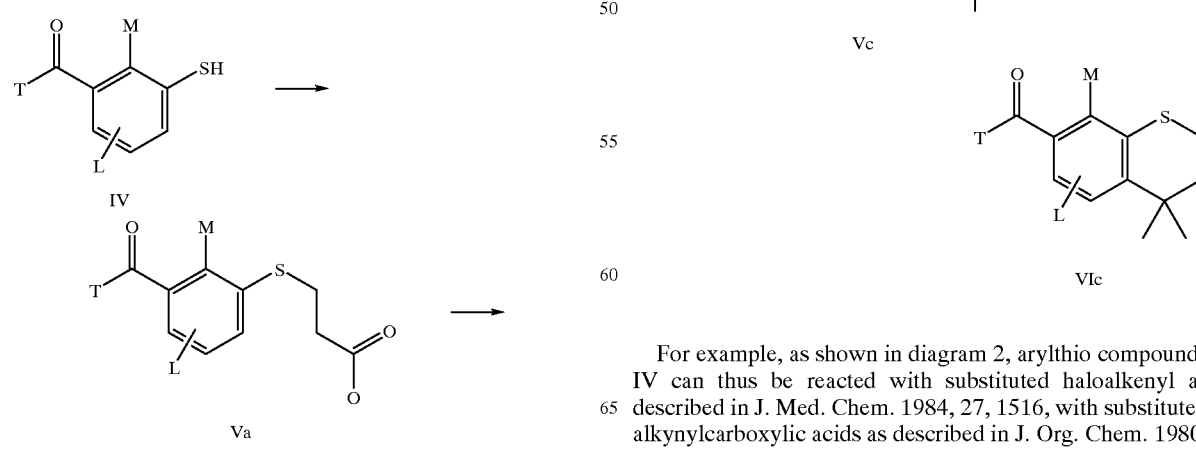

Va

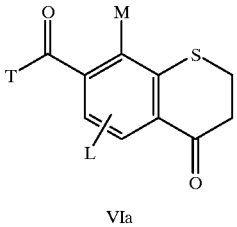

VIa

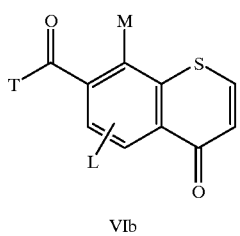

Vb

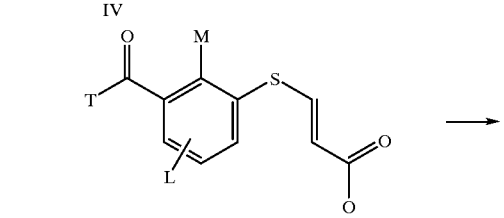

VIb

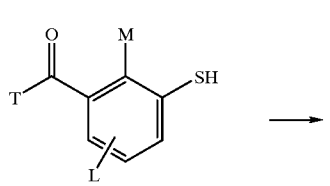

IV

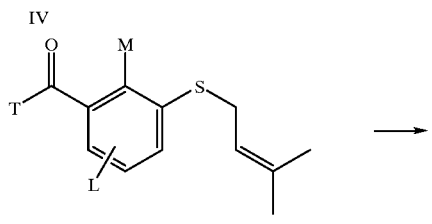

Vc

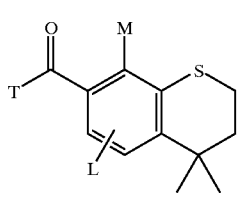

VIc

For example, as shown in diagram 2, arylthio compounds IV can thus be reacted with substituted haloalkenyl as described in J. Med. Chem. 1984, 27, 1516, with substituted alkynylcarboxylic acids as described in J. Org. Chem. 1980, 45, 4611 or J. Am. Chem. Soc. 1983, 105, 883, with substituted haloalkylcarboxylic acids as described in Chem. Ber. 1925, 58, 1612 in the presence of a base such as alkali metal hydroxide, alkali metal hydride or alkali metal carbonate. The resulting compounds V are cyclized to VI under Friedel-Crafts conditions with an addition of a Lewis acid or a protonic acid. Preferred, as described in Can. J. Chem. 1981, 59, 199; Chem. Ber. 1925, 58, 1625; Chem. Ber. 1926, 59, 1074; Phosp. and Sulf. 1984, 19, 31 are $AlCl_3$ or $SnCl_4$ as Lewis acids, and polyphoshoric [sic] acid and sulfuric acid as protonic acid.

Thiochromenone acids can furthermore be synthesized for example by eliminating hydrogen halide from 3-halothiochromanone acids or, for example, by reacting the substituted thiophenolic acids with substituted α-alkyl acetoacetates in the presence of phosphorus pentoxide as described in Ann. Chem. 1964, 680, 40.

The arylthio compounds IV can be obtained, for example, from corresponding anilines by means of a Sandmeyer reaction, and these anilines, in turn, are synthesized by reducing suitable nitro compounds as described in Organikum, 19th edition 1992, 552 et seq.

In the event that, for example, X equals ($—CR^{12}R^{13}—$) or ($—CR^{12}R^{13}CR^{21}R^{22}—$), Y equals C=O and T equals $C_1$–$C_4$-alkoxy, the thiochromanone ester or dihydrobenzothiophene ester can be prepared as described in diagram 2 by alkylating the arylthio compound IV with halopropionic acid or haloacetic acid in the presence of one of the abovementioned bases in solvent or water and the product cyclized to give VI.

The reactants and the base are expediently employed in equimolar amounts. The reaction mixture is stirred, preferably at 20–100° C., in particular at 20–40° C. Working-up is carried out, for example, in such a manner that the reaction mixture is poured into water, the aqueous phase is acidified using mineral acids such as hydrochloric acid or sulfuric acid, and the product of interest is filtered off with suction or extracted by means of extraction with methylene chloride or ethyl acetate, dried and freed from the solvent. The ester can be reacted without further purification.

Stirring V into, for example, polyphosphoric acid at 40–140° C., in particular at 70–100° C., or activating the carboxylic acid by converting it into its acid chloride and stirring with 2–6, in particular 3.5 to 4.5, mol equivalents of a Lewis acid, eg. $AlCl_3$ or $SnCl_4$, in a solvent or stirring with or in sulfuric acid gives, after work-up in a manner known per se, ie. adding icewater and removing the product of interest by filtration with suction or extraction of the aqueous phase using ethyl acetate or methylene chloride, drying and removing the solvent, an intermediate of the formula III.

In the event that, for example, X equals an ethylene group ($—CR^{12}=CR^{13}—$), Y equals C=O and T equals $C_1$–$C_4$-alkoxy, the thiochromenone ester can be reacted for example by reacting an arylthio compound with an acetylenecarboxylic acid derivative in water or solvent at from 0 to 140° C. Work-up is carried out in a manner known per se by adding water and dilute mineral acid, such as hydrochloric acid. The product of interest is either filtered off with suction or obtained by extraction using methylene chloride or ethyl acetate, followed by drying and removing the solvent.

The intermediates of the formula III can be functionalized further by reactions known from the literature, such as reduction as described by Jerry March "1 Advanced organic Chemistry, Fourth Ed., for example p. 910 et seq., oximation as described by Jerry March" Advanced Organic Chemistry, Fourth Ed., for example p. 934, 935, 1039, 1226, 405 et seq., conversion into imines and amines as described by Jerry March "Advanced Organic Chemistry, Fourth Ed., ketalization, alkylation, halogenation, elimination and oxidation as described by Jerry March" Advanced Organic Chemistry, Fourth Ed.

Starting from corresponding saccharine derivatives or 1,2-benzoisothiazoles, the acids of the 3-alkoxy-1,2-benzoisothiazole 1,1-dioxides or 3-alkoxy-1,2-benzoisothiazoles can be obtained, for example, by reaction with $PCl_5$, $POCl_3$ or chlorine and alcohol, in the presence or absence of an auxiliary base, eg. triethylamine, which is described, for example, in U.S. Pat. No. 4,571,429, Arch. Pharm. 1984, 317, 807, U.S. Pat. No. 4,461,901, U.S. Pat. No. 450,916, J. Med. Chem. 1986, 29, 359. Saccharine carboxylic acids can be obtained by processes known from the literature as described in Ann. Chem. 427, 231, 1922, Chem. Ber. 13, 1554, 1980, Chem. Ber. 25, 1740, 1892, DE-OS 3607343, German Patent Application P 44 27 995.7.

Those benzo-1,4-oxathiine acid derivatives which are not already known, for example from J. Org. Chem. 1968, 33, 456, can be synthesized from the corresponding phenol derivatives, for example, by reaction as described in Chem. Comm., 1975, 451, J. Org. Chem. 1974, 39, 1811, J. Am. Chem. Soc. 1954, 76, 1068 or by combination of, for example, substitution reaction on halogen-substituted thiophenol derivatives and subsequent reactions, eg. oxidation, reduction or addition as described in J. Het. Chem. 1983, 20, 867.

The benzoic acids of the formula III can also be obtained by reacting the corresponding bromine- or iodine-substituted compound of the formula VII

DIAGRAM 3

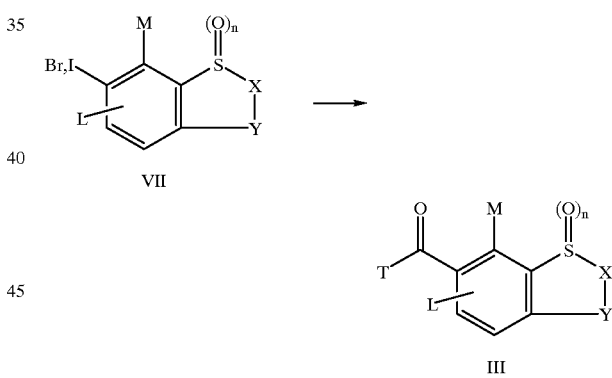

T is OH, $C_1$–$C_4$-alkoxy and

Y,L,M,X have the meanings described above with carbon monoxide and water under elevated pressure in the presence of a palladium, nickel, cobalt or rhodium transition metal catalyst and of a base.

The catalysts nickel, cobalt, rhodium and, in particular, palladium can be present in the form of metals or in the form of customary salts, such as in the form of halogen compounds, eg. $PdCl_2$, $RhCl_3.H_2O$, acetates, eg. $Pd(OAc)_2$, cyanides and the like at the known valency levels. Metal complexes with tertiary phosphines, metal alkyl carbonyls, metal carbonyls, eg. $CO_2(CO)_8$, $Ni(CO)_4$, metal carbonyl complexes with tertiary phosphines, eg. $[P(Ph)_3]_2Ni(CO)_2$, or with transition metal salts complexed with tertiary phosphines, may furthermore be present. The latter embodiment is preferred in particular in the case of palladium as the catalyst. The nature of the phosphine ligands varies within wide limits. For example, they can be represented by the following formulae:

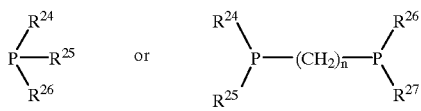

where n is the numbers 1, 2, 3 or 4 and the radicals $R^{24}$ to $R^{26}$ are low-molecular-weight alkyl, eg. $C_1-C_6$-alkyl, aryl, $C_1-C_4$-alkylaryl, eg. benzyl, phenethyl or aryloxy. Aryl is, for example, naphthyl, anthryl and, preferably, unsubstituted or substituted phenyl, where the substituents can be varied within a wide range as long as their being inert to the carboxylation reaction is taken into consideration and comprise all inert C-organic radicals such as $C_1-C_6$-alkyl radicals, eg. methyl, carboxyl radicals such as COOH, COOM (M is, for example, an alkali metal salt, alkaline earth metal salt or ammonium salt), or C-organic radicals which are bonded via oxygen, such as $C_1-C_6$-alkoxy radicals.

The phosphine complexes can be prepared in a manner known per se, for example as described in the documents mentioned at the outset. For example, the starting materials are customary commercially available metal salts such as $PdCl_2$ or $Pd(OCOCH_3)_2$, to which the phosphine, eg. $P(C_6H_5)_3$, $P(n-C_4H_9)_3$, $PCH_3(C_6H_5)_2$ or 1,2-bis (diphenylphosphino)ethane, is added.

The amount of phosphine based on the transition metal is usually 0 to 20, in particular 0.1 to 10, mol equivalents, especially preferably 1 to 5 mol equivalents.

The amount of transition metal is not critical. For commercial reasons, one will, of course, rather use a small amount, for example of from 0.1 to 10 mol%, in particular 1 to 5 mol%, based on the starting material II or III.

To prepare the benzoic acids III (T=OH), the reaction is carried out with carbon monoxide and at least equimolar amounts of water based on the starting materials VI. The reactant water can simultaneously also act as the solvent, ie. the maximum amount is not critical.

Depending on the nature of the starting materials and the catalysts used, however, it may also be advantageous to use, as the solvent, an inert solvent which differs from the reactant or the base which is used for the carboxylation reaction.

Inert solvents which are suitable for carboxylation reactions are customary solvents such as hydrocarbons, eg. toluene, xylene, hexane, pentane, cyclohexane, ethers, eg. methyl tert-butyl ether, tetrahydrofuran, dioxane, dimethoxyethane, substituted amides such as dimethylformamide, persubstituted ureas such as tetra-$C_1-C_4$-alkylureas or nitrites such as benzonitrile or acetonitrile.

In a preferred embodiment of the process, an excess of one of the reactants, in particular the base, is used, thus dispensing with an additional solvent.

The bases which are suitable for the process are all inert bases which are capable of binding the hydrogen iodide or hydrogen bromide which is liberated during the reaction. Examples are tertiary amines such as tert-alkylamines, eg. trialkylamines such as triethylamine, cyclic amines such as N-methylpiperidine or N,N'-dimethylpiperazine, pyridine, alkali metal carbonates or alkali metal hydrogen carbonates, or tetraalkyl-substituted urea derivatives such as tetra-$C_1-C_4$-alkylurea, eg. tetramethylurea.

The amount of base is not critical; 1 to 10, in particular 1 to 5, mol generally being used. When the base is simultaneously used as the solvent, the amount is generally so chosen that the reactants are dissolved, but unnecessarily high excesses are avoided for practical reasons to save costs, to be able to use small reaction vessels and to guarantee maximum contact between the reactants.

During the reaction, the carbon monoxide pressure is adjusted so that there is always an excess of CO based on VI. The carbon monoxide pressure is preferably from 1 to 250 bar, in particular from 5 to 150 bar, CO at room temperature.

The carbonylation reaction is generally carried out continuously or batchwise at from 20 to 250° C., in particular at from 30 to 150° C. In the case of a batchwise procedure, it is expedient to inject carbon monoxide continuously onto the reaction mixture so as to maintain constant pressure.

Those arylhalogen compounds VII, used as starting compounds, which are not already known can be prepared easily by a suitable combination of known syntheses and in accordance with the above-described reaction sequences.

With a view to the intended use of the pyrazol-4-ylbenzoyl derivatives of the general formula I, the following radicals are suitable as substituents:

L,M hydrogen, $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methylpropyl, in particular methyl, ethyl, 1-methylethyl, 1-methylpropyl, 2-methylpropyl, 1,1-dimethylethyl and 1,1-dimethylpropyl;

$C_2-C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3 butenyl [sic], 1,1-dimethyl-2-propenyl,1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3 pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2-C_6$-alkynyl such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2 propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2- dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_1$–$C_4$-alkoxy such as methoxy, ethoxy, n-propoxy, 1-methylethoxy, n-butoxy, 1-methylpropoxy, 2-methylpropoxy and 1,1-dimethylethoxy, in particular $C_1$–$C_3$-alkoxy such as methoxy, ethoxy, i-propoxy, it being possible for these groups to be unsubstituted or substituted by one to five halogen atoms such as fluorine, chlorine, bromine and iodine, preferably fluorine and chlorine, or $C_1$–$C_4$-alkoxy as mentioned above.

The group —$(A)_m$—$S(O)_nR^1$ defined above is, for example, $C_1$–$C_4$-alkylthio such as methylthio, ethylthio, n-propylthio, 1-methylethylthio, n-butylthio, 1-methylpropylthio, 2-methylpropylthio and 1,1-dimethylethylthio, in particular methylthio;

$C_1$–$C_4$-alkylsulfinyl such as methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, in particular methylsulfinyl;

$C_1$–$C_4$-alkylsulfonyl such as methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, in particular methylsulfonyl;

$C_1$–$C_4$-alkoxysulfonyl such as methoxysulfonyl, ethoxysulfonyl, n-propoxysulfonyl, 1-methylethoxysulfonyl, n-butoxysulfonyl, 1-methylpropoxysulfonyl, 2-methylpropoxysulfonyl and 1,1-dimethylethoxysulfonyl, in particular methoxysulfonyl;

N-$C_1$–$C_4$-alkylsulfamoyl such as N-methylsulfamoyl, N-ethylsulfamoyl, N-n-propylsulfamoyl, N-1-methylethylsulfamoyl, N-n-butylsulfamoyl, N-1-methylpropylsulfamoyl, N-2-methylpropylsulfamoyl and N-1,1-dimethylethylsulfamoyl, in particular N-methylsulfamoyl;

N-$C_1$–$C_4$-alkylsulfinamoyl such as N-methylsulfinamoyl, N-ethylsulfinamoyl, N-n-propylsulfinamoyl, N-1-methylethylsulfinamoyl, N-n-butylsulfinamoyl, N-1-methylpropylsulfinamoyl, N-2-methylpropylsulfinamoyl and N-1,1-dimethylethylsulfinamoyl, in particular N-methylsulfinamoyl;

di-$C_1$–$C_4$-alkylsulfamoyl such as dimethylsulfamoyl, diethylsulfamoyl, dipropylsulfamoyl, dibutylsulfamoyl, N-methyl-N-ethylsulfamoyl, N-methyl-N-propylsulfamoyl, N-methyl-N-1-methylethylsulfamoyl, N-methyl-N-1,1-dimethylethylsulfamoyl, di-1-methylethylsulfamoyl, N-ethyl-N-1-methylethylsulfamoyl and N-ethyl-N-1,1-dimethyl ethylsulfamoyl; in particular dimethylsulfamoyl;

di-$C_1$–$C_4$-alkylsulfinamoyl such as dimethylsulfinamoyl, diethylsulfinamoyl, dipropylsulfinamoyl, dibutylsulfinamoyl, N-methyl-N-ethylsulfinamoyl, N-methyl-N-propylsulfinamoyl, N-methyl-N-1-methylethylsulfinamoyl, N-methyl-N-1,1-dimethylethylsulfinamoyl, di-1-methylethylsulfinamoyl, N-ethyl-N-1-methylethylsulfinamoyl and N-ethyl-N-1,1-dimethylethylsulfinamoyl; in particular dimethylsulfinamoyl, $C_1$–$C_4$-alkylsulfinyloxy such as methylsulfinyloxy, ethylsulfinyloxy, n-propylsulfinyloxy, 1-methylethylsulfinyloxy, n-butylsulfinyloxy, 1-methylpropylsulfinyloxy, 2-methylpropylsulfinyloxy and 1,1-dimethylethylsulfinyloxy, in particular methylsulfinyloxy;

$C_1$–$C_4$-alkylsulfonyloxy such as methylsulfonyloxy, ethylsulfonyloxy, n-propylsulfonyloxy, 1-methylethylsulfonyloxy, n-butylsulfonyloxy, 1-methylpropylsulfonyloxy, 2-methylpropylsulfonyloxy and 1,1-dimethylethylsulfonyloxy, in particular methylsulfonyloxy;

$C_1$–$C_4$-alkylsulfinylamino such as methylsulfinylamino, ethylsulfinylamino, n-propylsulfinylamino, 1-methylethylsulfinylamino, n-butylsulfinylamino, 1-methylpropylsulfinylamino, 2-methylpropylsulfinylamino and 1,1-dimethylethylsulfinylamino, in particular methylsulfinylamino;

$C_1$–$C_4$-alkylsulfonylamino such as methylsulfonylamino, ethylsulfonylamino, n-propylsulfonylamino, 1-methylethylsulfonylamino, n-butylsulfonylamino, 1-methylpropylsulfonylamino, 2-methylpropylsulfonylamino and 1,1-dimethylethylsulfonylamino, in particular methylsulfonylamino;

N-$C_1$–$C_4$-alkylsulfinyl-N-methylamino such as N-methylsulfinyl-N-methylamino, N-ethylsulfinyl-N-methylamino, N-n-propylsulfinyl-N-methylamino, N-1-methylethylsulfinyl-N-methylamino, N-n-butylsulfinyl-N-methylamino, N-1-methylpropylsulfinyl-N-methylamino, N-2-methylpropylsulfinyl-N-methylamino and N-1,1-dimethylethylsulfinyl-N-methylamino, in particular N-methylsulfinyl-N-methylamino;

N-$C_1$–$C_4$-alkylsulfinyl-N-ethylamino such as N-methylsulfinyl-N-ethylamino, N-ethylsulfinyl-N-ethylaminot N-n-propylsulfinyl-N-ethylamino, N-1-methylethylsulfinyl-N-ethylamino, N-n-butylsulfinyl-N-ethylamino, N-1-methylpropylsulfinyl-N-ethylamino, N-2-methylpropylsulfinyl-N-ethylamino and N-1,1-dimethylethylsulfinyl-N-ethylamino, in particular N-methylsulfinyl-N-ethylamino;

N-$C_1$–$C_4$-alkylsulfonyl-N-methylamino such as N-methylsulfonyl-N-methylamino, N-ethylsulfonyl-N-methylamino, N-n-propylsulfonyl-N-methylamino, N-1-methylethylsulfonyl-N-methylamino, N-n-butylsulfonyl-N-methylamino, N-1-methylpropylsulfonyl-N-methylamino, N-2-methylpropylsulfonyl-N-methylamino and N-1,1-dimethylethylsulfonyl-N-methylamino, in particular N-methylsulfonyl-N-methylamino;

N-$C_1$–$C_4$-alkylsulfonyl-N-ethylamino such as N-methylsulfonyl-N-ethylamino, N-ethylsulfonyl-N-ethylamino, N-n-propylsulfonyl-N-ethylamino, N-1-methylethylsulfonyl-N-ethylamino, N-n-butylsulfonyl-N-ethylamino, N-1-methylpropylsulfonyl-N-ethylamino, N-2-methylpropylsulfonyl-N-ethylamino and N-1,1-dimethylethylsulfonyl-N-ethylamino, in particular N-methylsulfonyl-N-ethylamino;

$C_1$–$C_4$-haloalkylthio such as chloromethylthio, dichloromethylthio, trichloromethylthio, fluoromethylthio, difluoromethylthio, trifluoromethylthio, chlorofluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, in particular trifluoromethylthio.

The group —$(A)_m$—CO—$R^2$ defined above is, for example, $C_1$–$C_4$-alkylcarbonyl such as methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl, in particular methylcarbonyl;

$C_1$–$C_4$-alkoxycarbonyl such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;

N-$C_1$–$C_4$-alkylcarbamoyl such as N-methylcarbamoyl, N-ethylcarbamoyl, N-n-propylcarbamoyl, N-1-methylethylcarbamoyl, N-n-butylcarbamoyl, N-1-methylpropylcarbamoyl, N-2-methylpropylcarbamoyl and N-1,1-dimethylethylcarbamoyl, in particular N-methylcarbamoyl;

di-$C_1$–$C_4$-alkylcarbamoyl such as dimethylcarbamoyl, diethylcarbamoyl, dipropylcarbamoyl, dibutylcarbamoyl, N-methyl-N-ethylcarbamoyl, N-methyl-N-propylcarbamoyl, N-methyl-N-1-methylethylcarbamoyl, N-methyl-N-1,1-dimethylethylcarbamoyl, di-1-methylethylcarbamoyl, N-ethyl-N-1-methylethylcarbamoyl and N-ethyl-N-1,1-dimethylethylcarbamoyl; in particular dimethylcarbamoyl;

$C_1$–$C_4$-alkylcarbonyloxy such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy and 1,1-dimethylethylcarbonyloxy, in particular methylcarbonyloxy;

$C_1$–$C_4$-alkylcarbonylamino such as methylcarbonylamino, ethylcarbonylamino, n-propylcarbonylamino, 1-methylethylcarbonylamino, n-butylcarbonylamino, 1-methylpropylcarbonylamino, 2-methylpropylcarbonylamino and 1,1-dimethylethylcarbonylamino, in particular methylcarbonylamino;

N-$C_1$–$C_4$-alkylcarbonyl-N-methylamino such as N-methylcarbonyl-N-methylamino, N-ethylcarbonyl-N-methylamino, N-n-propylcarbonyl-N-methylamino, N-1-methylethylcarbonyl-N-methylamino, N-n-butylcarbonyl-N-methylamino, N-1-methylpropylcarbonyl-N-methylamino, N-2-methylpropylcarbonyl-N-methylamino and N-1,1-dimethylethylcarbonyl-N-methylamino, in particular N-methylcarbonyl-N-methylamino.

X is, for example, $CH_2$, $CH(CH_3)$, $C((CH_3)_2)$, $CH(C_2H_5)$, $C((C_2H_5)_2)$, $CH(C_6H_5)$, $CH_2$—$CH_2$, $CH_2$—$CH(CH_3)$, $CH_2$—$C((CH_3)_2)$, $CH(CH_3)$—$CH(CH_3)$, $CH(CH_3)$—$C((CH_3)_2)$, $C((CH_3)_2)$—$C((CH_3)_2)$, $CH_2$—$CH(C_2H_5)$, $CH_2$—$C((C_2H_5)_2)$, $CH(C_2H_5)$—$CH(C_2H_5)$, $CH(C_2H_5)$—$C((C_2H_5)_2)$, $C((C_2H_5)_2)$—$C((C_2H_5)_2)$, $CH_2$—$CH(C_3H_7)$, $CH_2$—$CH(iC_3H_7)$, $CH_2$—$CH(C_4H_9)$, $CH_2$—$CH(iC_4H_9)$, $CH_2$—$CH(Br)$, $CH_2$—$C((Br)_2)$, $CH(Br)$—$CH(Br)$, $C((Br)_2)$—$C((Br)_2)$, $CH_2$—$CH(Cl)$, $CH_2$—$C((Cl)_2)$, $CH(Cl)$—$C((Cl)_2)$, $C((Cl)_2)$—$C((Cl)_2)$, $CH_2$—$CH(C_6H_5)$, $CH(C_6H_5)$—$CH(C_6H_5)$, $CH_2$—$CH(p$—$NO_2C_6H_5)$, $CH$=$CH$, $C(CH_3)$=$CH$, $C(CH_3)$=$CCH_3$, $CH$=$CBr$, $CH$=$CCl$, $CBr$=$CBr$, $CCl$=$CCl$, $CH$=$C(OCH_3)$, $CH$=$C(C_6H_5)$, $C(C_6H_5)$=$C(C_6H_5)$, $C(C_2H_5)$=$CH$, $C(C_2H_5)$=$C(C_2H_5)$, $CH$=$C(C_3H_5)$, $CH$=$C(C_4H_7)$, $CH_2$—$CH$=$CH$, $CH(CH_3)$—$CH$=$CH$, $C((CH_3)_2)$—$CH$=$CH$, $CH_2$—$CH$=$C(CH_3)$, $CH_2$—$C(CH_3)$=$CH$, $CH_2$—$C(CH_3)$=$C(CH_3)$, $CH(CH_3)$—$C(CH_3)$=$C(CH_3)$, $C((CH_3)_2)$—$C(CH_3)$=$C(CH_3)$, N—H, N—$CH_3$, N—$C_2H_5$, N—$C_3H_7$, N—$C_4H_9$, N—$iCH_3H_7$, N—$OCH_3$, N—$OC_2H_5$, N—$CH_2C_6H_5$, N—$C_2H_5$, Y is, for example, C=O, CH—OH, CH—$OCH_3$, CH—$OC_2H_5$, CH—$OC_3H_7$, CH—OiPr, CH—$OC_4H_9$, CH—OiBu, CH—$OC_5H_{11}$, CH—$OC_6H_{13}$, CH—$OC_6H_5$, $C(CH_3)$—$OCH_3$, $C(CH_3)$—$OC_2H_5$, $C(CH_3)$—$OC_3H_7$, $C(CH_3)$—$OC_4H_9$, $C(CH_3)$-OiPr, $C(CH_3)$—OiBu, $C(CH_3)$—OtBu, $C(CH_3)$—OPh, $CH_2$, $CH(CH_3)$, $C((CH_3)_2)$, C=N—$CH_3$, C=N—$C_2H_5$, C=N—$C_3H_7$, CN=$C_4H_9$, C=N—$iC_4H_9$, C=N—$tC_4H_9$, C=N—iPr, C=N—$OCH_3$, C=N—$OC_2H_5$, C=N—$OC_3H_7$, C=N—$OC_4H_9$, C=N—$OiC_4H_9$, C=N—$OtC_4H_9$, C=N—$OCH_2CH$=$CH_2$, C=N—$OCH(CH_3)CH$=$CH_2$, C=N—$OCH_2CH$=$CHCH_3$, C=N—$OCH_2CH$=$C(CH_3)_2$, C=N—$OCH_2CH$=$CHBr$, C=N—$OCH_2CH$=$CHCl$, C=N—$OCH_2CH$=$CHC_2H_5$, C=N—$OCH_2C$≡CH, C=N—$OCH_2C$≡$CCH3$, C=N—$OCH_2C_6H_5$, CH—$NH(OCH_3)$, CH—$NH(OC_2H_5)$, CH—NH(OiPr), CH—NH(OnPr), CH—$NH(OC_6H_5)$, CH—$NCH_3(OCH_3)$, CH—$NCH_3(OC_2H_5)$, CH—$NCH_3(OiPr)$, CH—$NCH_3(OnPr)$, CH—$NCH_3(OC_6H_5)$, CH—$NH(CH_3)$, CH—$NH(C_2H_5)$, CH—$NH(C_3H_7)$, CH—$NH(C_4H_9)$, CH—NH(iPr), CH—NH(iBu), CH—NH(tBu), CH—$NH(C_6H_5)$, CH—$N(CH_3)_2$, CH—$NCH_3(C_2H_5)$, CH—$NCH_3(C_3H_7)$, CH—$NCH_3(C_4H_9)$, CH—$NCH_3$(iPr), CH—$NCH_3$(iBu), C=N—$NH_2$, C=N—$NHCH_3$, C=N—$N((CH_3)_2)$, C=N—$NH(C_2H_5)$, C=N—$NCH_3(C_2H_5)$, C=N—$N((C_2H_5)_2)$, CH—$SCH_3$, CH—$SC_2H_5$, CH—$SC_3H_7$, CH—$SC_4H_9$, CH—SPr, CH—SiBu, CH—SH, $C(CH_3)$—$SCH_3$, $C(CH_3)$—$SC_2H_5$, $C(CH_3)$—$SC_3H_7$, 1,3-dioxanyl, 1,3-dioxolanyl, 5,5-dimethyl-1,3-dioxanyl.

Preferred pyrazol-4-ylbenzoyl derivatives are those of the formula Ia

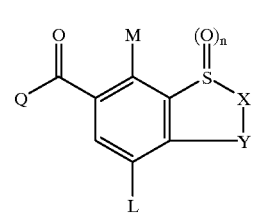

Ia where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkoxy, $C_1$–$C_4$-haloalkylthio, $C_1$–$C_4$-alkylsulfonyl, halogen, nitro or cyano and Q, X, n and Y have the abovementioned meanings, where, in the event that Y=C=O, X is other than $NR^{23}$.

Furthermore preferred pyrazol-4-ylbenzoyl derivatives are those of the formula Ib

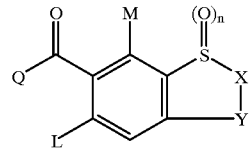

Ib where L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and M is hydrogen $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, X, n and Y have the abovementioned meanings, where, in the event that Y=C=O, X is other than $NR^{23}$.

Further preferred pyrazol-4-ylbenzoyl derivatives of the formula I are those where the radicals L and M are hydrogen, methyl, methoxy, chlorine, cyano, nitro or trifluoromethyl.

Preferred pyrazol-4-ylbenzoyl derivatives are those of the formula Ic

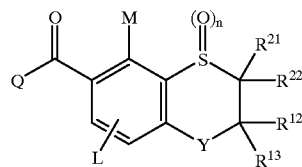

Ic where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, n, Y and $R^{22}$, $R^{21}$, $R^{12}$ and $R^{13}$ have the abovementioned meanings.

Also preferred pyrazol-4-ylbenzoyl derivatives are those of the formula Id

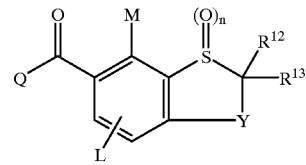

Id where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, n, Y and $R^{12}$ and $R^{13}$ have the abovementioned meanings.

Other preferred pyrazol-4-ylbenzoyl derivatives are those of the formula Ie

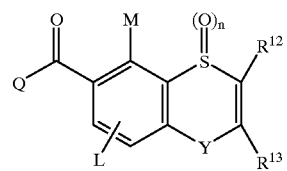

Ie where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, n, Y and $R^{12}$ and $R^{13}$ have the abovementioned meanings.

Other preferred pyrazol-4-ylbenzoyl derivatives of the formula I are those where n is one or two and Y is $CR^{7-OR8}$, where $R^7$ and $R^8$ have the abovementioned meanings.

TABLE 1

Compounds of the formula

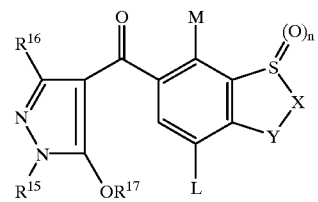

| No. | $R^{15}$ | $R^{16}$ | $R^{17}$ | n | X | Y | L | M |
|---|---|---|---|---|---|---|---|---|
| 1.1 | $CH_3$ | $CH_3$ | H | 0 | $CH_2$ | C=O | H | H |
| 1.2 | $CH_3$ | $CH_3$ | H | 2 | $CH_2$ | C=O | H | H |
| 1.3 | $CH_3$ | $CH_3$ | H | 0 | $CH_2$ | $CHOCH_3$ | H | H |
| 1.4 | $CH_3$ | $CH_3$ | H | 2 | $CH_2$ | $CHOCH_3$ | H | H |
| 1.5 | $CH_3$ | $CH_3$ | H | 0 | $CH_2$ | $CHOC_2H_5$ | H | H |
| 1.6 | $CH_3$ | $CH_3$ | H | 2 | $CH_2$ | $CHOC_2H_5$ | H | H |
| 1.7 | $CH_3$ | $CH_3$ | H | 0 | $CH_2$ | CHOiPr | H | H |
| 1.8 | $CH_3$ | $CH_3$ | H | 2 | $CH_2$ | CHOiPr | H | H |
| 1.9 | $CH_3$ | $CH_3$ | H | 0 | $CH_2$ | CHOH | H | H |

TABLE 1-continued

Compounds of the formula

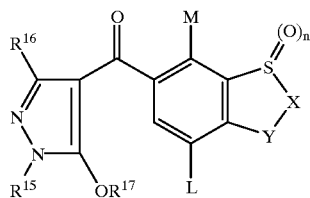

| No. | $R^{15}$ | $R^{16}$ | $R^{17}$ | n | X | Y | L | M |
|---|---|---|---|---|---|---|---|---|
| 1.10 | $CH_3$ | $CH_3$ | H | 2 | $CH_2$ | CHOH | H | H |
| 1.11 | $CH_3$ | $CH_3$ | H | 0 | $CH_2$ | C=NOCH$_3$ | H | H |
| 1.12 | $CH_3$ | $CH_3$ | H | 2 | $CH_2$ | C=NOCH$_3$ | H | H |
| 1.13 | $CH_3$ | $CH_3$ | H | 0 | $CH_2$ | C=NOC$_2$H$_5$ | H | H |
| 1.14 | $CH_3$ | $CH_3$ | H | 2 | $CH_2$ | C=NOC$_2$H$_5$ | H | H |
| 1.15 | $CH_3$ | $CH_3$ | H | 0 | $CH_2$ | C=NOiPr | H | H |
| 1.16 | $CH_3$ | $CH_3$ | H | 2 | $CH_2$ | C=NOiPr | H | H |
| 1.17 | $CH_3$ | $CH_3$ | H | 0 | $CH_2$ | C=NOCH$_2$CH=CHCl | H | H |
| 1.18 | $CH_3$ | $CH_3$ | H | 2 | $CH_2$ | C=NOCH$_2$CH=CHCl | H | H |
| 1.19 | $CH_3$ | $CH_3$ | H | 0 | $CH_2$ | C=NOCH$_2$C$_6$H$_5$ | H | H |
| 1.20 | $CH_3$ | $CH_3$ | H | 2 | $CH_2$ | C=NOCH$_2$C$_6$H$_5$ | H | H |
| 1.21 | $CH_3$ | $CH_3$ | H | 0 | $CH_2$ | C(CH$_3$)$_2$ | H | H |
| 1.22 | $CH_3$ | $CH_3$ | H | 2 | $CH_2$ | C(CH$_3$)$_2$ | H | H |
| 1.23 | $C_2H_5$ | H | H | 0 | $CH_2$ | C=O | H | H |
| 1.24 | $C_2H_5$ | H | H | 2 | $CH_2$ | C=O | H | H |
| 1.25 | $C_2H_5$ | H | H | 0 | $CH_2$ | CHOCH$_3$ | H | H |
| 1.26 | $C_2H_5$ | H | H | 2 | $CH_2$ | CHOCH$_3$ | H | H |
| 1.27 | $C_2H_5$ | H | H | 0 | $CH_2$ | CHOC$_2$H$_5$ | H | H |
| 1.28 | $C_2H_5$ | H | H | 2 | $CH_2$ | CHOC$_2$H$_5$ | H | H |
| 1.29 | $C_2H_5$ | H | H | 0 | $CH_2$ | CHOiPr | H | H |
| 1.30 | $C_2H_5$ | H | H | 2 | $CH_2$ | CHOiPr | H | H |
| 1.31 | $C_2H_5$ | H | H | 0 | $CH_2$ | CHOH | H | H |
| 1.32 | $C_2H_5$ | H | H | 2 | $CH_2$ | CHOH | H | H |
| 1.33 | $C_2H_5$ | H | H | 0 | $CH_2$ | C=NOCH$_3$ | H | H |
| 1.34 | $C_2H_5$ | H | H | 2 | $CH_2$ | C=NOCH$_3$ | H | H |
| 1.35 | $C_2H_5$ | H | H | 0 | $CH_2$ | C=NOC$_2$H$_5$ | H | H |
| 1.36 | $C_2H_5$ | H | H | 2 | $CH_2$ | C=NOC$_2$H$_5$ | H | H |
| 1.37 | $C_2H_5$ | H | H | 0 | $CH_2$ | C=NOiPr | H | H |
| 1.38 | $C_2H_5$ | H | H | 2 | $CH_2$ | C=NOiPr | H | H |
| 1.39 | $C_2H_5$ | H | H | 0 | $CH_2$ | C=NOCH$_2$CH=CHCl | H | H |
| 1.40 | $C_2H_5$ | H | H | 2 | $CH_2$ | C=NOCH$_2$CH=CHCl | H | H |
| 1.41 | $C_2H_5$ | H | H | 0 | $CH_2$ | C=NOCH$_2$C$_6$H$_5$ | H | H |
| 1.42 | $C_2H_5$ | H | H | 2 | $CH_2$ | C=NOCH$_2$C$_6$H$_5$ | H | H |
| 1.43 | $C_2H_5$ | H | H | 0 | $CH_2$ | C(CH$_3$)$_2$ | H | H |
| 1.44 | $C_2H_5$ | H | H | 2 | $CH_2$ | C(CH$_3$)$_2$ | H | H |
| 1.45 | $CH_3$ | $CH_3$ | H | 0 | $CH_2$ | C=O | H | $CH_3$ |
| 1.46 | $CH_3$ | $CH_3$ | H | 2 | $CH_2$ | C=O | H | $CH_3$ |
| 1.47 | $CH_3$ | $CH_3$ | H | 0 | $CH_2$ | CHOCH$_3$ | H | $CH_3$ |
| 1.48 | $CH_3$ | $CH_3$ | H | 2 | $CH_2$ | CHOCH$_3$ | H | $CH_3$ |
| 1.49 | $CH_3$ | $CH_3$ | H | 0 | $CH_2$ | CHOC$_2$H$_5$ | H | $CH_3$ |
| 1.50 | $CH_3$ | $CH_3$ | H | 2 | $CH_2$ | CHOC$_2$H$_5$ | H | $CH_3$ |
| 1.51 | $CH_3$ | $CH_3$ | H | 0 | $CH_2$ | CHOiPr | H | $CH_3$ |
| 1.52 | $CH_3$ | $CH_3$ | H | 2 | $CH_2$ | CHOiPr | H | $CH_3$ |
| 1.53 | $CH_3$ | $CH_3$ | H | 0 | $CH_2$ | CHOH | H | $CH_3$ |
| 1.54 | $CH_3$ | $CH_3$ | H | 2 | $CH_2$ | CHOH | H | $CH_3$ |
| 1.55 | $CH_3$ | $CH_3$ | H | 0 | $CH_2$ | C=NOCH$_3$ | H | $CH_3$ |
| 1.56 | $CH_3$ | $CH_3$ | H | 2 | $CH_2$ | C=NOCH$_3$ | H | $CH_3$ |
| 1.57 | $CH_3$ | $CH_3$ | H | 0 | $CH_2$ | C=NOC$_2$H$_5$ | H | $CH_3$ |
| 1.58 | $CH_3$ | $CH_3$ | H | 2 | $CH_2$ | C=NOC$_2$H$_5$ | H | $CH_3$ |
| 1.59 | $CH_3$ | $CH_3$ | H | 0 | $CH_2$ | C=NOiPr | H | $CH_3$ |
| 1.60 | $CH_3$ | $CH_3$ | H | 2 | $CH_2$ | C=NOiPr | H | $CH_3$ |
| 1.61 | $CH_3$ | $CH_3$ | H | 0 | $CH_2$ | C=NOCH$_2$CH=CHCl | H | $CH_3$ |
| 1.62 | $CH_3$ | $CH_3$ | H | 2 | $CH_2$ | C=NOCH$_2$CH=CHCl | H | $CH_3$ |
| 1.63 | $CH_3$ | $CH_3$ | H | 0 | $CH_2$ | C=NOCH$_2$C$_6$H$_5$ | H | $CH_3$ |
| 1.64 | $CH_3$ | $CH_3$ | H | 2 | $CH_2$ | C=NOCH$_2$C$_6$H$_5$ | H | $CH_3$ |
| 1.65 | $CH_3$ | $CH_3$ | H | 0 | $CH_2$ | C(CH$_3$)$_2$ | H | $CH_3$ |
| 1.66 | $CH_3$ | $CH_3$ | H | 2 | $CH_2$ | C(CH$_3$)$_2$ | H | $CH_3$ |
| 1.67 | $C_2H_5$ | H | H | 0 | $CH_2$ | C=O | H | $CH_3$ |
| 1.68 | $C_2H_5$ | H | H | 2 | $CH_2$ | C=O | H | $CH_3$ |
| 1.69 | $C_2H_5$ | H | H | 0 | $CH_2$ | CHOCH$_3$ | H | $CH_3$ |
| 1.70 | $C_2H_5$ | H | H | 2 | $CH_2$ | CHOCH$_3$ | H | $CH_3$ |
| 1.71 | $C_2H_5$ | H | H | 0 | $CH_2$ | CHOC$_2$H$_5$ | H | $CH_3$ |
| 1.72 | $C_2H_5$ | H | H | 2 | $CH_2$ | CHOC$_2$H$_5$ | H | $CH_3$ |

TABLE 1-continued

Compounds of the formula

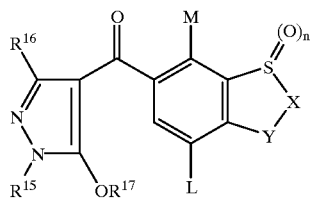

| No. | R15 | R16 | R17 | n | X | Y | L | M |
|---|---|---|---|---|---|---|---|---|
| 1.73 | C2H5 | H | H | 0 | CH2 | CHOiPr | H | CH3 |
| 1.74 | C2H5 | H | H | 2 | CH2 | CHOiPr | H | CH3 |
| 1.75 | C2H5 | H | H | 0 | CH2 | CHOH | H | CH3 |
| 1.76 | C2H5 | H | H | 2 | CH2 | CHOH | H | CH3 |
| 1.77 | C2H5 | H | H | 0 | CH2 | C=NOCH3 | H | CH3 |
| 1.78 | C2H5 | H | H | 2 | CH2 | C=NOCH3 | H | CH3 |
| 1.79 | C2H5 | H | H | 0 | CH2 | C=NOC2H5 | H | CH3 |
| 1.80 | C2H5 | H | H | 2 | CH2 | C=NOC2H5 | H | CH3 |
| 1.81 | C2H5 | H | H | 0 | CH2 | C=NOiPr | H | CH3 |
| 1.82 | C2H5 | H | H | 2 | CH2 | C=NOiPr | H | CH3 |
| 1.83 | C2H5 | H | H | 0 | CH2 | C=NOCH2CH=CHCl | H | CH3 |
| 1.84 | C2H5 | H | H | 2 | CH2 | C=NOCH2CH=CHCl | H | CH3 |
| 1.85 | C2H5 | H | H | 0 | CH2 | C=NOCH2C6H5 | H | CH3 |
| 1.86 | C2H5 | H | H | 2 | CH2 | C=NOCH2C6H5 | H | CH3 |
| 1.87 | C2H5 | H | H | 0 | CH2 | C(CH3)2 | H | CH3 |
| 1.88 | C2H5 | H | H | 2 | CH2 | C(CH3)2 | H | CH3 |
| 1.89 | CH3 | CH3 | H | 0 | CH2 | C=O | H | Cl |
| 1.90 | CH3 | CH3 | H | 2 | CH2 | C=O | H | Cl |
| 1.91 | CH3 | CH3 | H | 0 | CH2 | CHOCH3 | H | Cl |
| 1.92 | CH3 | CH3 | H | 2 | CH2 | CHOCH3 | H | Cl |
| 1.93 | CH3 | CH3 | H | 0 | CH2 | CHOC2H5 | H | Cl |
| 1.94 | CH3 | CH3 | H | 2 | CH2 | CHOC2H5 | H | Cl |
| 1.95 | CH3 | CH3 | H | 0 | CH2 | CHOiPr | H | Cl |
| 1.96 | CH3 | CH3 | H | 2 | CH2 | CHOiPr | H | Cl |
| 1.97 | CH3 | CH3 | H | 0 | CH2 | CHOH | H | Cl |
| 1.98 | CH3 | CH3 | H | 2 | CH2 | CHOH | H | Cl |
| 1.99 | CH3 | CH3 | H | 0 | CH2 | C=NOCH3 | H | Cl |
| 1.100 | CH3 | CH3 | H | 2 | CH2 | C=NOCH3 | H | Cl |
| 1.101 | CH3 | CH3 | H | 0 | CH2 | C=NOC2H5 | H | Cl |
| 1.102 | CH3 | CH3 | H | 2 | CH2 | C=NOC2H5 | H | Cl |
| 1.103 | CH3 | CH3 | H | 0 | CH2 | C=NOiPr | H | Cl |
| 1.104 | CH3 | CH3 | H | 2 | CH2 | C=NOiPr | H | Cl |
| 1.105 | CH3 | CH3 | H | 0 | CH2 | C=NOCH2CH=CHCl | H | Cl |
| 1.106 | CH3 | CH3 | H | 2 | CH2 | C=NOCH2CH=CHCl | H | Cl |
| 1.107 | CH3 | CH3 | H | 0 | CH2 | C=NOCH2C6H5 | H | Cl |
| 1.108 | CH3 | CH3 | H | 2 | CH2 | C=NOCH2C6H5 | H | Cl |
| 1.109 | CH3 | CH3 | H | 0 | CH2 | C(CH3)2 | H | Cl |
| 1.110 | CH3 | CH3 | H | 2 | CH2 | C(CH3)2 | H | Cl |
| 1.111 | C2H5 | H | H | 0 | CH2 | C=O | H | Cl |
| 1.112 | C2H5 | H | H | 2 | CH2 | C=O | H | Cl |
| 1.113 | C2H5 | H | H | 0 | CH2 | CHOCH3 | H | Cl |
| 1.114 | C2H5 | H | H | 2 | CH2 | CHOCH3 | H | Cl |
| 1.115 | C2H5 | H | H | 0 | CH2 | CHOC2H5 | H | Cl |
| 1.116 | C2H5 | H | H | 2 | CH2 | CHOC2H5 | H | Cl |
| 1.117 | C2H5 | H | H | 0 | CH2 | CHOiPr | H | Cl |
| 1.118 | C2H5 | H | H | 2 | CH2 | CHOiPr | H | Cl |
| 1.119 | C2H5 | H | H | 0 | CH2 | CHOH | H | Cl |
| 1.120 | C2H5 | H | H | 2 | CH2 | CHOH | H | Cl |
| 1.121 | C2H5 | H | H | 0 | CH2 | C=NOCH3 | H | Cl |
| 1.122 | C2H5 | H | H | 2 | CH2 | C=NOCH3 | H | Cl |
| 1.123 | C2H5 | H | H | 0 | CH2 | C=NOC2H5 | H | Cl |
| 1.124 | C2H5 | H | H | 2 | CH2 | C=NOC2H5 | H | Cl |
| 1.125 | C2H5 | H | H | 0 | CH2 | C=NOiPr | H | Cl |
| 1.126 | C2H5 | H | H | 2 | CH2 | C=NOiPr | H | Cl |
| 1.127 | C2H5 | H | H | 0 | CH2 | C=NOCH2CH=CHCl | H | Cl |
| 1.128 | C2H5 | H | H | 2 | CH2 | C=NOCH2CH=CHCl | H | Cl |
| 1.129 | C2H5 | H | H | 0 | CH2 | C=NOCH2C6H5 | H | Cl |
| 1.130 | C2H5 | H | H | 2 | CH2 | C=NOCH2C6H5 | H | Cl |
| 1.131 | C2H5 | H | H | 0 | CH2 | C(CH3)2 | H | Cl |
| 1.132 | C2H5 | H | H | 2 | CH2 | C(CH3)2 | H | Cl |
| 1.133 | CH3 | CH3 | H | 0 | (CH2)2 | C=O | H | Cl |
| 1.134 | CH3 | CH3 | H | 2 | (CH2)2 | C=O | H | Cl |
| 1.135 | CH3 | CH3 | H | 0 | (CH2)2 | CHOCH3 | H | Cl |

TABLE 1-continued

Compounds of the formula

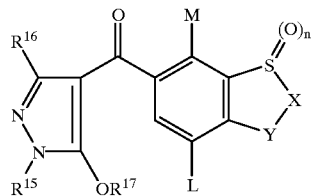

| No. | R15 | R16 | R17 | n | X | Y | L | M |
|---|---|---|---|---|---|---|---|---|
| 1.136 | CH$_3$ | CH$_3$ | H | 2 | (CH$_2$)$_2$ | CHOCH$_3$ | H | Cl |
| 1.137 | CH$_3$ | CH$_3$ | H | 0 | (CH$_2$)$_2$ | CHOC$_2$H$_5$ | H | Cl |
| 1.138 | CH$_3$ | CH$_3$ | H | 2 | (CH$_2$)$_2$ | CHOC$_2$H$_5$ | H | Cl |
| 1.139 | CH$_3$ | CH$_3$ | H | 0 | (CH$_2$)$_2$ | CHOiPr | H | Cl |
| 1.140 | CH$_3$ | CH$_3$ | H | 2 | (CH$_2$)$_2$ | CHOiPr | H | Cl |
| 1.141 | CH$_3$ | CH$_3$ | H | 0 | (CH$_2$)$_2$ | CHOH | H | Cl |
| 1.142 | CH$_3$ | CH$_3$ | H | 2 | (CH$_2$)$_2$ | CHOH | H | Cl |
| 1.143 | CH$_3$ | CH$_3$ | H | 0 | (CH$_2$)$_2$ | C=NOCH$_3$ | H | Cl |
| 1.144 | CH$_3$ | CH$_3$ | H | 2 | (CH$_2$)$_2$ | C=NOCH$_3$ | H | Cl |
| 1.145 | CH$_3$ | CH$_3$ | H | 0 | (CH$_2$)$_2$ | C=NOC$_2$H$_5$ | H | Cl |
| 1.146 | CH$_3$ | CH$_3$ | H | 2 | (CH$_2$)$_2$ | C=NOC$_2$H$_5$ | H | Cl |
| 1.147 | CH$_3$ | CH$_3$ | H | 0 | (CH$_2$)$_2$ | C=NOiPr | H | Cl |
| 1.148 | CH$_3$ | CH$_3$ | H | 2 | (CH$_2$)$_2$ | C=NOiPr | H | Cl |
| 1.149 | CH$_3$ | CH$_3$ | H | 0 | (CH$_2$)$_2$ | C=NOCH$_2$CH=CHCl | H | Cl |
| 1.150 | CH$_3$ | CH$_3$ | H | 2 | (CH$_2$)$_2$ | C=NOCH$_2$CH=CHCl | H | Cl |
| 1.151 | CH$_3$ | CH$_3$ | H | 0 | (CH$_2$)$_2$ | C=NOCH$_2$C$_6$H$_5$ | H | Cl |
| 1.152 | CH$_3$ | CH$_3$ | H | 2 | (CH$_2$)$_2$ | C=NOCH$_2$C$_6$H$_5$ | H | Cl |
| 1.153 | CH$_3$ | CH$_3$ | H | 0 | (CH$_2$)$_2$ | C(CH$_3$)$_2$ | H | Cl |
| 1.154 | CH$_3$ | CH$_3$ | H | 2 | (CH$_2$)$_2$ | C(CH$_3$)$_2$ | H | Cl |
| 1.155 | C$_2$H$_5$ | H | H | 0 | (CH$_2$)$_2$ | C=O | H | Cl |
| 1.156 | C$_2$H$_5$ | H | H | 2 | (CH$_2$)$_2$ | C=O | H | Cl |
| 1.157 | C$_2$H$_5$ | H | H | 0 | (CH$_2$)$_2$ | CHOCH$_3$ | H | Cl |
| 1.158 | C$_2$H$_5$ | H | H | 2 | (CH$_2$)$_2$ | CHOCH$_3$ | H | Cl |
| 1.159 | C$_2$H$_5$ | H | H | 0 | (CH$_2$)$_2$ | CHOC$_2$H$_5$ | H | Cl |
| 1.160 | C$_2$H$_5$ | H | H | 2 | (CH$_2$)$_2$ | CHOC$_2$H$_5$ | H | Cl |
| 1.161 | C$_2$H$_5$ | H | H | 0 | (CH$_2$)$_2$ | CHOiPr | H | Cl |
| 1.162 | C$_2$H$_5$ | H | H | 2 | (CH$_2$)$_2$ | CHOiPr | H | Cl |
| 1.163 | C$_2$H$_5$ | H | H | 0 | (CH$_2$)$_2$ | CHOH | H | Cl |
| 1.164 | C$_2$H$_5$ | H | H | 2 | (CH$_2$)$_2$ | CHOH | H | Cl |
| 1.165 | C$_2$H$_5$ | H | H | 0 | (CH$_2$)$_2$ | C=NOCH$_3$ | H | Cl |
| 1.166 | C$_2$H$_5$ | H | H | 2 | (CH$_2$)$_2$ | C=NOCH$_3$ | H | Cl |
| 1.167 | C$_2$H$_5$ | H | H | 0 | (CH$_2$)$_2$ | C=NOC$_2$H$_5$ | H | Cl |
| 1.168 | C$_2$H$_5$ | H | H | 2 | (CH$_2$)$_2$ | C=NOC$_2$H$_5$ | H | Cl |
| 1.169 | C$_2$H$_5$ | H | H | 0 | (CH$_2$)$_2$ | C=NOiPr | H | Cl |
| 1.170 | C$_2$H$_5$ | H | H | 2 | (CH$_2$)$_2$ | C=NOiPr | H | Cl |
| 1.171 | C$_2$H$_5$ | H | H | 0 | (CH$_2$)$_2$ | C=NOCH$_2$CH=CHCl | H | Cl |
| 1.172 | C$_2$H$_5$ | H | H | 2 | (CH$_2$)$_2$ | C=NOCH$_2$CH=CHCl | H | Cl |
| 1.173 | C$_2$H$_5$ | H | H | 0 | (CH$_2$)$_2$ | C=NOCH$_2$C$_6$H$_5$ | H | Cl |
| 1.174 | C$_2$H$_5$ | H | H | 2 | (CH$_2$)$_2$ | C=NOCH$_2$C$_6$H$_5$ | H | Cl |
| 1.175 | C$_2$H$_5$ | H | H | 0 | (CH$_2$)$_2$ | C(CH$_3$)$_2$ | H | Cl |
| 1.176 | C$_2$H$_5$ | H | H | 2 | (CH$_2$)$_2$ | C(CH$_3$)$_2$ | H | Cl |
| 1.177 | CH$_3$ | CH$_3$ | H | 0 | (CH$_2$)$_2$ | C=O | H | CH$_3$ |
| 1.178 | CH$_3$ | CH$_3$ | H | 2 | (CH$_2$)$_2$ | C=O | H | CH$_3$ |
| 1.179 | CH$_3$ | CH$_3$ | H | 0 | (CH$_2$)$_2$ | CHOCH$_3$ | H | CH$_3$ |
| 1.180 | CH$_3$ | CH$_3$ | H | 2 | (CH$_2$)$_2$ | CHOCH$_3$ | H | CH$_3$ |
| 1.181 | CH$_3$ | CH$_3$ | H | 0 | (CH$_2$)$_2$ | CHOC$_2$H$_5$ | H | CH$_3$ |
| 1.182 | CH$_3$ | CH$_3$ | H | 2 | (CH$_2$)$_2$ | CHOC$_2$H$_5$ | H | CH$_3$ |
| 1.183 | CH$_3$ | CH$_3$ | H | 0 | (CH$_2$)$_2$ | CHOiPr | H | CH$_3$ |
| 1.184 | CH$_3$ | CH$_3$ | H | 2 | (CH$_2$)$_2$ | CHOiPr | H | CH$_3$ |
| 1.185 | CH$_3$ | CH$_3$ | H | 0 | (CH$_2$)$_2$ | CHOH | H | CH$_3$ |
| 1.186 | CH$_3$ | CH$_3$ | H | 2 | (CH$_2$)$_2$ | CHOH | H | CH$_3$ |
| 1.187 | CH$_3$ | CH$_3$ | H | 0 | (CH$_2$)$_2$ | C=NOCH$_3$ | H | CH$_3$ |
| 1.188 | CH$_3$ | CH$_3$ | H | 2 | (CH$_2$)$_2$ | C=NOCH$_3$ | H | CH$_3$ |
| 1.189 | CH$_3$ | CH$_3$ | H | 0 | (CH$_2$)$_2$ | C=NOC$_2$H$_5$ | H | CH$_3$ |
| 1.190 | CH$_3$ | CH$_3$ | H | 2 | (CH$_2$)$_2$ | C=NOC$_2$H$_5$ | H | CH$_3$ |
| 1.191 | CH$_3$ | CH$_3$ | H | 0 | (CH$_2$)$_2$ | C=NOiPr | H | CH$_3$ |
| 1.192 | CH$_3$ | CH$_3$ | H | 2 | (CH$_2$)$_2$ | C=NOiPr | H | CH$_3$ |
| 1.193 | CH$_3$ | CH$_3$ | H | 0 | (CH$_2$)$_2$ | C=NOCH$_2$CH=CHCl | H | CH$_3$ |
| 1.194 | CH$_3$ | CH$_3$ | H | 2 | (CH$_2$)$_2$ | C=NOCH$_2$CH=CHCl | H | CH$_3$ |
| 1.195 | CH$_3$ | CH$_3$ | H | 0 | (CH$_2$)$_2$ | C=NOCH$_2$C$_6$H$_5$ | H | CH$_3$ |
| 1.196 | CH$_3$ | CH$_3$ | H | 2 | (CH$_2$)$_2$ | C=NOCH$_2$C$_6$H$_5$ | H | CH$_3$ |
| 1.197 | CH$_3$ | CH$_3$ | H | 0 | (CH$_2$)$_2$ | C(CH$_3$)$_2$ | H | CH$_3$ |
| 1.198 | CH$_3$ | CH$_3$ | H | 2 | (CH$_2$)$_2$ | C(CH$_3$)$_2$ | H | CH$_3$ |

TABLE 1-continued

Compounds of the formula

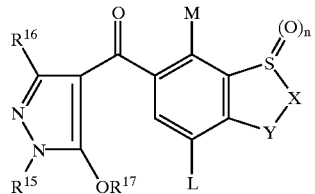

| No. | R15 | R16 | R17 | n | X | Y | L | M |
|---|---|---|---|---|---|---|---|---|
| 1.199 | $C_2H_5$ | H | H | 0 | $(CH_2)_2$ | C=O | H | $CH_3$ |
| 1.200 | $C_2H_5$ | H | H | 2 | $(CH_2)_2$ | C=O | H | $CH_3$ |
| 1.201 | $C_2H_5$ | H | H | 0 | $(CH_2)_2$ | $CHOCH_3$ | H | $CH_3$ |
| 1.202 | $C_2H_5$ | H | H | 2 | $(CH_2)_2$ | $CHOCH_3$ | H | $CH_3$ |
| 1.203 | $C_2H_5$ | H | H | 0 | $(CH_2)_2$ | $CHOC_2H_5$ | H | $CH_3$ |
| 1.204 | $C_2H_5$ | H | H | 2 | $(CH_2)_2$ | $CHOC_2H_5$ | H | $CH_3$ |
| 1.205 | $C_2H_5$ | H | H | 0 | $(CH_2)_2$ | CHOiPr | H | $CH_3$ |
| 1.206 | $C_2H_5$ | H | H | 2 | $(CH_2)_2$ | CHOiPr | H | $CH_3$ |
| 1.207 | $C_2H_5$ | H | H | 0 | $(CH_2)_2$ | CHOH | H | $CH_3$ |
| 1.208 | $C_2H_5$ | H | H | 2 | $(CH_2)_2$ | CHOH | H | $CH_3$ |
| 1.209 | $C_2H_5$ | H | H | 0 | $(CH_2)_2$ | $C=NOCH_3$ | H | $CH_3$ |
| 1.210 | $C_2H_5$ | H | H | 2 | $(CH_2)_2$ | $C=NOCH_3$ | H | $CH_3$ |
| 1.211 | $C_2H_5$ | H | H | 0 | $(CH_2)_2$ | $C=NOC_2H_5$ | H | $CH_3$ |
| 1.212 | $C_2H_5$ | H | H | 2 | $(CH_2)_2$ | $C=NOC_2H_5$ | H | $CH_3$ |
| 1.213 | $C_2H_5$ | H | H | 0 | $(CH_2)_2$ | C=NOiPr | H | $CH_3$ |
| 1.214 | $C_2H_5$ | H | H | 2 | $(CH_2)_2$ | C=NOiPr | H | $CH_3$ |
| 1.215 | $C_2H_5$ | H | H | 0 | $(CH_2)_2$ | $C=NOCH_2CH=CHCl$ | H | $CH_3$ |
| 1.216 | $C_2H_5$ | H | H | 2 | $(CH_2)_2$ | $C=NOCH_2CH=CHCl$ | H | $CH_3$ |
| 1.217 | $C_2H_5$ | H | H | 0 | $(CH_2)_2$ | $C=NOCH_2C_6H_5$ | H | $CH_3$ |
| 1.218 | $C_2H_5$ | H | H | 2 | $(CH_2)_2$ | $C=NOCH_2C_6H_5$ | H | $CH_3$ |
| 1.219 | $C_2H_5$ | H | H | 0 | $(CH_2)_2$ | $C(CH_3)_2$ | H | $CH_3$ |
| 1.220 | $C_2H_5$ | H | H | 2 | $(CH_2)_2$ | $C(CH_3)_2$ | H | $CH_3$ |
| 1.221 | $CH_3$ | $CH_3$ | p-$CH_3$—$C_6H_4$—$SO_2$— | 0 | $(CH_2)_2$ | C=O | H | $CH_3$ |
| 1.222 | $CH_3$ | $CH_3$ | p-$CH_3$—$C_6H_4$—$SO_2$— | 2 | $(CH_2)_2$ | C=O | H | $CH_3$ |
| 1.223 | $CH_3$ | $CH_3$ | p-$CH_3$—$C_6H_4$—$SO_2$— | 0 | $(CH_2)_2$ | $CHOCH_3$ | H | $CH_3$ |
| 1.224 | $CH_3$ | $CH_3$ | p-$CH_3$—$C_6H_4$—$SO_2$— | 2 | $(CH_2)_2$ | $CHOCH_3$ | H | $CH_3$ |
| 1.225 | $CH_3$ | $CH_3$ | p-$CH_3$—$C_6H_4$—$SO_2$— | 0 | $(CH_2)_2$ | $CHOC_2H_5$ | H | $CH_3$ |
| 1.226 | $CH_3$ | $CH_3$ | p-$CH_3$—$C_6H_4$—$SO_2$— | 2 | $(CH_2)_2$ | $CHOC_2H_5$ | H | $CH_3$ |
| 1.227 | $CH_3$ | $CH_3$ | p-$CH_3$—$C_6H_4$—$SO_2$— | 0 | $(CH_2)_2$ | CHOiPr | H | $CH_3$ |
| 1.228 | $CH_3$ | $CH_3$ | p-$CH_3$—$C_6H_4$—$SO_2$— | 2 | $(CH_2)_2$ | CHOiPr | H | $CH_3$ |
| 1.229 | $CH_3$ | $CH_3$ | p-$CH_3$—$C_6H_4$—$SO_2$— | 0 | $(CH_2)_2$ | CHOH | H | $CH_3$ |
| 1.230 | $CH_3$ | $CH_3$ | p-$CH_3$—$C_6H_4$—$SO_2$— | 2 | $(CH_2)_2$ | CHOH | H | $CH_3$ |
| 1.231 | $CH_3$ | $CH_3$ | p-$CH_3$—$C_6H_4$—$SO_2$— | 0 | $(CH_2)_2$ | $C=NOCH_3$ | H | $CH_3$ |
| 1.232 | $CH_3$ | $CH_3$ | p-$CH_3$—$C_6H_4$—$SO_2$— | 2 | $(CH_2)_2$ | $C=NOCH_3$ | H | $CH_3$ |
| 1.233 | $CH_3$ | $CH_3$ | p-$CH_3$—$C_6H_4$—$SO_2$— | 0 | $(CH_2)_2$ | $C=NOC_2H_5$ | H | $CH_3$ |
| 1.234 | $CH_3$ | $CH_3$ | p-$CH_3$—$C_6H_4$—$SO_2$— | 2 | $(CH_2)_2$ | $C=NOC_2H_5$ | H | $CH_3$ |
| 1.235 | $CH_3$ | $CH_3$ | p-$CH_3$—$C_6H_4$—$SO_2$— | 0 | $(CH_2)_2$ | C=NOiPr | H | $CH_3$ |
| 1.236 | $CH_3$ | $CH_3$ | p-$CH_3$—$C_6H_4$—$SO_2$— | 2 | $(CH_2)_2$ | C=NOiPr | H | $CH_3$ |
| 1.237 | $CH_3$ | $CH_3$ | p-$CH_3$—$C_6H_4$—$SO_2$— | 0 | $(CH_2)_2$ | $C=NOCH_2CH=CHCl$ | H | $CH_3$ |
| 1.238 | $CH_3$ | $CH_3$ | p-$CH_3$—$C_6H_4$—$SO_2$— | 2 | $(CH_2)_2$ | $C=NOCH_2CH=CHCl$ | H | $CH_3$ |
| 1.239 | $CH_3$ | $CH_3$ | p-$CH_3$—$C_6H_4$—$SO_2$— | 0 | $(CH_2)_2$ | $C=NOCH_2C_6H_5$ | H | $CH_3$ |
| 1.240 | $CH_3$ | $CH_3$ | p-$CH_3$—$C_6H_4$—$SO_2$— | 2 | $(CH_2)_2$ | $C=NOCH_2C_6H_5$ | H | $CH_3$ |
| 1.241 | $CH_3$ | $CH_3$ | p-$CH_3$—$C_6H_4$—$SO_2$— | 0 | $(CH_2)_2$ | $C(CH_3)_2$ | H | $CH_3$ |
| 1.242 | $CH_3$ | $CH_3$ | p-$CH_3$—$C_6H_4$—$SO_2$— | 2 | $(CH_2)_2$ | $C(CH_3)_2$ | H | $CH_3$ |
| 1.243 | $C_2H_5$ | H | p-$CH_3$—$C_6H_4$—$SO_2$— | 0 | $(CH_2)_2$ | C=O | H | $CH_3$ |
| 1.244 | $C_2H_5$ | H | p-$CH_3$—$C_6H_4$—$SO_2$— | 2 | $(CH_2)_2$ | C=O | H | $CH_3$ |
| 1.245 | $C_2H_5$ | H | p-$CH_3$—$C_6H_4$—$SO_2$— | 0 | $(CH_2)_2$ | $CHOCH_3$ | H | $CH_3$ |
| 1.246 | $C_2H_5$ | H | p-$CH_3$—$C_6H_4$—$SO_2$— | 2 | $(CH_2)_2$ | $CHOCH_3$ | H | $CH_3$ |
| 1.247 | $C_2H_5$ | H | p-$CH_3$—$C_6H_4$—$SO_2$— | 0 | $(CH_2)_2$ | $CHOC_2H_5$ | H | $CH_3$ |
| 1.248 | $C_2H_5$ | H | p-$CH_3$—$C_6H_4$—$SO_2$— | 2 | $(CH_2)_2$ | $CHOC_2H_5$ | H | $CH_3$ |
| 1.249 | $C_2H_5$ | H | p-$CH_3$—$C_6H_4$—$SO_2$— | 0 | $(CH_2)_2$ | CHOiPr | H | $CH_3$ |
| 1.250 | $C_2H_5$ | H | p-$CH_3$—$C_6H_4$—$SO_2$— | 2 | $(CH_2)_2$ | CHOiPr | H | $CH_3$ |
| 1.251 | $C_2H_5$ | H | p-$CH_3$—$C_6H_4$—$SO_2$— | 0 | $(CH_2)_2$ | CHOH | H | $CH_3$ |
| 1.252 | $C_2H_5$ | H | p-$CH_3$—$C_6H_4$—$SO_2$— | 2 | $(CH_2)_2$ | CHOH | H | $CH_3$ |
| 1.253 | $C_2H_5$ | H | p-$CH_3$—$C_6H_4$—$SO_2$— | 0 | $(CH_2)_2$ | $C=NOCH_3$ | H | $CH_3$ |
| 1.254 | $C_2H_5$ | H | p-$CH_3$—$C_6H_4$—$SO_2$— | 2 | $(CH_2)_2$ | $C=NOCH_3$ | H | $CH_3$ |
| 1.255 | $C_2H_5$ | H | p-$CH_3$—$C_6H_4$—$SO_2$— | 0 | $(CH_2)_2$ | $C=NOC_2H_5$ | H | $CH_3$ |
| 1.256 | $C_2H_5$ | H | p-$CH_3$—$C_6H_4$—$SO_2$— | 2 | $(CH_2)_2$ | $C=NOC_2H_5$ | H | $CH_3$ |
| 1.257 | $C_2H_5$ | H | p-$CH_3$—$C_6H_4$—$SO_2$— | 0 | $(CH_2)_2$ | C=NOiPr | H | $CH_3$ |
| 1.258 | $C_2H_5$ | H | p-$CH_3$—$C_6H_4$—$SO_2$— | 2 | $(CH_2)_2$ | C=NOiPr | H | $CH_3$ |
| 1.259 | $C_2H_5$ | H | p-$CH_3$—$C_6H_4$—$SO_2$— | 0 | $(CH_2)_2$ | $C=NOCH_2CH=CHCl$ | H | $CH_3$ |
| 1.260 | $C_2H_5$ | H | p-$CH_3$—$C_6H_4$—$SO_2$— | 2 | $(CH_2)_2$ | $C=NOCH_2CH=CHCl$ | H | $CH_3$ |
| 1.261 | $C_2H_5$ | H | p-$CH_3$—$C_6H_4$—$SO_2$— | 0 | $(CH_2)_2$ | $C=NOCH_2C_6H_5$ | H | $CH_3$ |

TABLE 1-continued

Compounds of the formula

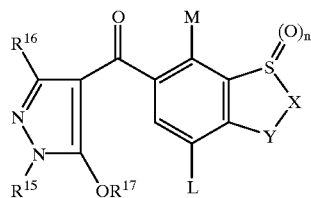

| No. | $R^{15}$ | $R^{16}$ | $R^{17}$ | n | X | Y | L | M |
|---|---|---|---|---|---|---|---|---|
| 1.262 | $C_2H_5$ | H | p-$CH_3$—$C_6H_4$—$SO_2$— | 2 | $(CH_2)_2$ | C=$NOCH_2C_6H_5$ | H | $CH_3$ |
| 1.263 | $C_2H_5$ | H | p-$CH_3$—$C_6H_4$—$SO_2$— | 0 | $(CH_2)_2$ | $C(CH_3)_2$ | H | $CH_3$ |
| 1.264 | $C_2H_5$ | H | p-$CH_3$—$C_6H_4$—$SO_2$— | 2 | $(CH_2)_2$ | $C(CH_3)_2$ | H | $CH_3$ |
| 1.265 | $CH_3$ | $CH_3$ | H | 0 | $CH_2$ | CH—$NHCH_3$ | H | H |
| 1.266 | $CH_3$ | $CH_3$ | H | 2 | $CH_2$ | CH—$NHCH_3$ | H | H |
| 1.267 | $CH_3$ | $CH_3$ | H | 0 | $CH_2$ | CH—$NHC_2H_5$ | H | H |
| 1.268 | $CH_3$ | $CH_3$ | H | 2 | $CH_2$ | CH—$NHC_2H_5$ | H | H |
| 1.269 | $CH_3$ | $CH_3$ | H | 0 | $CH_2$ | CH—$N(CH_3)_2$ | H | H |
| 1.270 | $CH_3$ | $CH_3$ | H | 2 | $CH_2$ | CH—$N(CH_3)_2$ | H | H |
| 1.271 | $CH_3$ | $CH_3$ | H | 0 | $CH_2$ | CH—$NHOC_2H_5$ | H | H |
| 1.272 | $CH_3$ | $CH_3$ | H | 2 | $CH_2$ | CH—$NHOC_2H_5$ | H | H |
| 1.273 | $CH_3$ | $CH_3$ | H | 0 | $CH_2$ | CH—$N(CH_3)OC_2H_5$ | H | H |
| 1.274 | $CH_3$ | $CH_3$ | H | 2 | $CH_2$ | CH—$N(CH_3)OC_2H_5$ | H | H |
| 1.275 | $CH_3$ | $CH_3$ | H | 0 | $CH_2$ | C=N—$NH_2$ | H | H |
| 1.276 | $CH_3$ | $CH_3$ | H | 2 | $CH_2$ | C=N—$NH_2$ | H | H |
| 1.277 | $CH_3$ | $CH_3$ | H | 0 | $CH_2$ | C=N—$N(CH_3)_2$ | H | H |
| 1.278 | $CH_3$ | $CH_3$ | H | 2 | $CH_2$ | C=N—$N(CH_3)_2$ | H | H |
| 1.279 | $CH_3$ | $CH_3$ | H | 0 | $CH_2$ | $C(CH_3)$—$OCH_3$ | H | H |
| 1.280 | $CH_3$ | $CH_3$ | H | 2 | $CH_2$ | $C(CH_3)$—$OCH_3$ | H | H |
| 1.281 | $CH_3$ | $CH_3$ | H | 0 | $CH_2$ | O | H | H |
| 1.282 | $CH_3$ | $CH_3$ | H | 2 | $CH_2$ | O | H | H |
| 1.283 | $C_2H_5$ | H | H | 0 | $CH_2$ | CH—$NHCH_3$ | H | H |
| 1.284 | $C_2H_5$ | H | H | 2 | $CH_2$ | CH—$NHCH_3$ | H | H |
| 1.285 | $C_2H_5$ | H | H | 0 | $CH_2$ | CH—$NHC_2H_5$ | H | H |
| 1.286 | $C_2H_5$ | H | H | 2 | $CH_2$ | CH—$NHC_2H_5$ | H | H |
| 1.287 | $C_2H_5$ | H | H | 0 | $CH_2$ | CH—$N(CH_3)_2$ | H | H |
| 1.288 | $C_2H_5$ | H | H | 2 | $CH_2$ | CH—$N(CH_3)_2$ | H | H |
| 1.289 | $C_2H_5$ | H | H | 0 | $CH_2$ | CH—$NHOC_2H_5$ | H | H |
| 1.290 | $C_2H_5$ | H | H | 2 | $CH_2$ | CH—$NHOC_2H_5$ | H | H |
| 1.291 | $C_2H_5$ | H | H | 0 | $CH_2$ | CH—$N(CH_3)OC_2H_5$ | H | H |
| 1.292 | $C_2H_5$ | H | H | 2 | $CH_2$ | CH—$N(CH_3)OC_2H_5$ | H | H |
| 1.293 | $C_2H_5$ | H | H | 0 | $CH_2$ | C=N—$NH_2$ | H | H |
| 1.294 | $C_2H_5$ | H | H | 2 | $CH_2$ | C=N—$NH_2$ | H | H |
| 1.295 | $C_2H_5$ | H | H | 0 | $CH_2$ | C=N—$N(CH_3)_2$ | H | H |
| 1.296 | $C_2H_5$ | H | H | 2 | $CH_2$ | C=N—$N(CH_3)_2$ | H | H |
| 1.297 | $C_2H_5$ | H | H | 0 | $CH_2$ | $C(CH_3)$—$OCH_3$ | H | H |
| 1.298 | $C_2H_5$ | H | H | 2 | $CH_2$ | $C(CH_3)$—$OCH_3$ | H | H |
| 1.299 | $C_2H_5$ | H | H | 0 | $CH_2$ | O | H | H |
| 1.300 | $C_2H_5$ | H | H | 2 | $CH_2$ | O | H | H |
| 1.301 | $CH_3$ | $CH_3$ | H | 0 | $CH_2$ | CH—$NHCH_3$ | H | $CH_3$ |
| 1.302 | $CH_3$ | $CH_3$ | H | 2 | $CH_2$ | CH—$NHCH_3$ | H | $CH_3$ |
| 1.303 | $CH_3$ | $CH_3$ | H | 0 | $CH_2$ | CH—$NHC_2H_5$ | H | $CH_3$ |
| 1.304 | $CH_3$ | $CH_3$ | H | 2 | $CH_2$ | CH—$NHC_2H_5$ | H | $CH_3$ |
| 1.305 | $CH_3$ | $CH_3$ | H | 0 | $CH_2$ | CH—$N(CH_3)_2$ | H | $CH_3$ |
| 1.306 | $CH_3$ | $CH_3$ | H | 2 | $CH_2$ | CH—$N(CH_3)_2$ | H | $CH_3$ |
| 1.307 | $CH_3$ | $CH_3$ | H | 0 | $CH_2$ | CH—$NHOC_2H_5$ | H | $CH_3$ |
| 1.308 | $CH_3$ | $CH_3$ | H | 2 | $CH_2$ | CH—$NHOC_2H_5$ | H | $CH_3$ |
| 1.309 | $CH_3$ | $CH_3$ | H | 0 | $CH_2$ | CH—$N(CH_3)OC_2H_5$ | H | $CH_3$ |
| 1.310 | $CH_3$ | $CH_3$ | H | 2 | $CH_2$ | CH—$N(CH_3)OC_2H_5$ | H | $CH_3$ |
| 1.311 | $CH_3$ | $CH_3$ | H | 0 | $CH_2$ | C=N—$NH_2$ | H | $CH_3$ |
| 1.312 | $CH_3$ | $CH_3$ | H | 2 | $CH_2$ | C=N—$NH_2$ | H | $CH_3$ |
| 1.313 | $CH_3$ | $CH_3$ | H | 0 | $CH_2$ | C=N—$N(CH_3)_2$ | H | $CH_3$ |
| 1.314 | $CH_3$ | $CH_3$ | H | 2 | $CH_2$ | C=N—$N(CH_3)_2$ | H | $CH_3$ |
| 1.315 | $CH_3$ | $CH_3$ | H | 0 | $CH_2$ | $C(CH_3)$—$OCH_3$ | H | $CH_3$ |
| 1.316 | $CH_3$ | $CH_3$ | H | 2 | $CH_2$ | $C(CH_3)$—$OCH_3$ | H | $CH_3$ |
| 1.317 | $CH_3$ | $CH_3$ | H | 0 | $CH_2$ | O | H | $CH_3$ |
| 1.318 | $CH_3$ | $CH_3$ | H | 2 | $CH_2$ | O | H | $CH_3$ |
| 1.319 | $C_2H_5$ | H | H | 0 | $CH_2$ | CH—$NHCH_3$ | H | $CH_3$ |
| 1.320 | $C_2H_5$ | H | H | 2 | $CH_2$ | CH—$NHCH_3$ | H | $CH_3$ |
| 1.321 | $C_2H_5$ | H | H | 0 | $CH_2$ | CH—$NHC_2H_5$ | H | $CH_3$ |
| 1.322 | $C_2H_5$ | H | H | 2 | $CH_2$ | CH—$NHC_2H_5$ | H | $CH_3$ |
| 1.323 | $C_2H_5$ | H | H | 0 | $CH_2$ | CH—$N(CH_3)_2$ | H | $CH_3$ |
| 1.324 | $C_2H_5$ | H | H | 2 | $CH_2$ | CH—$N(CH_3)_2$ | H | $CH_3$ |

TABLE 1-continued

Compounds of the formula

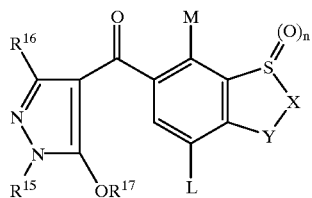

| No. | R¹⁵ | R¹⁶ | R¹⁷ | n | X | Y | L | M |
|---|---|---|---|---|---|---|---|---|
| 1.325 | $C_2H_5$ | H | H | 0 | $CH_2$ | CH—$NHOC_2H_5$ | H | $CH_3$ |
| 1.326 | $C_2H_5$ | H | H | 2 | $CH_2$ | CH—$NHOC_2H_5$ | H | $CH_3$ |
| 1.327 | $C_2H_5$ | H | H | 0 | $CH_2$ | CH—$N(CH_3)OC_2H_5$ | H | $CH_3$ |
| 1.328 | $C_2H_5$ | H | H | 2 | $CH_2$ | CH—$N(CH_3)OC_2H_5$ | H | $CH_3$ |
| 1.329 | $C_2H_5$ | H | H | 0 | $CH_2$ | C=N—$NH_2$ | H | $CH_3$ |
| 1.330 | $C_2H_5$ | H | H | 2 | $CH_2$ | C=N—$NH_2$ | H | $CH_3$ |
| 1.331 | $C_2H_5$ | H | H | 0 | $CH_2$ | C=N—$N(CH_3)_2$ | H | $CH_3$ |
| 1.332 | $C_2H_5$ | H | H | 2 | $CH_2$ | C=N—$N(CH_3)_2$ | H | $CH_3$ |
| 1.333 | $C_2H_5$ | H | H | 0 | $CH_2$ | $C(CH_3)$—$OCH_3$ | H | $CH_3$ |
| 1.334 | $C_2H_5$ | H | H | 2 | $CH_2$ | $C(CH_3)$—$OCH_3$ | H | $CH_3$ |
| 1.335 | $C_2H_5$ | H | H | 0 | $CH_2$ | O | H | $CH_3$ |
| 1.336 | $C_2H_5$ | H | H | 2 | $CH_2$ | O | H | $CH_3$ |
| 1.337 | $CH_3$ | $CH_3$ | H | 0 | $CH_2$ | CH—$NHCH_3$ | H | Cl |
| 1.338 | $CH_3$ | $CH_3$ | H | 2 | $CH_2$ | CH—$NHCH_3$ | H | Cl |
| 1.339 | $CH_3$ | $CH_3$ | H | 0 | $CH_2$ | CH—$NHC_2H_5$ | H | Cl |
| 1.340 | $CH_3$ | $CH_3$ | H | 2 | $CH_2$ | CH—$NHC_2H_5$ | H | Cl |
| 1.341 | $CH_3$ | $CH_3$ | H | 0 | $CH_2$ | CH—$N(CH_3)_2$ | H | Cl |
| 1.342 | $CH_3$ | $CH_3$ | H | 2 | $CH_2$ | CH—$N(CH_3)_2$ | H | Cl |
| 1.343 | $CH_3$ | $CH_3$ | H | 0 | $CH_2$ | CH—$NHOC_2H_5$ | H | Cl |
| 1.344 | $CH_3$ | $CH_3$ | H | 2 | $CH_2$ | CH—$NHOC_2H_5$ | H | Cl |
| 1.345 | $CH_3$ | $CH_3$ | H | 0 | $CH_2$ | CH—$N(CH_3)OC_2H_5$ | H | Cl |
| 1.346 | $CH_3$ | $CH_3$ | H | 2 | $CH_2$ | CH—$N(CH_3)OC_2H_5$ | H | Cl |
| 1.347 | $CH_3$ | $CH_3$ | H | 0 | $CH_2$ | C=N—$NH_2$ | H | Cl |
| 1.348 | $CH_3$ | $CH_3$ | H | 2 | $CH_2$ | C=N—$NH_2$ | H | Cl |
| 1.349 | $CH_3$ | $CH_3$ | H | 0 | $CH_2$ | C=N—$N(CH_3)_2$ | H | Cl |
| 1.350 | $CH_3$ | $CH_3$ | H | 2 | $CH_2$ | C=N—$N(CH_3)_2$ | H | Cl |
| 1.351 | $CH_3$ | $CH_3$ | H | 0 | $CH_2$ | $C(CH_3)$—$OCH_3$ | H | Cl |
| 1.352 | $CH_3$ | $CH_3$ | H | 2 | $CH_2$ | $C(CH_3)$—$OCH_3$ | H | Cl |
| 1.353 | $CH_3$ | $CH_3$ | H | 0 | $CH_2$ | O | H | Cl |
| 1.354 | $CH_3$ | $CH_3$ | H | 2 | $CH_2$ | O | H | Cl |
| 1.355 | $C_2H_5$ | H | H | 0 | $CH_2$ | CH—$NHCH_3$ | H | Cl |
| 1.356 | $C_2H_5$ | H | H | 2 | $CH_2$ | CH—$NHCH_3$ | H | Cl |
| 1.357 | $C_2H_5$ | H | H | 0 | $CH_2$ | CH—$NHC_2H_5$ | H | Cl |
| 1.358 | $C_2H_5$ | H | H | 2 | $CH_2$ | CH—$NHC_2H_5$ | H | Cl |
| 1.359 | $C_2H_5$ | H | H | 0 | $CH_2$ | CH—$N(CH_3)_2$ | H | Cl |
| 1.360 | $C_2H_5$ | H | H | 2 | $CH_2$ | CH—$N(CH_3)_2$ | H | Cl |
| 1.361 | $C_2H_5$ | H | H | 0 | $CH_2$ | CH—$NHOC_2H_5$ | H | Cl |
| 1.362 | $C_2H_5$ | H | H | 2 | $CH_2$ | CH—$NHOC_2H_5$ | H | Cl |
| 1.363 | $C_2H_5$ | H | H | 0 | $CH_2$ | CH—$N(CH_3)OC_2H_5$ | H | Cl |
| 1.364 | $C_2H_5$ | H | H | 2 | $CH_2$ | CH—$N(CH_3)OC_2H_5$ | H | Cl |
| 1.365 | $C_2H_5$ | H | H | 0 | $CH_2$ | C=N—$NH_2$ | H | Cl |
| 1.366 | $C_2H_5$ | H | H | 2 | $CH_2$ | C=N—$NH_2$ | H | Cl |
| 1.367 | $C_2H_5$ | H | H | 0 | $CH_2$ | C=N—$N(CH_3)_2$ | H | Cl |
| 1.368 | $C_2H_5$ | H | H | 2 | $CH_2$ | C=N—$N(CH_3)_2$ | H | Cl |
| 1.369 | $C_2H_5$ | H | H | 0 | $CH_2$ | $C(CH_3)$—$OCH_3$ | H | Cl |
| 1.370 | $C_2H_5$ | H | H | 2 | $CH_2$ | $C(CH_3)$—$OCH_3$ | H | Cl |
| 1.371 | $C_2H_5$ | H | H | 0 | $CH_2$ | O | H | Cl |
| 1.372 | $C_2H_5$ | H | H | 2 | $CH_2$ | O | H | Cl |
| 1.373 | $CH_3$ | $CH_3$ | H | 0 | $(CH_2)_2$ | CH—$NHCH_3$ | H | H |
| 1.374 | $CH_3$ | $CH_3$ | H | 2 | $(CH_2)_2$ | CH—$NHCH_3$ | H | H |
| 1.375 | $CH_3$ | $CH_3$ | H | 0 | $(CH_2)_2$ | CH—$NHC_2H_5$ | H | H |
| 1.376 | $CH_3$ | $CH_3$ | H | 2 | $(CH_2)_2$ | CH—$NHC_2H_5$ | H | H |
| 1.377 | $CH_3$ | $CH_3$ | H | 0 | $(CH_2)_2$ | CH—$N(CH_3)_2$ | H | H |
| 1.378 | $CH_3$ | $CH_3$ | H | 2 | $(CH_2)_2$ | CH—$N(CH_3)_2$ | H | H |
| 1.379 | $CH_3$ | $CH_3$ | H | 0 | $(CH_2)_2$ | CH—$NHOC_2H_5$ | H | H |
| 1.380 | $CH_3$ | $CH_3$ | H | 2 | $(CH_2)_2$ | CH—$NHOC_2H_5$ | H | H |
| 1.381 | $CH_3$ | $CH_3$ | H | 0 | $(CH_2)_2$ | CH—$N(CH_3)OC_2H_5$ | H | H |
| 1.382 | $CH_3$ | $CH_3$ | H | 2 | $(CH_2)_2$ | CH—$N(CH_3)OC_2H_5$ | H | H |
| 1.383 | $CH_3$ | $CH_3$ | H | 0 | $(CH_2)_2$ | C=N—$NH_2$ | H | H |
| 1.384 | $CH_3$ | $CH_3$ | H | 2 | $(CH_2)_2$ | C=N—$NH_2$ | H | H |
| 1.385 | $CH_3$ | $CH_3$ | H | 0 | $(CH_2)_2$ | C=N—$N(CH_3)_2$ | H | H |
| 1.386 | $CH_3$ | $CH_3$ | H | 2 | $(CH_2)_2$ | C=N—$N(CH_3)_2$ | H | H |
| 1.387 | $CH_3$ | $CH_3$ | H | 0 | $(CH_2)_2$ | $C(CH_3)$—$OCH_3$ | H | H |

TABLE 1-continued

Compounds of the formula

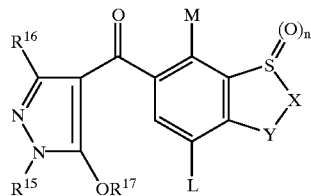

| No. | $R^{15}$ | $R^{16}$ | $R^{17}$ | n | X | Y | L | M |
|---|---|---|---|---|---|---|---|---|
| 1.388 | $CH_3$ | $CH_3$ | H | 2 | $(CH_2)_2$ | $C(CH_3)$—$OCH_3$ | H | H |
| 1.389 | $CH_3$ | $CH_3$ | H | 0 | $(CH_2)_2$ | O | H | H |
| 1.390 | $CH_3$ | $CH_3$ | H | 2 | $(CH_2)_2$ | O | H | H |
| 1.391 | $C_2H_5$ | H | H | 0 | $(CH_2)_2$ | CH—$NHCH_3$ | H | H |
| 1.392 | $C_2H_5$ | H | H | 2 | $(CH_2)_2$ | CH—$NHCH_3$ | H | H |
| 1.393 | $C_2H_5$ | H | H | 0 | $(CH_2)_2$ | CH—$NHC_2H_5$ | H | H |
| 1.394 | $C_2H_5$ | H | H | 2 | $(CH_2)_2$ | CH—$NHC_2H_5$ | H | H |
| 1.395 | $C_2H_5$ | H | H | 0 | $(CH_2)_2$ | CH—$N(CH_3)_2$ | H | H |
| 1.396 | $C_2H_5$ | H | H | 2 | $(CH_2)_2$ | CH—$N(CH_3)_2$ | H | H |
| 1.397 | $C_2H_5$ | H | H | 0 | $(CH_2)_2$ | CH—$NHOC_2H_5$ | H | H |
| 1.398 | $C_2H_5$ | H | H | 2 | $(CH_2)_2$ | CH—$NHOC_2H_5$ | H | H |
| 1.399 | $C_2H_5$ | H | H | 0 | $(CH_2)_2$ | CH—$N(CH_3)OC_2H_5$ | H | H |
| 1.400 | $C_2H_5$ | H | H | 2 | $(CH_2)_2$ | CH—$N(CH_3)OC_2H_5$ | H | H |
| 1.401 | $C_2H_5$ | H | H | 0 | $(CH_2)_2$ | C=N—$NH_2$ | H | H |
| 1.402 | $C_2H_5$ | H | H | 2 | $(CH_2)_2$ | C=N—$NH_2$ | H | H |
| 1.403 | $C_2H_5$ | H | H | 0 | $(CH_2)_2$ | C=N—$N(CH_3)_2$ | H | H |
| 1.404 | $C_2H_5$ | H | H | 2 | $(CH_2)_2$ | C=N—$N(CH_3)_2$ | H | H |
| 1.405 | $C_2H_5$ | H | H | 0 | $(CH_2)_2$ | $C(CH_3)$—$OCH_3$ | H | H |
| 1.406 | $C_2H_5$ | H | H | 2 | $(CH_2)_2$ | $C(CH_3)$—$OCH_3$ | H | H |
| 1.407 | $C_2H_5$ | H | H | 0 | $(CH_2)_2$ | O | H | H |
| 1.408 | $C_2H_5$ | H | H | 2 | $(CH_2)_2$ | O | H | H |
| 1.409 | $CH_3$ | $CH_3$ | H | 0 | $(CH_2)_2$ | CH—$NHCH_3$ | H | $CH_3$ |
| 1.410 | $CH_3$ | $CH_3$ | H | 2 | $(CH_2)_2$ | CH—$NHCH_3$ | H | $CH_3$ |
| 1.411 | $CH_3$ | $CH_3$ | H | 0 | $(CH_2)_2$ | CH—$NHC_2H_5$ | H | $CH_3$ |
| 1.412 | $CH_3$ | $CH_3$ | H | 2 | $(CH_2)_2$ | CH—$NHC_2H_5$ | H | $CH_3$ |
| 1.413 | $CH_3$ | $CH_3$ | H | 0 | $(CH_2)_2$ | CH—$N(CH_3)_2$ | H | $CH_3$ |
| 1.414 | $CH_3$ | $CH_3$ | H | 2 | $(CH_2)_2$ | CH—$N(CH_3)_2$ | H | $CH_3$ |
| 1.415 | $CH_3$ | $CH_3$ | H | 0 | $(CH_2)_2$ | CH—$NHOC_2H_5$ | H | $CH_3$ |
| 1.416 | $CH_3$ | $CH_3$ | H | 2 | $(CH_2)_2$ | CH—$NHOC_2H_5$ | H | $CH_3$ |
| 1.417 | $CH_3$ | $CH_3$ | H | 0 | $(CH_2)_2$ | CH—$N(CH_3)OC_2H_5$ | H | $CH_3$ |
| 1.418 | $CH_3$ | $CH_3$ | H | 2 | $(CH_2)_2$ | CH—$N(CH_3)OC_2H_5$ | H | $CH_3$ |
| 1.419 | $CH_3$ | $CH_3$ | H | 0 | $(CH_2)_2$ | C=N—$NH_2$ | H | $CH_3$ |
| 1.420 | $CH_3$ | $CH_3$ | H | 2 | $(CH_2)_2$ | C=N—$NH_2$ | H | $CH_3$ |
| 1.421 | $CH_3$ | $CH_3$ | H | 0 | $(CH_2)_2$ | C=N—$N(CH_3)_2$ | H | $CH_3$ |
| 1.422 | $CH_3$ | $CH_3$ | H | 2 | $(CH_2)_2$ | C=N—$N(CH_3)_2$ | H | $CH_3$ |
| 1.423 | $CH_3$ | $CH_3$ | H | 0 | $(CH_2)_2$ | $C(CH_3)$—$OCH_3$ | H | $CH_3$ |
| 1.424 | $CH_3$ | $CH_3$ | H | 2 | $(CH_2)_2$ | $C(CH_3)$—$OCH_3$ | H | $CH_3$ |
| 1.425 | $CH_3$ | $CH_3$ | H | 0 | $(CH_2)_2$ | O | H | $CH_3$ |
| 1.426 | $CH_3$ | $CH_3$ | H | 2 | $(CH_2)_2$ | O | H | $CH_3$ |
| 1.427 | $C_2H_5$ | H | H | 0 | $(CH_2)_2$ | CH—$NHCH_3$ | H | $CH_3$ |
| 1.428 | $C_2H_5$ | H | H | 2 | $(CH_2)_2$ | CH—$NHCH_3$ | H | $CH_3$ |
| 1.429 | $C_2H_5$ | H | H | 0 | $(CH_2)_2$ | CH—$NHC_2H_5$ | H | CH3. |
| 1.430 | $C_2H_5$ | H | H | 2 | $(CH_2)_2$ | CH—$NHC_2H_5$ | H | $CH_3$ |
| 1.431 | $C_2H_5$ | H | H | 0 | $(CH_2)_2$ | CH—$N(CH_3)_2$ | H | $CH_3$ |
| 1.432 | $C_2H_5$ | H | H | 2 | $(CH_2)_2$ | CH—$N(CH_3)_2$ | H | $CH_3$ |
| 1.433 | $C_2H_5$ | H | H | 0 | $(CH_2)_2$ | CH—$NHOC_2H_5$ | H | $CH_3$ |
| 1.434 | $C_2H_5$ | H | H | 2 | $(CH_2)_2$ | CH—$NHOC_2H_5$ | H | $CH_3$ |
| 1.435 | $C_2H_5$ | H | H | 0 | $(CH_2)_2$ | CH—$N(CH_3)OC_2H_5$ | H | $CH_3$ |
| 1.436 | $C_2H_5$ | H | H | 2 | $(CH_2)_2$ | CH—$N(CH_3)OC_2H_5$ | H | $CH_3$ |
| 1.437 | $C_2H_5$ | H | H | 0 | $(CH_2)_2$ | C=N—$NH_2$ | H | $CH_3$ |
| 1.438 | $C_2H_5$ | H | H | 2 | $(CH_2)_2$ | C=N—$NH_2$ | H | $CH_3$ |
| 1.439 | $C_2H_5$ | H | H | 0 | $(CH_2)_2$ | C=N—$N(CH_3)_2$ | H | $CH_3$ |
| 1.440 | $C_2H_5$ | H | H | 2 | $(CH_2)_2$ | C=N—$N(CH_3)_2$ | H | $CH_3$ |
| 1.441 | $C_2H_5$ | H | H | 0 | $(CH_2)_2$ | $C(CH_3)$—$OCH_3$ | H | $CH_3$ |
| 1.442 | $C_2H_5$ | H | H | 2 | $(CH_2)_2$ | $C(CH_3)$—$OCH_3$ | H | $CH_3$ |
| 1.443 | $C_2H_5$ | H | H | 0 | $(CH_2)_2$ | O | H | $CH_3$ |
| 1.444 | $C_2H_5$ | H | H | 2 | $(CH_2)_2$ | O | H | $CH_3$ |
| 1.445 | $CH_3$ | $CH_3$ | H | 0 | $(CH_2)_2$ | CH—$NHCH_3$ | H | Cl |
| 1.446 | $CH_3$ | $CH_3$ | H | 2 | $(CH_2)_2$ | CH—$NHCH_3$ | H | Cl |
| 1.447 | $CH_3$ | $CH_3$ | H | 0 | $(CH_2)_2$ | CH—$NHC_2H_5$ | H | Cl |
| 1.448 | $CH_3$ | $CH_3$ | H | 2 | $(CH_2)_2$ | CH—$NHC_2H_5$ | H | Cl |
| 1.449 | $CH_3$ | $CH_3$ | H | 0 | $(CH_2)_2$ | CH—$N(CH_3)_2$ | H | Cl |
| 1.450 | $CH_3$ | $CH_3$ | H | 2 | $(CH_2)_2$ | CH—$N(CH_3)_2$ | H | Cl |

TABLE 1-continued

Compounds of the formula

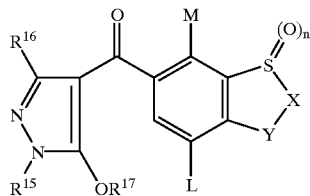

| No. | $R^{15}$ | $R^{16}$ | $R^{17}$ | n | X | Y | L | M |
|---|---|---|---|---|---|---|---|---|
| 1.451 | $CH_3$ | $CH_3$ | H | 0 | $(CH_2)_2$ | CH—$NHOC_2H_5$ | H | Cl |
| 1.452 | $CH_3$ | $CH_3$ | H | 2 | $(CH_2)_2$ | CH—$NHOC_2H_5$ | H | Cl |
| 1.453 | $CH_3$ | $CH_3$ | H | 0 | $(CH_2)_2$ | CH—$N(CH_3)OC_2H_5$ | H | Cl |
| 1.454 | $CH_3$ | $CH_3$ | H | 2 | $(CH_2)_2$ | CH—$N(CH_3)OC_2H_5$ | H | Cl |
| 1.455 | $CH_3$ | $CH_3$ | H | 0 | $(CH_2)_2$ | C=N—$NH_2$ | H | Cl |
| 1.456 | $CH_3$ | $CH_3$ | H | 2 | $(CH_2)_2$ | C=N—$NH_2$ | H | Cl |
| 1.457 | $CH_3$ | $CH_3$ | H | 0 | $(CH_2)_2$ | C=N—$N(CH_3)_2$ | H | Cl |
| 1.458 | $CH_3$ | $CH_3$ | H | 2 | $(CH_2)_2$ | C=N—$N(CH_3)_2$ | H | Cl |
| 1.459 | $CH_3$ | $CH_3$ | H | 0 | $(CH_2)_2$ | $C(CH_3)$—$OCH_3$ | H | Cl |
| 1.460 | $CH_3$ | $CH_3$ | H | 2 | $(CH_2)_2$ | $C(CH_3)$—$OCH_3$ | H | Cl |
| 1.461 | $CH_3$ | $CH_3$ | H | 0 | $(CH_2)_2$ | O | H | Cl |
| 1.462 | $CH_3$ | $CH_3$ | H | 2 | $(CH_2)_2$ | O | H | Cl |
| 1.463 | $C_2H_5$ | H | H | 0 | $(CH_2)_2$ | CH—$NHCH_3$ | H | Cl |
| 1.464 | $C_2H_5$ | H | H | 2 | $(CH_2)_2$ | CH—$NHCH_3$ | H | Cl |
| 1.465 | $C_2H_5$ | H | H | 0 | $(CH_2)_2$ | CH—$NHC_2H_5$ | H | Cl |
| 1.466 | $C_2H_5$ | H | H | 2 | $(CH_2)_2$ | CH—$NHC_2H_5$ | H | Cl |
| 1.467 | $C_2H_5$ | H | H | 0 | $(CH_2)_2$ | CH—$N(CH_3)_2$ | H | Cl |
| 1.468 | $C_2H_5$ | H | H | 2 | $(CH_2)_2$ | CH—$N(CH_3)_2$ | H | Cl |
| 1.469 | $C_2H_5$ | H | H | 0 | $(CH_2)_2$ | CH—$NHOC_2H_5$ | H | Cl |
| 1.470 | $C_2H_5$ | H | H | 2 | $(CH_2)_2$ | CH—$NHOC_2H_5$ | H | Cl |
| 1.471 | $C_2H_5$ | H | H | 0 | $(CH_2)_2$ | CH—$N(CH_3)OC_2H_5$ | H | Cl |
| 1.472 | $C_2H_5$ | H | H | 2 | $(CH_2)_2$ | CH—$N(CH_3)OC_2H_5$ | H | Cl |
| 1.473 | $C_2H_5$ | H | H | 0 | $(CH_2)_2$ | C=N—$NH_2$ | H | Cl |
| 1.474 | $C_2H_5$ | H | H | 2 | $(CH_2)_2$ | C=N—$NH_2$ | H | Cl |
| 1.475 | $C_2H_5$ | H | H | 0 | $(CH_2)_2$ | C=N—$N(CH_3)_2$ | H | Cl |
| 1.476 | $C_2H_5$ | H | H | 2 | $(CH_2)_2$ | C=N—$N(CH_3)_2$ | H | Cl |
| 1.477 | $C_2H_5$ | H | H | 0 | $(CH_2)_2$ | $C(CH_3)$—$OCH_3$ | H | Cl |
| 1.478 | $C_2H_5$ | H | H | 2 | $(CH_2)_2$ | $C(CH_3)$—$OCH_3$ | H | Cl |
| 1.479 | $C_2H_5$ | H | H | 0 | $(CH_2)_2$ | O | H | Cl |
| 1.480 | $C_2H_5$ | H | H | 2 | $(CH_2)_2$ | O | H | Cl |
| 1.481 | $CH_3$ | $CH_3$ | H | 0 | $(CH_2)_2$ | CH—$NHCH_3$ | $CH_3$ | $CH_3$ |
| 1.482 | $CH_3$ | $CH_3$ | H | 2 | $(CH_2)_2$ | CH—$NHCH_3$ | $CH_3$ | $CH_3$ |
| 1.483 | $CH_3$ | $CH_3$ | H | 0 | $(CH_2)_2$ | CH—$NHC_2H_5$ | $CH_3$ | $CH_3$ |
| 1.484 | $CH_3$ | $CH_3$ | H | 2 | $(CH_2)_2$ | CH—$NHC_2H_5$ | $CH_3$ | $CH_3$ |
| 1.485 | $CH_3$ | $CH_3$ | H | 0 | $(CH_2)_2$ | CH—$N(CH_3)_2$ | $CH_3$ | $CH_3$ |
| 1.486 | $CH_3$ | $CH_3$ | H | 2 | $(CH_2)_2$ | CH—$N(CH_3)_2$ | $CH_3$ | $CH_3$ |
| 1.487 | $CH_3$ | $CH_3$ | H | 0 | $(CH_2)_2$ | CH—$NHOC_2H_5$ | $CH_3$ | $CH_3$ |
| 1.488 | $CH_3$ | $CH_3$ | H | 2 | $(CH_2)_2$ | CH—$NHOC_2H_5$ | $CH_3$ | $CH_3$ |
| 1.489 | $CH_3$ | $CH_3$ | H | 0 | $(CH_2)_2$ | CH—$N(CH_3)OC_2H_5$ | $CH_3$ | $CH_3$ |
| 1.490 | $CH_3$ | $CH_3$ | H | 2 | $(CH_2)_2$ | CH—$N(CH_3)OC_2H_5$ | $CH_3$ | $CH_3$ |
| 1.491 | $CH_3$ | $CH_3$ | H | 0 | $(CH_2)_2$ | C=N—$NH_2$ | $CH_3$ | $CH_3$ |
| 1.492 | $CH_3$ | $CH_3$ | H | 2 | $(CH_2)_2$ | C=N—$NH_2$ | $CH_3$ | $CH_3$ |
| 1.493 | $CH_3$ | $CH_3$ | H | 0 | $(CH_2)_2$ | C=N—$N(CH_3)_2$ | $CH_3$ | $CH_3$ |
| 1.494 | $CH_3$ | $CH_3$ | H | 2 | $(CH_2)_2$ | C=N—$N(CH_3)_2$ | $CH_3$ | $CH_3$ |
| 1.495 | $CH_3$ | $CH_3$ | H | 0 | $(CH_2)_2$ | $C(CH_3)$—$OCH_3$ | $CH_3$ | $CH_3$ |
| 1.496 | $CH_3$ | $CH_3$ | H | 2 | $(CH_2)_2$ | $C(CH_3)$—$OCH_3$ | $CH_3$ | $CH_3$ |
| 1.497 | $CH_3$ | $CH_3$ | H | 0 | $(CH_2)_2$ | O | $CH_3$ | $CH_3$ |
| 1.498 | $CH_3$ | $CH_3$ | H | 2 | $(CH_2)_2$ | O | $CH_3$ | $CH_3$ |
| 1.499 | $C_2H_5$ | H | H | 0 | $(CH_2)_2$ | CH—$NHCH_3$ | $CH_3$ | $CH_3$ |
| 1.500 | $C_2H_5$ | H | H | 2 | $(CH_2)_2$ | CH—$NHCH_3$ | $CH_3$ | $CH_3$ |
| 1.501 | $C_2H_5$ | H | H | 0 | $(CH_2)_2$ | CH—$NHC_2H_5$ | $CH_3$ | $CH_3$ |
| 1.502 | $C_2H_5$ | H | H | 2 | $(CH_2)_2$ | CH—$NHC_2H_5$ | $CH_3$ | $CH_3$ |
| 1.503 | $C_2H_5$ | H | H | 0 | $(CH_2)_2$ | CH—$N(CH_3)_2$ | $CH_3$ | $CH_3$ |
| 1.504 | $C_2H_5$ | H | H | 2 | $(CH_2)_2$ | CH—$N(CH_3)_2$ | $CH_3$ | $CH_3$ |
| 1.505 | $C_2H_5$ | H | H | 0 | $(CH_2)_2$ | CH—$NHOC_2H_5$ | $CH_3$ | $CH_3$ |
| 1.506 | $C_2H_5$ | H | H | 2 | $(CH_2)_2$ | CH—$NHOC_2H_5$ | $CH_3$ | $CH_3$ |
| 1.507 | $C_2H_5$ | H | H | 0 | $(CH_2)_2$ | CH—$N(CH_3)OC_2H_5$ | $CH_3$ | $CH_3$ |
| 1.508 | $C_2H_5$ | H | H | 2 | $(CH_2)_2$ | CH—$N(CH_3)OC_2H_5$ | $CH_3$ | $CH_3$ |
| 1.509 | $C_2H_5$ | H | H | 0 | $(CH_2)_2$ | C=N—$NH_2$ | $CH_3$ | $CH_3$ |
| 1.510 | $C_2H_5$ | H | H | 2 | $(CH_2)_2$ | C=N—$NH_2$ | $CH_3$ | $CH_3$ |
| 1.511 | $C_2H_5$ | H | H | 0 | $(CH_2)_2$ | C=N—$N(CH_3)_2$ | $CH_3$ | $CH_3$ |
| 1.512 | $C_2H_5$ | H | H | 2 | $(CH_2)_2$ | C=N—$N(CH_3)_2$ | $CH_3$ | $CH_3$ |
| 1.513 | $C_2H_5$ | H | H | 0 | $(CH_2)_2$ | $C(CH_3)$—$OCH_3$ | $CH_3$ | $CH_3$ |

TABLE 1-continued

Compounds of the formula

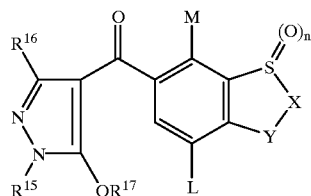

| No. | R$^{15}$ | R$^{16}$ | R$^{17}$ | n | X | Y | L | M |
|---|---|---|---|---|---|---|---|---|
| 1.514 | C$_2$H$_5$ | H | H | 2 | (CH$_2$)$_2$ | C(CH$_3$)—OCH$_3$ | CH$_3$ | CH$_3$ |
| 1.515 | C$_2$H$_5$ | H | H | 0 | (CH$_2$)$_2$ | O | CH$_3$ | CH$_3$ |
| 1.516 | C$_2$H$_5$ | H | H | 2 | (CH$_2$)$_2$ | O | CH$_3$ | CH$_3$ |
| 1.517 | CH$_3$ | CH$_3$ | H | 0 | (CH$_2$)$_2$ | CH—NHCH$_3$ | Cl | Cl |
| 1.518 | CH$_3$ | CH$_3$ | H | 2 | (CH$_2$)$_2$ | CH—NHCH$_3$ | Cl | Cl |
| 1.519 | CH$_3$ | CH$_3$ | H | 0 | (CH$_2$)$_2$ | CH—NHC$_2$H$_5$ | Cl | Cl |
| 1.520 | CH$_3$ | CH$_3$ | H | 2 | (CH$_2$)$_2$ | CH—NHC$_2$H$_5$ | Cl | Cl |
| 1.521 | CH$_3$ | CH$_3$ | H | 0 | (CH$_2$)$_2$ | CH—N(CH$_3$)$_2$ | Cl | Cl |
| 1.522 | CH$_3$ | CH$_3$ | H | 2 | (CH$_2$)$_2$ | CH—N(CH$_3$)$_2$ | Cl | Cl |
| 1.523 | CH$_3$ | CH$_3$ | H | 0 | (CH$_2$)$_2$ | CH—NHOC$_2$H$_5$ | Cl | Cl |
| 1.524 | CH$_3$ | CH$_3$ | H | 2 | (CH$_2$)$_2$ | CH—NHOC$_2$H$_5$ | Cl | Cl |
| 1.525 | CH$_3$ | CH$_3$ | H | 0 | (CH$_2$)$_2$ | CH—N(CH$_3$)OC$_2$H$_5$ | Cl | Cl |
| 1.526 | CH$_3$ | CH$_3$ | H | 2 | (CH$_2$)$_2$ | CH—N(CH$_3$)OC$_2$H$_5$ | Cl | Cl |
| 1.527 | CH$_3$ | CH$_3$ | H | 0 | (CH$_2$)$_2$ | C=N—NH$_2$ | Cl | Cl |
| 1.528 | CH$_3$ | CH$_3$ | H | 2 | (CH$_2$)$_2$ | C=N—NH$_2$ | Cl | Cl |
| 1.529 | CH$_3$ | CH$_3$ | H | 0 | (CH$_2$)$_2$ | C=N—N(CH$_3$)$_2$ | Cl | Cl |
| 1.530 | CH$_3$ | CH$_3$ | H | 2 | (CH$_2$)$_2$ | C=N—N(CH$_3$)$_2$ | Cl | Cl |
| 1.531 | CH$_3$ | CH$_3$ | H | 0 | (CH$_2$)$_2$ | C(CH$_3$)—OCH$_3$ | Cl | Cl |
| 1.532 | CH$_3$ | CH$_3$ | H | 2 | (CH$_2$)$_2$ | C(CH$_3$)—OCH$_3$ | Cl | Cl |
| 1.533 | CH$_3$ | CH$_3$ | H | 0 | (CH$_2$)$_2$ | O | Cl | Cl |
| 1.534 | CH$_3$ | CH$_3$ | H | 2 | (CH$_2$)$_2$ | O | Cl | Cl |
| 1.535 | C$_2$H$_5$ | H | H | 0 | (CH$_2$)$_2$ | CH—NHCH$_3$ | Cl | Cl |
| 1.536 | C$_2$H$_5$ | H | H | 2 | (CH$_2$)$_2$ | CH—NHCH$_3$ | Cl | Cl |
| 1.537 | C$_2$H$_5$ | H | H | 0 | (CH$_2$)$_2$ | CH—NHC$_2$H$_5$ | Cl | Cl |
| 1.538 | C$_2$H$_5$ | H | H | 2 | (CH$_2$)$_2$ | CH—NHC$_2$H$_5$ | Cl | Cl |
| 1.539 | C$_2$H$_5$ | H | H | 0 | (CH$_2$)$_2$ | CH—N(CH$_3$)$_2$ | Cl | Cl |
| 1.540 | C$_2$H$_5$ | H | H | 2 | (CH$_2$)$_2$ | CH—N(CH$_3$)$_2$ | Cl | Cl |
| 1.541 | C$_2$H$_5$ | H | H | 0 | (CH$_2$)$_2$ | CH—NHOC$_2$H$_5$ | Cl | Cl |
| 1.542 | C$_2$H$_5$ | H | H | 2 | (CH$_2$)$_2$ | CH—NHOC$_2$H$_5$ | Cl | Cl |
| 1.543 | C$_2$H$_5$ | H | H | 0 | (CH$_2$)$_2$ | CH—N(CH$_3$)OC$_2$H$_5$ | Cl | Cl |
| 1.544 | C$_2$H$_5$ | H | H | 2 | (CH$_2$)$_2$ | CH—N(CH$_3$)OC$_2$H$_5$ | Cl | Cl |
| 1.545 | C$_2$H$_5$ | H | H | 0 | (CH$_2$)$_2$ | C=N—NH$_2$ | Cl | Cl |
| 1.546 | C$_2$H$_5$ | H | H | 2 | (CH$_2$)$_2$ | C=N—NH$_2$ | Cl | Cl |
| 1.547 | C$_2$H$_5$ | H | H | 0 | (CH$_2$)$_2$ | C=N—N(CH$_3$)$_2$ | Cl | Cl |
| 1.548 | C$_2$H$_5$ | H | H | 2 | (CH$_2$)$_2$ | C=N—N(CH$_3$)$_2$ | Cl | Cl |
| 1.549 | C$_2$H$_5$ | H | H | 0 | (CH$_2$)$_2$ | C(CH$_3$)—OCH$_3$ | Cl | Cl |
| 1.550 | C$_2$H$_5$ | H | H | 2 | (CH$_2$)$_2$ | C(CH$_3$)—OCH$_3$ | Cl | Cl |
| 1.551 | C$_2$H$_5$ | H | H | 0 | (CH$_2$)$_2$ | O | Cl | Cl |
| 1.552 | C$_2$H$_5$ | H | H | 2 | (CH$_2$)$_2$ | O | Cl | Cl |
| 1.553 | CH$_3$ | CH$_3$ | H | 0 | (CH$_2$)$_2$ | C=O | Cl | Cl |
| 1.554 | CH$_3$ | CH$_3$ | H | 2 | (CH$_2$)$_2$ | C=O | Cl | Cl |
| 1.555 | CH$_3$ | CH$_3$ | H | 0 | (CH$_2$)$_2$ | CHOCH$_3$ | Cl | Cl |
| 1.556 | CH$_3$ | CH$_3$ | H | 2 | (CH$_2$)$_2$ | CHOCH$_3$ | Cl | Cl |
| 1.557 | CH$_3$ | CH$_3$ | H | 0 | (CH$_2$)$_2$ | CHOC$_2$H$_5$ | Cl | Cl |
| 1.558 | CH$_3$ | CH$_3$ | H | 2 | (CH$_2$)$_2$ | CHOC$_2$H$_5$ | Cl | Cl |
| 1.559 | CH$_3$ | CH$_3$ | H | 0 | (CH$_2$)$_2$ | CHOiPr | Cl | Cl |
| 1.560 | CH$_3$ | CH$_3$ | H | 2 | (CH$_2$)$_2$ | CHOiPr | Cl | Cl |
| 1.561 | CH$_3$ | CH$_3$ | H | 0 | (CH$_2$)$_2$ | CHOH | Cl | Cl |
| 1.562 | CH$_3$ | CH$_3$ | H | 2 | (CH$_2$)$_2$ | CHOH | Cl | Cl |
| 1.563 | CH$_3$ | CH$_3$ | H | 0 | (CH$_2$)$_2$ | C=NOCH$_3$ | Cl | Cl |
| 1.564 | CH$_3$ | CH$_3$ | H | 2 | (CH$_2$)$_2$ | C=NOCH$_3$ | Cl | Cl |
| 1.565 | CH$_3$ | CH$_3$ | H | 0 | (CH$_2$)$_2$ | C=NOC$_2$H$_5$ | Cl | Cl |
| 1.566 | CH$_3$ | CH$_3$ | H | 2 | (CH$_2$)$_2$ | C=NOC$_2$H$_5$ | Cl | Cl |
| 1.567 | CH$_3$ | CH$_3$ | H | 0 | (CH$_2$)$_2$ | C=NOiPr | Cl | Cl |
| 1.568 | CH$_3$ | CH$_3$ | H | 2 | (CH$_2$)$_2$ | C=NOiPr | Cl | Cl |
| 1.569 | CH$_3$ | CH$_3$ | H | 0 | (CH$_2$)$_2$ | C=NOCH$_2$CH=CHCl | Cl | Cl |
| 1.570 | CH$_3$ | CH$_3$ | H | 2 | (CH$_2$)$_2$ | C=NOCH$_2$CH=CHCl | Cl | Cl |
| 1.571 | CH$_3$ | CH$_3$ | H | 0 | (CH$_2$)$_2$ | C=NOCH$_2$C$_6$H$_5$ | Cl | Cl |
| 1.572 | CH$_3$ | CH$_3$ | H | 2 | (CH$_2$)$_2$ | C=NOCH$_2$C$_6$H$_5$ | Cl | Cl |
| 1.573 | CH$_3$ | CH$_3$ | H | 0 | (CH$_2$)$_2$ | C(CH$_3$)$_2$ | Cl | Cl |
| 1.574 | CH$_3$ | CH$_3$ | H | 2 | (CH$_2$)$_2$ | C(CH$_3$)$_2$ | Cl | Cl |
| 1.575 | C$_2$H$_5$ | H | H | 0 | (CH$_2$)$_2$ | C=O | Cl | Cl |
| 1.576 | C$_2$H$_5$ | H | H | 2 | (CH$_2$)$_2$ | C=O | Cl | Cl |

TABLE 1-continued

Compounds of the formula

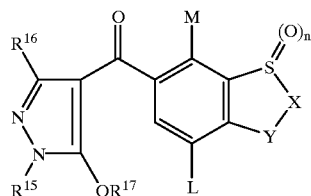

| No. | $R^{15}$ | $R^{16}$ | $R^{17}$ | n | X | Y | L | M |
|---|---|---|---|---|---|---|---|---|
| 1.577 | $C_2H_5$ | H | H | 0 | $(CH_2)_2$ | $CHOCH_3$ | Cl | Cl |
| 1.578 | $C_2H_5$ | H | H | 2 | $(CH_2)_2$ | $CHOCH_3$ | Cl | Cl |
| 1.579 | $C_2H_5$ | H | H | 0 | $(CH_2)_2$ | $CHOC_2H_5$ | Cl | Cl |
| 1.580 | $C_2H_5$ | H | H | 2 | $(CH_2)_2$ | $CHOC_2H_5$ | Cl | Cl |
| 1.581 | $C_2H_5$ | H | H | 0 | $(CH_2)_2$ | $CHOiPr$ | Cl | Cl |
| 1.582 | $C_2H_5$ | H | H | 2 | $(CH_2)_2$ | $CHOiPr$ | Cl | Cl |
| 1.583 | $C_2H_5$ | H | H | 0 | $(CH_2)_2$ | $CHOH$ | Cl | Cl |
| 1.584 | $C_2H_5$ | H | H | 2 | $(CH_2)_2$ | $CHOH$ | Cl | Cl |
| 1.585 | $C_2H_5$ | H | H | 0 | $(CH_2)_2$ | $C=NOCH_3$ | Cl | Cl |
| 1.586 | $C_2H_5$ | H | H | 2 | $(CH_2)_2$ | $C=NOCH_3$ | Cl | Cl |
| 1.587 | $C_2H_5$ | H | H | 0 | $(CH_2)_2$ | $C=NOC_2H_5$ | Cl | Cl |
| 1.588 | $C_2H_5$ | H | H | 2 | $(CH_2)_2$ | $C=NOC_2H_5$ | Cl | Cl |
| 1.589 | $C_2H_5$ | H | H | 0 | $(CH_2)_2$ | $C=NOiPr$ | Cl | Cl |
| 1.590 | $C_2H_5$ | H | H | 2 | $(CH_2)_2$ | $C=NOiPr$ | Cl | Cl |
| 1.591 | $C_2H_5$ | H | H | 0 | $(CH_2)_2$ | $C=NOCH_2CH=CHCl$ | Cl | Cl |
| 1.592 | $C_2H_5$ | H | H | 2 | $(CH_2)_2$ | $C=NOCH_2CH=CHCl$ | Cl | Cl |
| 1.593 | $C_2H_5$ | H | H | 0 | $(CH_2)_2$ | $C=NOCH_2C_6H_5$ | Cl | Cl |
| 1.594 | $C_2H_5$ | H | H | 2 | $(CH_2)_2$ | $C=NOCH_2C_6H_5$ | Cl | Cl |
| 1.595 | $C_2H_5$ | H | H | 0 | $(CH_2)_2$ | $C(CH_3)_2$ | Cl | Cl |
| 1.596 | $C_2H_5$ | H | H | 2 | $(CH_2)_2$ | $C(CH_3)_2$ | Cl | Cl |
| 1.597 | $CH_3$ | $CH_3$ | H | 0 | $(CH_2)_2$ | $C=O$ | $CH_3$ | $CH_3$ |
| 1.598 | $CH_3$ | $CH_3$ | H | 2 | $(CH_2)_2$ | $C=O$ | $CH_3$ | $CH_3$ |
| 1.599 | $CH_3$ | $CH_3$ | H | 0 | $(CH_2)_2$ | $CHOCH_3$ | $CH_3$ | $CH_3$ |
| 1.600 | $CH_3$ | $CH_3$ | H | 2 | $(CH_2)_2$ | $CHOCH_3$ | $CH_3$ | $CH_3$ |
| 1.601 | $CH_3$ | $CH_3$ | H | 0 | $(CH_2)_2$ | $CHOC_2H_5$ | $CH_3$ | $CH_3$ |
| 1.602 | $CH_3$ | $CH_3$ | H | 2 | $(CH_2)_2$ | $CHOC_2H_5$ | $CH_3$ | $CH_3$ |
| 1.603 | $CH_3$ | $CH_3$ | H | 0 | $(CH_2)_2$ | $CHOiPr$ | $CH_3$ | $CH_3$ |
| 1.604 | $CH_3$ | $CH_3$ | H | 2 | $(CH_2)_2$ | $CHOiPr$ | $CH_3$ | $CH_3$ |
| 1.605 | $CH_3$ | $CH_3$ | H | 0 | $(CH_2)_2$ | $CHOH$ | $CH_3$ | $CH_3$ |
| 1.606 | $CH_3$ | $CH_3$ | H | 2 | $(CH_2)_2$ | $CHOH$ | $CH_3$ | $CH_3$ |
| 1.607 | $CH_3$ | $CH_3$ | H | 0 | $(CH_2)_2$ | $C=NOCH_3$ | $CH_3$ | $CH_3$ |
| 1.608 | $CH_3$ | $CH_3$ | H | 2 | $(CH_2)_2$ | $C=NOCH_3$ | $CH_3$ | $CH_3$ |
| 1.609 | $CH_3$ | $CH_3$ | H | 0 | $(CH_2)_2$ | $C=NOC_2H_5$ | $CH_3$ | $CH_3$ |
| 1.610 | $CH_3$ | $CH_3$ | H | 2 | $(CH_2)_2$ | $C=NOC_2H_5$ | $CH_3$ | $CH_3$ |
| 1.611 | $CH_3$ | $CH_3$ | H | 0 | $(CH_2)_2$ | $C=NOiPr$ | $CH_3$ | $CH_3$ |
| 1.612 | $CH_3$ | $CH_3$ | H | 2 | $(CH_2)_2$ | $C=NOiPr$ | $CH_3$ | $CH_3$ |
| 1.613 | $CH_3$ | $CH_3$ | H | 0 | $(CH_2)_2$ | $C=NOCH_2CH=CHCl$ | $CH_3$ | $CH_3$ |
| 1.614 | $CH_3$ | $CH_3$ | H | 2 | $(CH_2)_2$ | $C=NOCH_2CH=CHCl$ | $CH_3$ | $CH_3$ |
| 1.615 | $CH_3$ | $CH_3$ | H | 0 | $(CH_2)_2$ | $C=NOCH_2C_6H_5$ | $CH_3$ | $CH_3$ |
| 1.616 | $CH_3$ | $CH_3$ | H | 2 | $(CH_2)_2$ | $C=NOCH_2C_6H_5$ | $CH_3$ | $CH_3$ |
| 1.617 | $CH_3$ | $CH_3$ | H | 0 | $(CH_2)_2$ | $C(CH_3)_2$ | $CH_3$ | $CH_3$ |
| 1.618 | $CH_3$ | $CH_3$ | H | 2 | $(CH_2)_2$ | $C(CH_3)_2$ | $CH_3$ | $CH_3$ |
| 1.619 | $C_2H_5$ | H | H | 0 | $(CH_2)_2$ | $C=O$ | $CH_3$ | $CH_3$ |
| 1.620 | $C_2H_5$ | H | H | 2 | $(CH_2)_2$ | $C=O$ | $CH_3$ | $CH_3$ |
| 1.621 | $C_2H_5$ | H | H | 0 | $(CH_2)_2$ | $CHOCH_3$ | $CH_3$ | $CH_3$ |
| 1.622 | $C_2H_5$ | H | H | 2 | $(CH_2)_2$ | $CHOCH_3$ | $CH_3$ | $CH_3$ |
| 1.623 | $C_2H_5$ | H | H | 0 | $(CH_2)_2$ | $CHOC_2H_5$ | $CH_3$ | $CH_3$ |
| 1.624 | $C_2H_5$ | H | H | 2 | $(CH_2)_2$ | $CHOC_2H_5$ | $CH_3$ | $CH_3$ |
| 1.625 | $C_2H_5$ | H | H | 0 | $(CH_2)_2$ | $CHOiPr$ | $CH_3$ | $CH_3$ |
| 1.626 | $C_2H_5$ | H | H | 2 | $(CH_2)_2$ | $CHOiPr$ | $CH_3$ | $CH_3$ |
| 1.627 | $C_2H_5$ | H | H | 0 | $(CH_2)_2$ | $CHOH$ | $CH_3$ | $CH_3$ |
| 1.628 | $C_2H_5$ | H | H | 2 | $(CH_2)_2$ | $CHOH$ | $CH_3$ | $CH_3$ |
| 1.629 | $C_2H_5$ | H | H | 0 | $(CH_2)_2$ | $C=NOCH_3$ | $CH_3$ | $CH_3$ |
| 1.630 | $C_2H_5$ | H | H | 2 | $(CH_2)_2$ | $C=NOCH_3$ | $CH_3$ | $CH_3$ |
| 1.631 | $C_2H_5$ | H | H | 0 | $(CH_2)_2$ | $C=NOC_2H_5$ | $CH_3$ | $CH_3$ |
| 1.632 | $C_2H_5$ | H | H | 2 | $(CH_2)_2$ | $C=NOC_2H_5$ | $CH_3$ | $CH_3$ |
| 1.633 | $C_2H_5$ | H | H | 0 | $(CH_2)_2$ | $C=NOiPr$ | $CH_3$ | $CH_3$ |
| 1.634 | $C_2H_5$ | H | H | 2 | $(CH_2)_2$ | $C=NOiPr$ | $CH_3$ | $CH_3$ |
| 1.635 | $C_2H_5$ | H | H | 0 | $(CH_2)_2$ | $C=NOCH_2CH=CHCl$ | $CH_3$ | $CH_3$ |
| 1.636 | $C_2H_5$ | H | H | 2 | $(CH_2)_2$ | $C=NOCH_2CH=CHCl$ | $CH_3$ | $CH_3$ |
| 1.637 | $C_2H_5$ | H | H | 0 | $(CH_2)_2$ | $C=NOCH_2C_6H_5$ | $CH_3$ | $CH_3$ |

TABLE 1-continued

Compounds of the formula

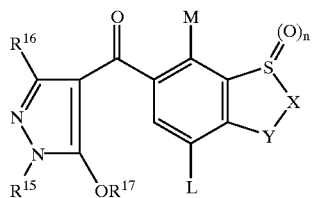

| No. | R15 | R16 | R17 | n | X | Y | L | M |
|---|---|---|---|---|---|---|---|---|
| 1.638 | C2H5 | H | H | 2 | (CH2)2 | C=NOCH2C6H5 | CH3 | CH3 |
| 1.639 | C2H5 | H | H | 0 | (CH2)2 | C(CH3)2 | CH3 | CH3 |
| 1.640 | C2H5 | H | H | 2 | (CH2)2 | C(CH3)2 | CH3 | CH3 |

TABLE 2

Compounds of the formula

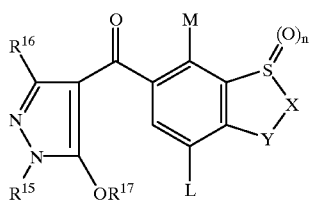

| No. | R15 | R16 | R17 | n | X | Y | L | M |
|---|---|---|---|---|---|---|---|---|
| 2.1 | CH3 | CH3 | H | 0 | N | COCH3 | H | CH3 |
| 2.2 | CH3 | CH3 | H | 2 | N | COCH3 | H | CH3 |
| 2.3 | CH3 | CH3 | H | 0 | N | COC2H5 | H | CH3 |
| 2.4 | CH3 | CH3 | H | 2 | N | COC2H5 | H | CH3 |
| 2.5 | CH3 | CH3 | H | 0 | N | COiPr | H | CH3 |
| 2.6 | CH3 | CH3 | H | 2 | N | COiPr | H | CH3 |
| 2.7 | C2H5 | H | H | 0 | N | COCH3 | H | CH3 |
| 2.8 | C2H5 | H | H | 2 | N | COCH3 | H | CH3 |
| 2.9 | C2H5 | H | H | 0 | N | COC2H5 | H | CH3 |
| 2.10 | C2H5 | H | H | 2 | N | COC2H5 | H | CH3 |
| 2.11 | C2H5 | H | H | 0 | N | COiPr | H | CH3 |
| 2.12 | C2H5 | H | H | 2 | N | COiPr | H | CH3 |
| 2.13 | CH3 | CH3 | H | 0 | CH | COCH3 | H | CH3 |
| 2.14 | CH3 | CH3 | H | 2 | CH | COCH3 | H | CH3 |
| 2.15 | CH3 | CH3 | H | 0 | CH | COC2H5 | H | CH3 |
| 2.16 | CH3 | CH3 | H | 2 | CH | COC2H5 | H | CH3 |
| 2.17 | CH3 | CH3 | H | 0 | CH | COiPr | H | CH3 |
| 2.18 | CH3 | CH3 | H | 2 | CH | COiPr | H | CH3 |
| 2.19 | C2H5 | H | H | 0 | CH | COCH3 | H | CH3 |
| 2.20 | C2H5 | H | H | 2 | CH | COCH3 | H | CH3 |
| 2.21 | C2H5 | H | H | 0 | CH | COC2H5 | H | CH3 |
| 2.22 | C2H5 | H | H | 2 | CH | COC2H5 | H | CH3 |
| 2.23 | C2H5 | H | H | 0 | CH | COiPr | H | CH3 |
| 2.24 | C2H5 | H | H | 2 | CH | COiPr | H | CH3 |
| 2.25 | CH3 | CH3 | H | 0 | N | COCH3 | H | Cl |
| 2.26 | CH3 | CH3 | H | 2 | N | COCH3 | H | Cl |
| 2.27 | CH3 | CH3 | H | 0 | N | COC2H5 | H | Cl |
| 2.28 | CH3 | CH3 | H | 2 | N | COC2H5 | H | Cl |
| 2.29 | CH3 | CH3 | H | 0 | N | COiPr | H | Cl |
| 2.30 | CH3 | CH3 | H | 2 | N | COiPr | H | Cl |
| 2.31 | C2H5 | H | H | 0 | N | COCH3 | H | Cl |
| 2.32 | C2H5 | H | H | 2 | N | COCH3 | H | Cl |
| 2.33 | C2H5 | H | H | 0 | N | COC2H5 | H | Cl |
| 2.34 | C2H5 | H | H | 2 | N | COC2H5 | H | Cl |
| 2.35 | C2H5 | H | H | 0 | N | COiPr | H | Cl |
| 2.36 | C2H5 | H | H | 2 | N | COiPr | H | Cl |
| 2.37 | CH3 | CH3 | H | 0 | CH | COCH3 | H | Cl |
| 2.38 | CH3 | CH3 | H | 2 | CH | COCH3 | H | Cl |

TABLE 2-continued

Compounds of the formula

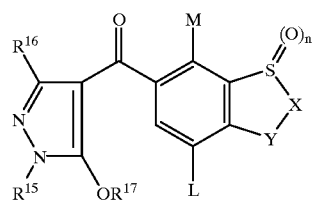

| No. | R15 | R16 | R17 | n | X | Y | L | M |
|---|---|---|---|---|---|---|---|---|
| 2.39 | CH3 | CH3 | H | 0 | CH | COC2H5 | H | Cl |
| 2.40 | CH3 | CH3 | H | 2 | CH | COC2H5 | H | Cl |
| 2.41 | CH3 | CH3 | H | 0 | CH | COiPr | H | Cl |
| 2.42 | CH3 | CH3 | H | 2 | CH | COiPr | H | Cl |
| 2.43 | C2H5 | H | H | 0 | CH | COCH3 | H | Cl |
| 2.44 | C2H5 | H | H | 2 | CH | COCH3 | H | Cl |
| 2.45 | C2H5 | H | H | 0 | CH | COC2H5 | H | Cl |
| 2.46 | C2H5 | H | H | 2 | CH | COC2H5 | H | Cl |
| 2.47 | C2H5 | H | H | 0 | CH | COiPr | H | Cl |
| 2.48 | C2H5 | H | H | 2 | CH | COiPr | H | Cl |

TABLE 3

Compounds of the formula

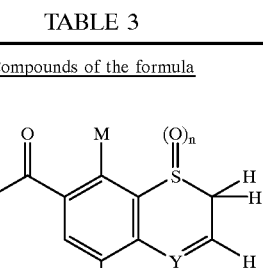

| No. | R15 | R16 | R17 | n | Y | L | M |
|---|---|---|---|---|---|---|---|
| 3.1 | CH3 | CH3 | H | 0 | COCH3 | H | CH3 |
| 3.2 | CH3 | CH3 | H | 2 | COCH3 | H | CH3 |
| 3.3 | CH3 | CH3 | H | 0 | COC2H5 | H | CH3 |
| 3.4 | CH3 | CH3 | H | 2 | COC2H5 | H | CH3 |
| 3.5 | CH3 | CH3 | H | 0 | COiPr | H | CH3 |
| 3.6 | CH3 | CH3 | H | 2 | COiPr | H | CH3 |
| 3.7 | C2H5 | H | H | 0 | COCH3 | H | CH3 |

TABLE 3-continued

Compounds of the formula

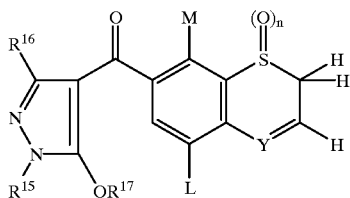

| No. | $R^{15}$ | $R^{16}$ | $R^{17}$ | n | Y | L | M |
|---|---|---|---|---|---|---|---|
| 3.8 | $C_2H_5$ | H | H | 2 | $COCH_3$ | H | $CH_3$ |
| 3.9 | $C_2H_5$ | H | H | 0 | $COC_2H_5$ | H | $CH_3$ |
| 3.10 | $C_2H_5$ | H | H | 2 | $COC_2H_5$ | H | $CH_3$ |
| 3.11 | $C_2H_5$ | H | H | 0 | COiPr | H | $CH_3$ |
| 3.12 | $C_2H_5$ | H | H | 2 | COiPr | H | $CH_3$ |
| 3.13 | $CH_3$ | $CH_3$ | H | 0 | $COCH_3$ | H | Cl |
| 3.14 | $CH_3$ | $CH_3$ | H | 2 | $COCH_3$ | H | Cl |
| 3.15 | $CH_3$ | $CH_3$ | H | 0 | $COC_2H_5$ | H | Cl |
| 3.16 | $CH_3$ | $CH_3$ | H | 2 | $COC_2H_5$ | H | Cl |
| 3.17 | $CH_3$ | $CH_3$ | H | 0 | COiPr | H | Cl |
| 3.18 | $CH_3$ | $CH_3$ | H | 2 | COiPr | H | Cl |
| 3.19 | $C_2H_5$ | H | H | 0 | $COCH_3$ | H | Cl |
| 3.20 | $C_2H_5$ | H | H | 2 | $COCH_3$ | H | Cl |
| 3.21 | $C_2H_5$ | H | H | 0 | $COC_2H_5$ | H | Cl |
| 3.22 | $C_2H_5$ | H | H | 2 | $COC_2H_5$ | H | Cl |
| 3.23 | $C_2H_5$ | H | H | 0 | COiPr | H | Cl |
| 3.24 | $C_2H_5$ | H | H | 2 | COiPr | H | Cl |

TABLE 4

Compounds of the formula

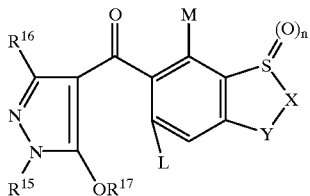

| No. | $R^{15}$ | $R^{16}$ | $R^{17}$ | n | X | Y | M | L |
|---|---|---|---|---|---|---|---|---|
| 4.1 | $CH_3$ | $CH_3$ | H | 0 | $CH_2$ | C=O | H | $CH_3$ |
| 4.2 | $CH_3$ | $CH_3$ | H | 2 | $CH_2$ | C=O | H | $CH_3$ |
| 4.3 | $CH_3$ | $CH_3$ | H | 0 | $CH_2$ | $CHOCH_3$ | H | $CH_3$ |
| 4.4 | $CH_3$ | $CH_3$ | H | 2 | $CH_2$ | $CHOCH_3$ | H | $CH_3$ |
| 4.5 | $CH_3$ | $CH_3$ | H | 0 | $CH_2$ | $CHOC_2H_5$ | H | $CH_3$ |
| 4.6 | $CH_3$ | $CH_3$ | H | 2 | $CH_2$ | $CHOC_2H_5$ | H | $CH_3$ |
| 4.7 | $CH_3$ | $CH_3$ | H | 0 | $CH_2$ | CHOiPr | H | $CH_3$ |
| 4.8 | $CH_3$ | $CH_3$ | H | 2 | $CH_2$ | CHOiPr | H | $CH_3$ |
| 4.9 | $CH_3$ | $CH_3$ | H | 0 | $CH_2$ | CHOH | H | $CH_3$ |
| 4.10 | $CH_3$ | $CH_3$ | H | 2 | $CH_2$ | CHOH | H | $CH_3$ |
| 4.11 | $CH_3$ | $CH_3$ | H | 0 | $CH_2$ | C=$NOCH_3$ | H | $CH_3$ |
| 4.12 | $CH_3$ | $CH_3$ | H | 2 | $CH_2$ | C=$NOCH_3$ | H | $CH_3$ |
| 4.13 | $CH_3$ | $CH_3$ | H | 0 | $CH_2$ | C=$NOC_2H_5$ | H | $CH_3$ |
| 4.14 | $CH_3$ | $CH_3$ | H | 2 | $CH_2$ | C=$NOC_2H_5$ | H | $CH_3$ |
| 4.15 | $CH_3$ | $CH_3$ | H | 0 | $CH_2$ | C=NOiPr | H | $CH_3$ |
| 4.16 | $CH_3$ | $CH_3$ | H | 2 | $CH_2$ | C=NOiPr | H | $CH_3$ |
| 4.17 | $CH_3$ | $CH_3$ | H | 0 | $CH_2$ | C=$NOCH_2CH$=CHCl | H | $CH_3$ |
| 4.18 | $CH_3$ | $CH_3$ | H | 2 | $CH_2$ | C=$NOCH_2CH$=CHCl | H | $CH_3$ |
| 4.19 | $CH_3$ | $CH_3$ | H | 0 | $CH_2$ | C=$NOCH_2C_6H_5$ | H | $CH_3$ |
| 4.20 | $CH_3$ | $CH_3$ | H | 2 | $CH_2$ | C=$NOCH_2C_6H_5$ | H | $CH_3$ |
| 4.21 | $CH_3$ | $CH_3$ | H | 0 | $CH_2$ | $C(CH_3)_2$ | H | $CH_3$ |
| 4.22 | $CH_3$ | $CH_3$ | H | 2 | $CH_2$ | $C(CH_3)_2$ | H | $CH_3$ |
| 4.23 | $C_2H_5$ | H | H | 0 | $CH_2$ | C=O | H | $CH_3$ |
| 4.24 | $C_2H_5$ | H | H | 2 | $CH_2$ | C=O | H | $CH_3$ |

TABLE 4-continued

Compounds of the formula

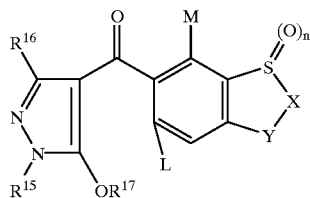

| No. | R¹⁵ | R¹⁶ | R¹⁷ | n | X | Y | M | L |
|---|---|---|---|---|---|---|---|---|
| 4.25 | C₂H₅ | H | H | 0 | CH₂ | CHOCH₃ | H | CH₃ |
| 4.26 | C₂H₅ | H | H | 2 | CH₂ | CHOCH₃ | H | CH₃ |
| 4.27 | C₂H₅ | H | H | 0 | CH₂ | CHOC₂H₅ | H | CH₃ |
| 4.28 | C₂H₅ | H | H | 2 | CH₂ | CHOC₂H₅ | H | CH₃ |
| 4.29 | C₂H₅ | H | H | 0 | CH₂ | CHOiPr | H | CH₃ |
| 4.30 | C₂H₅ | H | H | 2 | CH₂ | CHOiPr | H | CH₃ |
| 4.31 | C₂H₅ | H | H | 0 | CH₂ | CHOH | H | CH₃ |
| 4.32 | C₂H₅ | H | H | 2 | CH₂ | CHOH | H | CH₃ |
| 4.33 | C₂H₅ | H | H | 0 | CH₂ | C=NOCH₃ | H | CH₃ |
| 4.34 | C₂H₅ | H | H | 2 | CH₂ | C=NOCH₃ | H | CH₃ |
| 4.35 | C₂H₅ | H | H | 0 | CH₂ | C=NOC₂H₅ | H | CH₃ |
| 4.36 | C₂H₅ | H | H | 2 | CH₂ | C=NOC₂H₅ | H | CH₃ |
| 4.37 | C₂H₅ | H | H | 0 | CH₂ | C=NOiPr | H | CH₃ |
| 4.38 | C₂H₅ | H | H | 2 | CH₂ | C=NOiPr | H | CH₃ |
| 4.39 | C₂H₅ | H | H | 0 | CH₂ | C=NOCH₂CH=CHCl | H | CH₃ |
| 4.40 | C₂H₅ | H | H | 2 | CH₂ | C=NOCH₂CH=CHCl | H | CH₃ |
| 4.41 | C₂H₅ | H | H | 0 | CH₂ | C=NOCH₂C₆H₅ | H | CH₃ |
| 4.42 | C₂H₅ | H | H | 2 | CH₂ | C=NOCH₂C₆H₅ | H | CH₃ |
| 4.43 | C₂H₅ | H | H | 0 | CH₂ | C(CH₃)₂ | H | CH₃ |
| 4.44 | C₂H₅ | H | H | 2 | CH₂ | C(CH₃)₂ | H | CH₃ |
| 4.45 | CH₃ | CH₃ | H | 0 | CH₂ | C=O | H | Cl |
| 4.46 | CH₃ | CH₃ | H | 2 | CH₂ | C=O | H | Cl |
| 4.47 | CH₃ | CH₃ | H | 0 | CH₂ | CHOCH₃ | H | Cl |
| 4.48 | CH₃ | CH₃ | H | 2 | CH₂ | CHOCH₃ | H | Cl |
| 4.49 | CH₃ | CH₃ | H | 0 | CH₂ | CHOC₂H₅ | H | Cl |
| 4.50 | CH₃ | CH₃ | H | 2 | CH₂ | CHOC₂H₅ | H | Cl |
| 4.51 | CH₃ | CH₃ | H | 0 | CH₂ | CHOiPr | H | Cl |
| 4.52 | CH₃ | CH₃ | H | 2 | CH₂ | CHOiPr | H | Cl |
| 4.53 | CH₃ | CH₃ | H | 0 | CH₂ | CHOH | H | Cl |
| 4.54 | CH₃ | CH₃ | H | 2 | CH₂ | CHOH | H | Cl |
| 4.55 | CH₃ | CH₃ | H | 0 | CH₂ | C=NOCH₃ | H | Cl |
| 4.56 | CH₃ | CH₃ | H | 2 | CH₂ | C=NOCH₃ | H | Cl |
| 4.57 | CH₃ | CH₃ | H | 0 | CH₂ | C=NOC₂H₅ | H | Cl |
| 4.58 | CH₃ | CH₃ | H | 2 | CH₂ | C=NOC₂H₅ | H | Cl |
| 4.59 | CH₃ | CH₃ | H | 0 | CH₂ | C=NOiPr | H | Cl |
| 4.60 | CH₃ | CH₃ | H | 2 | CH₂ | C=NOiPr | H | Cl |
| 4.61 | CH₃ | CH₃ | H | 0 | CH₂ | C=NOCH₂CH=CHCl | H | Cl |
| 4.62 | CH₃ | CH₃ | H | 2 | CH₂ | C=NOCH₂CH=CHCl | H | Cl |
| 4.63 | CH₃ | CH₃ | H | 0 | CH₂ | C=NOCH₂C₆H₅ | H | Cl |
| 4.64 | CH₃ | CH₃ | H | 2 | CH₂ | C=NOCH₂C₆H₅ | H | Cl |
| 4.65 | CH₃ | CH₃ | H | 0 | CH₂ | C(CH₃)₂ | H | Cl |
| 4.66 | CH₃ | CH₃ | H | 2 | CH₂ | C(CH₃)₂ | H | Cl |
| 4.67 | C₂H₅ | H | H | 0 | CH₂ | C=O | H | Cl |
| 4.68 | C₂H₅ | H | H | 2 | CH₂ | C=O | H | Cl |
| 4.69 | C₂H₅ | H | H | 0 | CH₂ | CHOCH₃ | H | Cl |
| 4.70 | C₂H₅ | H | H | 2 | CH₂ | CHOCH₃ | H | Cl |
| 4.71 | C₂H₅ | H | H | 0 | CH₂ | CHOC₂H₅ | H | Cl |
| 4.72 | C₂H₅ | H | H | 2 | CH₂ | CHOC₂H₅ | H | Cl |
| 4.73 | C₂H₅ | H | H | 0 | CH₂ | CHOiPr | H | Cl |
| 4.74 | C₂H₅ | H | H | 2 | CH₂ | CHOiPr | H | Cl |
| 4.75 | C₂H₅ | H | H | 0 | CH₂ | CHOH | H | Cl |
| 4.76 | C₂H₅ | H | H | 2 | CH₂ | CHOH | H | Cl |
| 4.77 | C₂H₅ | H | H | 0 | CH₂ | C=NOCH₃ | H | Cl |
| 4.78 | C₂H₅ | H | H | 2 | CH₂ | C=NOCH₃ | H | Cl |
| 4.79 | C₂H₅ | H | H | 0 | CH₂ | C=NOC₂H₅ | H | Cl |
| 4.80 | C₂H₅ | H | H | 2 | CH₂ | C=NOC₂H₅ | H | Cl |
| 4.81 | C₂H₅ | H | H | 0 | CH₂ | C=NOiPr | H | Cl |
| 4.82 | C₂H₅ | H | H | 2 | CH₂ | C=NOiPr | H | Cl |
| 4.83 | C₂H₅ | H | H | 0 | CH₂ | C=NOCH₂CH=CHCl | H | Cl |
| 4.84 | C₂H₅ | H | H | 2 | CH₂ | C=NOCH₂CH=CHCl | H | Cl |
| 4.85 | C₂H₅ | H | H | 0 | CH₂ | C=NOCH₂C₆H₅ | H | Cl |
| 4.86 | C₂H₅ | H | H | 2 | CH₂ | C=NOCH₂C₆H₅ | H | Cl |
| 4.87 | C₂H₅ | H | H | 0 | CH₂ | C(CH₃)₂ | H | Cl |

TABLE 4-continued

Compounds of the formula

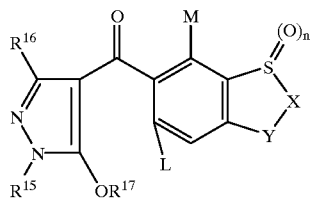

| No. | $R^{15}$ | $R^{16}$ | $R^{17}$ | n | X | Y | M | L |
|---|---|---|---|---|---|---|---|---|
| 4.88 | $C_2H_5$ | H | H | 2 | $CH_2$ | $C(CH_3)_2$ | H | Cl |
| 4.89 | $CH_3$ | $CH_3$ | H | 0 | $(CH_2)_2$ | C=O | H | Cl |
| 4.90 | $CH_3$ | $CH_3$ | H | 2 | $(CH_2)_2$ | C=O | H | Cl |
| 4.91 | $CH_3$ | $CH_3$ | H | 0 | $(CH_2)_2$ | $CHOCH_3$ | H | Cl |
| 4.92 | $CH_3$ | $CH_3$ | H | 2 | $(CH_2)_2$ | $CHOCH_3$ | H | Cl |
| 4.93 | $CH_3$ | $CH_3$ | H | 0 | $(CH_2)_2$ | $CHOC_2H_5$ | H | Cl |
| 4.94 | $CH_3$ | $CH_3$ | H | 2 | $(CH_2)_2$ | $CHOC_2H_5$ | H | Cl |
| 4.95 | $CH_3$ | $CH_3$ | H | 0 | $(CH_2)_2$ | CHOiPr | H | Cl |
| 4.96 | $CH_3$ | $CH_3$ | H | 2 | $(CH_2)_2$ | CHOiPr | H | Cl |
| 4.97 | $CH_3$ | $CH_3$ | H | 0 | $(CH_2)_2$ | CHOH | H | Cl |
| 4.98 | $CH_3$ | $CH_3$ | H | 2 | $(CH_2)_2$ | CHOH | H | ci |
| 4.99 | $CH_3$ | $CH_3$ | H | 0 | $(CH_2)_2$ | $C=NOCH_3$ | H | Cl |
| 4.100 | $CH_3$ | $CH_3$ | H | 2 | $(CH_2)_2$ | $C=NOCH_3$ | H | Cl |
| 4.101 | $CH_3$ | $CH_3$ | H | 0 | $(CH_2)_2$ | $C=NOC_2H_5$ | H | Cl |
| 4.102 | $CH_3$ | $CH_3$ | H | 2 | $(CH_2)_2$ | $C=NOC_2H_5$ | H | Cl |
| 4.103 | $CH_3$ | $CH_3$ | H | 0 | $(CH_2)_2$ | C=NOiPr | H | Cl |
| 4.104 | $CH_3$ | $CH_3$ | H | 2 | $(CH_2)_2$ | C=NOiPr | H | Cl |
| 4.105 | $CH_3$ | $CH_3$ | H | 0 | $(CH_2)_2$ | $C=NOCH_2CH=CHCl$ | H | Cl |
| 4.106 | $CH_3$ | $CH_3$ | H | 2 | $(CH_2)_2$ | $C=NOCH_2CH=CHCl$ | H | Cl |
| 4.107 | $CH_3$ | $CH_3$ | H | 0 | $(CH_2)_2$ | $C=NOCH_2C_6H_5$ | H | Cl |
| 4.108 | $CH_3$ | $CH_3$ | H | 2 | $(CH_2)_2$ | $C=NOCH_2C_6H_5$ | H | Cl |
| 4.109 | $CH_3$ | $CH_3$ | H | 0 | $(CH_2)_2$ | $C(CH_3)_2$ | H | Cl |
| 4.110 | $CH_3$ | $CH_3$ | H | 2 | $(CH_2)_2$ | $C(CH_3)_2$ | H | Cl |
| 4.111 | $C_2H_5$ | H | H | 0 | $(CH_2)_2$ | C=O | H | Cl |
| 4.112 | $C_2H_5$ | H | H | 2 | $(CH_2)_2$ | C=O | H | Cl |
| 4.113 | $C_2H_5$ | H | H | 0 | $(CH_2)_2$ | $CHOCH_3$ | H | Cl |
| 4.114 | $C_2H_5$ | H | H | 2 | $(CH_2)_2$ | $CHOCH_3$ | H | Cl |
| 4.115 | $C_2H_5$ | H | H | 0 | $(CH_2)_2$ | $CHOC_2H_5$ | H | Cl |
| 4.116 | $C_2H_5$ | H | H | 2 | $(CH_2)_2$ | $CHOC_2H_5$ | H | Cl |
| 4.117 | $C_2H_5$ | H | H | 0 | $(CH_2)_2$ | CHOiPr | H | Cl |
| 4.118 | $C_2H_5$ | H | H | 2 | $(CH_2)_2$ | CHOiPr | H | Cl |
| 4.119 | $C_2H_5$ | H | H | 0 | $(CH_2)_2$ | CHOH | H | Cl |
| 4.120 | $C_2H_5$ | H | H | 2 | $(CH_2)_2$ | CHOH | H | Cl |
| 4.121 | $C_2H_5$ | H | H | 0 | $(CH_2)_2$ | $C=NOCH_3$ | H | Cl |
| 4.122 | $C_2H_5$ | H | H | 2 | $(CH_2)_2$ | $C=NOCH_3$ | H | Cl |
| 4.123 | $C_2H_5$ | H | H | 0 | $(CH_2)_2$ | $C=NOC_2H_5$ | H | Cl |
| 4.124 | $C_2H_5$ | H | H | 2 | $(CH_2)_2$ | $C=NOC_2H_5$ | H | C1 |
| 4.125 | $C_2H_5$ | H | H | 0 | $(CH_2)_2$ | C=NOiPr | H | Cl |
| 4.126 | $C_2H_5$ | H | H | 2 | $(CH_2)_2$ | C=NOiPr | H | Cl |
| 4.127 | $C_2H_5$ | H | H | 0 | $(CH_2)_2$ | $C=NOCH_2CH=CHCl$ | H | Cl |
| 4.128 | $C_2H_5$ | H | H | 2 | $(CH_2)_2$ | $C=NOCH_2CH=CHCl$ | H | Cl |
| 4.129 | $C_2H_5$ | H | H | 0 | $(CH_2)_2$ | $C=NOCH_2C_6H_5$ | H | Cl |
| 4.130 | $C_2H_5$ | H | H | 2 | $(CH_2)_2$ | $C=NOCH_2C_6H_5$ | H | Cl |
| 4.131 | $C_2H_5$ | H | H | 0 | $(CH_2)_2$ | $C(CH_3)_2$ | H | Cl |
| 4.132 | $C_2H_5$ | H | H | 2 | $(CH_2)_2$ | $C(CH_3)_2$ | H | Cl |
| 4.133 | $CH_3$ | $CH_3$ | H | 0 | $(CH_2)_2$ | C=O | H | $CH_3$ |
| 4.134 | $CH_3$ | $CH_3$ | H | 2 | $(CH_2)_2$ | C=O | H | $CH_3$ |
| 4.135 | $CH_3$ | $CH_3$ | H | 0 | $(CH_2)_2$ | $CHOCH_3$ | H | $CH_3$ |
| 4.136 | $CH_3$ | $CH_3$ | H | 2 | $(CH_2)_2$ | $CHOCH_3$ | H | $CH_3$ |
| 4.137 | $CH_3$ | $CH_3$ | H | 0 | $(CH_2)_2$ | $CHOC_2H_5$ | H | $CH_3$ |
| 4.138 | $CH_3$ | $CH_3$ | H | 2 | $(CH_2)_2$ | $CHOC_2H_5$ | H | $CH_3$ |
| 4.139 | $CH_3$ | $CH_3$ | H | 0 | $(CH_2)_2$ | CHOiPr | H | $CH_3$ |
| 4.140 | $CH_3$ | $CH_3$ | H | 2 | $(CH_2)_2$ | CHOiPr | H | $CH_3$ |
| 4.141 | $CH_3$ | $CH_3$ | H | 0 | $(CH_2)_2$ | CHOH | H | $CH_3$ |
| 4.142 | $CH_3$ | $CH_3$ | H | 2 | $(CH_2)_2$ | CHOH | H | $CH_3$ |
| 4.143 | $CH_3$ | $CH_3$ | H | 0 | $(CH_2)_2$ | $C=NOCH_3$ | H | $CH_3$ |
| 4.144 | $CH_3$ | $CH_3$ | H | 2 | $(CH_2)_2$ | $C=NOCH_3$ | H | $CH_3$ |
| 4.145 | $CH_3$ | $CH_3$ | H | 0 | $(CH_2)_2$ | $C=NOC_2H_5$ | H | $CH_3$ |
| 4.146 | $CH_3$ | $CH_3$ | H | 2 | $(CH_2)_2$ | $C=NOC_2H_5$ | H | $CH_3$ |
| 4.147 | $CH_3$ | $CH_3$ | H | 0 | $(CH_2)_2$ | C=NOiPr | H | $CH_3$ |
| 4.148 | $CH_3$ | $CH_3$ | H | 2 | $(CH_2)_2$ | C=NOiPr | H | $CH_3$ |
| 4.149 | $CH_3$ | $CH_3$ | H | 0 | $(CH_2)_2$ | $C=NOCH_2CH=CHCl$ | H | $CH_3$ |
| 4.150 | $CH_3$ | $CH_3$ | H | 2 | $(CH_2)_2$ | $C=NOCH_2CH=CHCl$ | H | $CH_3$ |

TABLE 4-continued

Compounds of the formula

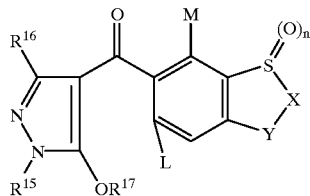

| No. | $R^{15}$ | $R^{16}$ | $R^{17}$ | n | X | Y | M | L |
|---|---|---|---|---|---|---|---|---|
| 4.151 | $CH_3$ | $CH_3$ | H | 0 | $(CH_2)_2$ | $C=NOCH_2C_6H_5$ | H | $CH_3$ |
| 4.152 | $CH_3$ | $CH_3$ | H | 2 | $(CH_2)_2$ | $C=NOCH_2C_6H_5$ | H | $CH_3$ |
| 4.153 | $CH_3$ | $CH_3$ | H | 0 | $(CH_2)_2$ | $C(CH_3)_2$ | H | $CH_3$ |
| 4.154 | $CH_3$ | $CH_3$ | H | 2 | $(CH_2)_2$ | $C(CH_3)_2$ | H | $CH_3$ |
| 4.155 | $C_2H_5$ | H | H | 0 | $(CH_2)_2$ | $C=O$ | H | $CH_3$ |
| 4.156 | $C_2H_5$ | H | H | 2 | $(CH_2)_2$ | $C=O$ | H | $CH_3$ |
| 4.157 | $C_2H_5$ | H | H | 0 | $(CH_2)_2$ | $CHOCH_3$ | H | $CH_3$ |
| 4.158 | $C_2H_5$ | H | H | 2 | $(CH_2)_2$ | $CHOCH_3$ | H | $CH_3$ |
| 4.159 | $C_2H_5$ | H | H | 0 | $(CH_2)_2$ | $CHOC_2H_5$ | H | $CH_3$ |
| 4.160 | $C_2H_5$ | H | H | 2 | $(CH_2)_2$ | $CHOC_2H_5$ | H. | $CH_3$ |
| 4.161 | $C_2H_5$ | H | H | 0 | $(CH_2)_2$ | $CHOiPr$ | H | $CH_3$ |
| 4.162 | $C_2H_5$ | H | H | 2 | $(CH_2)_2$ | $CHOiPr$ | H | $CH_3$ |
| 4.163 | $C_2H_5$ | H | H | 0 | $(CH_2)_2$ | $CHOH$ | H | $CH_3$ |
| 4.164 | $C_2H_5$ | H | H | 2 | $(CH_2)_2$ | $CHOH$ | H | $CH_3$ |
| 4.165 | $C_2H_5$ | H | H | 0 | $(CH_2)_2$ | $C=NOCH_3$ | H | $CH_3$ |
| 4.166 | $C_2H_5$ | H | H | 2 | $(CH_2)_2$ | $C=NOCH_3$ | H | $CH_3$ |
| 4.167 | $C_2H_5$ | H | H | 0 | $(CH_2)_2$ | $C=NOC_2H_5$ | H | $CH_3$ |
| 4.168 | $C_2H_5$ | H | H | 2 | $(CH_2)_2$ | $C=NOC_2H_5$ | H | $CH_3$ |
| 4.169 | $C_2H_5$ | H | H | 0 | $(CH_2)_2$ | $C=NOiPr$ | H | $CH_3$ |
| 4.170 | $C_2H_5$ | H | H | 2 | $(CH_2)_2$ | $C=NOiPr$ | H | $CH_3$ |
| 4.171 | $C_2H_5$ | H | H | 0 | $(CH_2)_2$ | $C=NOCH_2CH=CHCl$ | H | $CH_3$ |
| 4.172 | $C_2H_5$ | H | H | 2 | $(CH_2)_2$ | $C=NOCH_2CH=CHCl$ | H | $CH_3$ |
| 4.173 | $C_2H_5$ | H | H | 0 | $(CH_2)_2$ | $C=NOCH_2C_6H_5$ | H | $CH_3$ |
| 4.174 | $C_2H_5$ | H | H | 2 | $(CH_2)_2$ | $C=NOCH_2C_6H_5$ | H | $CH_3$ |
| 4.175 | $C_2H_5$ | H | H | 0 | $(CH_2)_2$ | $C(CH_3)_2$ | H | $CH_3$ |
| 4.176 | $C_2H_5$ | H | H | 2 | $(CH_2)_2$ | $C(CH_3)_2$ | H | $CH_3$ |
| 4.177 | $CH_3$ | $CH_3$ | $p-CH_3-C_6H_4-SO_2-$ | 0 | $(CH_2)_2$ | $C=O$ | H | $CH_3$ |
| 4.178 | $CH_3$ | $CH_3$ | $p-CH_3-C_6H_4-SO_2-$ | 2 | $(CH_2)_2$ | $C=O$ | H | $CH_3$ |
| 4.179 | $CH_3$ | $CH_3$ | $p-CH_3-C_6H_4-SO_2-$ | 0 | $(CH_2)_2$ | $CHOCH_3$ | H | $CH_3$ |
| 4.180 | $CH_3$ | $CH_3$ | $p-CH_3-C_6H_4-SO_2-$ | 2 | $(CH_2)_2$ | $CHOCH_3$ | H | $CH_3$ |
| 4.181 | $CH_3$ | $CH_3$ | $p-CH_3-C_6H_4-SO_2-$ | 0 | $(CH_2)_2$ | $CHOC_2H_5$ | H | $CH_3$ |
| 4.182 | $CH_3$ | $CH_3$ | $p-CH_3-C_6H_4-SO_2-$ | 2 | $(CH_2)_2$ | $CHOC_2H_5$ | H | $CH_3$ |
| 4.183 | $CH_3$ | $CH_3$ | $p-CH_3-C_6H_4-SO_2-$ | 0 | $(CH_2)_2$ | $CHOiPr$ | H | $CH_3$ |
| 4.184 | $CH_3$ | $CH_3$ | $p-CH_3-C_6H_4-SO_2-$ | 2 | $(CH_2)_2$ | $CHOiPr$ | H | $CH_3$ |
| 4.185 | $CH_3$ | $CH_3$ | $p-CH_3-C_6H_4-SO_2-$ | 0 | $(CH_2)_2$ | $CHOH$ | H | $CH_3$ |
| 4.186 | $CH_3$ | $CH_3$ | $p-CH_3-C_6H_4-SO_2-$ | 2 | $(CH_2)_2$ | $CHOH$ | H | $CH_3$ |
| 4.187 | $CH_3$ | $CH_3$ | $p-CH_3-C_6H_4-SO_2-$ | 0 | $(CH_2)_2$ | $C=NOCH_3$ | H | $CH_3$ |
| 4.188 | $CH_3$ | $CH_3$ | $p-CH_3-C_6H_4-SO_2-$ | 2 | $(CH_2)_2$ | $C=NOCH_3$ | H | $CH_3$ |
| 4.189 | $CH_3$ | $CH_3$ | $p-CH_3-C_6H_4-SO_2-$ | 0 | $(CH_2)_2$ | $C=NOC_2H_5$ | H | $CH_3$ |
| 4.190 | $CH_3$ | $CH_3$ | $p-CH_3-C_6H_4-SO_2-$ | 2 | $(CH_2)_2$ | $C=NOC_2H_5$ | H | $CH_3$ |
| 4.191 | $CH_3$ | $CH_3$ | $p-CH_3-C_6H_4-SO_2-$ | 0 | $(CH_2)_2$ | $C=NOiPr$ | H | $CH_3$ |
| 4.192 | $CH_3$ | $CH_3$ | $p-CH_3-C_6H_4-SO_2-$ | 2 | $(CH_2)_2$ | $C=NOiPr$ | H | $CH_3$ |
| 4.193 | $CH_3$ | $CH_3$ | $p-CH_3-C_6H_4-SO_2-$ | 0 | $(CH_2)_2$ | $C=NOCH_2CH=CHCl$ | H | $CH_3$ |
| 4.194 | $CH_3$ | $CH_3$ | $p-CH_3-C_6H_4-SO_2-$ | 2 | $(CH_2)_2$ | $C=NOCH_2CH=CHCl$ | H | $CH_3$ |
| 4.195 | $CH_3$ | $CH_3$ | $p-CH_3-C_6H_4-SO_2-$ | 0 | $(CH_2)_2$ | $C=NOCH_2C_6H_5$ | H | $CH_3$ |
| 4.196 | $CH_3$ | $CH_3$ | $p-CH_3-C_6H_4-SO_2-$ | 2 | $(CH_2)_2$ | $C=NOCH_2C_6H_5$ | H | $CH_3$ |
| 4.197 | $CH_3$ | $CH_3$ | $p-CH_3-C_6H_4-SO_2-$ | 0 | $(CH_2)_2$ | $C(CH_3)_2$ | H | $CH_3$ |
| 4.198 | $CH_3$ | $CH_3$ | $p-CH_3-C_6H_4-SO_2-$ | 2 | $(CH_2)_2$ | $C(CH_3)_2$ | H | $CH_3$ |
| 4.199 | $C_2H_5$ | H | $p-CH_3-C_6H_4-SO_2-$ | 0 | $(CH_2)_2$ | $C=O$ | H | $CH_3$ |
| 4.200 | $C_2H_5$ | H | $p-CH_3-C_6H_4-SO_2-$ | 2 | $(CH_2)_2$ | $C=O$ | H | $CH_3$ |
| 4.201 | $C_2H_5$ | H | $p-CH_3-C_6H_4-SO_2-$ | 0 | $(CH_2)_2$ | $CHOCH_3$ | H | $CH_3$ |
| 4.202 | $C_2H_5$ | H | $p-CH_3-C_6H_4-SO_2-$ | 2 | $(CH_2)_2$ | $CHOCH_3$ | H | $CH_3$ |
| 4.203 | $C_2H_5$ | H | $p-CH_3-C_6H_4-SO_2-$ | 0 | $(CH_2)_2$ | $CHOC_2H_5$ | H | $CH_3$ |
| 4.204 | $C_2H_5$ | H | $p-CH_3-C_6H_4-SO_2-$ | 2 | $(CH_2)_2$ | $CHOC_2H_5$ | H | $CH_3$ |
| 4.205 | $C_2H_5$ | H | $p-CH_3-C_6H_4-SO_2-$ | 0 | $(CH_2)_2$ | $CHOiPr$ | H | $CH_3$ |
| 4.206 | $C_2H_5$ | H | $p-CH_3-C_6H_4-SO_2-$ | 2 | $(CH_2)_2$ | $CHOiPr$ | H | $CH_3$ |
| 4.207 | $C_2H_5$ | H | $p-CH_3-C_6H_4-SO_2-$ | 0 | $(CH_2)_2$ | $CHOH$ | H | $CH_3$ |
| 4.208 | $C_2H_5$ | H | $p-CH_3-C_6H_4-SO_2-$ | 2 | $(CH_2)_2$ | $CHOH$ | H | $CH_3$ |
| 4.209 | $C_2H_5$ | H | $p-CH_3-C_6H_4-SO_2-$ | 0 | $(CH_2)_2$ | $C=NOCH_3$ | H | $CH_3$ |
| 4.210 | $C_2H_5$ | H | $p-CH_3-C_6H_4-SO_2-$ | 2 | $(CH_2)_2$ | $C=NOCH_3$ | H | $CH_3$ |
| 4.211 | $C_2H_5$ | H | $p-CH_3-C_6H_4-SO_2-$ | 0 | $(CH_2)_2$ | $C=NOC_2H_5$ | H | $CH_3$ |
| 4.212 | $C_2H_5$ | H | $p-CH_3-C_6H_4-SO_2-$ | 2 | $(CH_2)_2$ | $C=NOC_2H_5$ | H | $CH_3$ |
| 4.213 | $C_2H_5$ | H | $p-CH_3-C_6H_4-SO_2-$ | 0 | $(CH_2)_2$ | $C=NOiPr$ | H | $CH_3$ |

TABLE 4-continued

Compounds of the formula

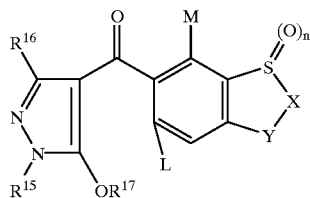

| No. | $R^{15}$ | $R^{16}$ | $R^{17}$ | n | X | Y | M | L |
|---|---|---|---|---|---|---|---|---|
| 4.214 | $C_2H_5$ | H | p-$CH_3$—$C_6H_4$—$SO_2$— | 2 | $(CH_2)_2$ | C=NOiPr | H | $CH_3$ |
| 4.215 | $C_2H_5$ | H | p-$CH_3$—$C_6H_4$—$SO_2$— | 0 | $(CH_2)_2$ | C=NOCH$_2$CH=CHCl | H | $CH_3$ |
| 4.216 | $C_2H_5$ | H | p-$CH_3$—$C_6H_4$—$SO_2$— | 2 | $(CH_2)_2$ | C=NOCH$_2$CH=CHCl | H | $CH_3$ |
| 4.217 | $C_2H_5$ | H | p-$CH_3$—$C_6H_4$—$SO_2$— | 0 | $(CH_2)_2$ | C=NOCH$_2$C$_6$H$_5$ | H | $CH_3$ |
| 4.218 | $C_2H_5$ | H | p-$CH_3$—$C_6H_4$—$SO_2$— | 2 | $(CH_2)_2$ | C=NOCH$_2$C$_6$H$_5$ | H | $CH_3$ |
| 4.219 | $C_2H_5$ | H | p-$CH_3$—$C_6H_4$—$SO_2$— | 0 | $(CH_2)_2$ | C(CH$_3$)$_2$ | H | $CH_3$ |
| 4.220 | $C_2H_5$ | H | p-$CH_3$—$C_6H_4$—$SO_2$— | 2 | $(CH_2)_2$ | C(CH$_3$)$_2$ | H | $CH_3$ |
| 4.221 | $CH_3$ | $CH_3$ | H | 0 | $(CH_2)_2$ | CH—NHCH$_3$ | H | $CH_3$ |
| 4.222 | $CH_3$ | $CH_3$ | H | 2 | $(CH_2)_2$ | CH—NHCH$_3$ | H | $CH_3$ |
| 4.223 | $CH_3$ | $CH_3$ | H | 0 | $(CH_2)_2$ | CH—NHC$_2$H$_5$ | H | $CH_3$ |
| 4.224 | $CH_3$ | $CH_3$ | H | 2 | $(CH_2)_2$ | CH—NHC$_2$H$_5$ | H | $CH_3$ |
| 4.225 | $CH_3$ | $CH_3$ | H | 0 | $(CH_2)_2$ | CH—N(CH$_3$)$_2$ | H | $CH_3$ |
| 4.226 | $CH_3$ | $CH_3$ | H | 2 | $(CH_2)_2$ | CH—N(CH$_3$)$_2$ | H | $CH_3$ |
| 4.227 | $CH_3$ | $CH_3$ | H | 0 | $(CH_2)_2$ | CH—NHOC$_2$H$_5$ | H | $CH_3$ |
| 4.228 | $CH_3$ | $CH_3$ | H | 2 | $(CH_2)_2$ | CH—NHOC$_2$H$_5$ | H | $CH_3$ |
| 4.229 | $CH_3$ | $CH_3$ | H | 0 | $(CH_2)_2$ | CH—N(CH$_3$)OC$_2$H$_5$ | H | $CH_3$ |
| 4.230 | $CH_3$ | $CH_3$ | H | 2 | $(CH_2)_2$ | CH—N(CH$_3$)OC$_2$H$_5$ | H | $CH_3$ |
| 4.231 | $CH_3$ | $CH_3$ | H | 0 | $(CH_2)_2$ | C=N—NH$_2$ | H | $CH_3$ |
| 4.232 | $CH_3$ | $CH_3$ | H | 2 | $(CH_2)_2$ | C=N—NH$_2$ | H | $CH_3$ |
| 4.233 | $CH_3$ | $CH_3$ | H | 0 | $(CH_2)_2$ | C=N—N(CH$_3$)$_2$ | H | $CH_3$ |
| 4.234 | $CH_3$ | $CH_3$ | H | 2 | $(CH_2)_2$ | C=N—N(CH$_3$)$_2$ | H | $CH_3$ |
| 4.235 | $CH_3$ | $CH_3$ | H | 0 | $(CH_2)_2$ | C(CH$_3$)—OCH$_3$ | H | $CH_3$ |
| 4.236 | $CH_3$ | $CH_3$ | H | 2 | $(CH_2)_2$ | C(CH$_3$)—OCH$_3$ | H | $CH_3$ |
| 4.237 | $CH_3$ | $CH_3$ | H | 0 | $(CH_2)_2$ | O | H | $CH_3$ |
| 4.238 | $CH_3$ | $CH_3$ | H | 2 | $(CH_2)_2$ | O | H | $CH_3$ |
| 4.239 | $C_2H_5$ | H | H | 0 | $(CH_2)_2$ | CH—NHCH$_3$ | H | $CH_3$ |
| 4.240 | $C_2H_5$ | H | H | 2 | $(CH_2)_2$ | CH—NHCH$_3$ | H | $CH_3$ |
| 4.241 | $C_2H_5$ | H | H | 0 | $(CH_2)_2$ | CH—NHC$_2$H$_5$ | H | $CH_3$ |
| 4.242 | $C_2H_5$ | H | H | 2 | $(CH_2)_2$ | CH—NHC$_2$H$_5$ | H | $CH_3$ |
| 4.243 | $C_2H_5$ | H | H | 0 | $(CH_2)_2$ | CH—N(CH$_3$)$_2$ | H | $CH_3$ |
| 4.244 | $C_2H_5$ | H | H | 2 | $(CH_2)_2$ | CH—N(CH$_3$)$_2$ | H | $CH_3$ |
| 4.245 | $C_2H_5$ | H | H | 0 | $(CH_2)_2$ | CH—NHOC$_2$H$_5$ | H | $CH_3$ |
| 4.246 | $C_2H_5$ | H | H | 2 | $(CH_2)_2$ | CH—NHOC$_2$H$_5$ | H | $CH_3$ |
| 4.247 | $C_2H_5$ | H | H | 0 | $(CH_2)_2$ | CH—N(CH$_3$)OC$_2$H$_5$ | H | $CH_3$ |
| 4.248 | $C_2H_5$ | H | H | 2 | $(CH_2)_2$ | CH—N(CH$_3$)OC$_2$H$_5$ | H | $CH_3$ |
| 4.249 | $C_2H_5$ | H | H | 0 | $(CH_2)_2$ | C=N—NH$_2$ | H | $CH_3$ |
| 4.250 | $C_2H_5$ | H | H | 2 | $(CH_2)_2$ | C=N—NH$_2$ | H | $CH_3$ |
| 4.251 | $C_2H_5$ | H | H | 0 | $(CH_2)_2$ | C=N—N(CH$_3$)$_2$ | H | $CH_3$ |
| 4.252 | $C_2H_5$ | H | H | 2 | $(CH_2)_2$ | C=N—N(CH$_3$)$_2$ | H | $CH_3$ |
| 4.253 | $C_2H_5$ | H | H | 0 | $(CH_2)_2$ | C(CH$_3$)—OCH$_3$ | H | $CH_3$ |
| 4.254 | $C_2H_5$ | H | H | 2 | $(CH_2)_2$ | C(CH$_3$)—OCH$_3$ | H | $CH_3$ |
| 4.255 | $C_2H_5$ | H | H | 0 | $(CH_2)_2$ | O | H | $CH_3$ |
| 4.256 | $C_2H_5$ | H | H | 2 | $(CH_2)_2$ | O | H | $CH_3$ |
| 4.257 | $CH_3$ | $CH_3$ | H | 0 | $(CH_2)_2$ | CH—NHCH$_3$ | H | Cl |
| 4.258 | $CH_3$ | $CH_3$ | H | 2 | $(CH_2)_2$ | CH—NHCH$_3$ | H | Cl |
| 4.259 | $CH_3$ | $CH_3$ | H | 0 | $(CH_2)_2$ | CH—NHC$_2$H$_5$ | H | Cl |
| 4.260 | $CH_3$ | $CH_3$ | H | 2 | $(CH_2)_2$ | CH—NHC$_2$H$_5$ | H | Cl |
| 4.261 | $CH_3$ | $CH_3$ | H | 0 | $(CH_2)_2$ | CH—N(CH$_3$)$_2$ | H | Cl |
| 4.262 | $CH_3$ | $CH_3$ | H | 2 | $(CH_2)_2$ | CH—N(CH$_3$)$_2$ | H | Cl |
| 4.263 | $CH_3$ | $CH_3$ | H | 0 | $(CH_2)_2$ | CH—NHOC$_2$H$_5$ | H | Cl |
| 4.264 | $CH_3$ | $CH_3$ | H | 2 | $(CH_2)_2$ | CH—NHOC$_2$H$_5$ | H | Cl |
| 4.265 | $CH_3$ | $CH_3$ | H | 0 | $(CH_2)_2$ | CH—N(CH$_3$)OC$_2$H$_5$ | H | Cl |
| 4.266 | $CH_3$ | $CH_3$ | H | 2 | $(CH_2)_2$ | CH—N(CH$_3$)OC$_2$H$_5$ | H | Cl |
| 4.267 | $CH_3$ | $CH_3$ | H | 0 | $(CH_2)_2$ | C=N—NH$_2$ | H | Cl |
| 4.268 | $CH_3$ | $CH_3$ | H | 2 | $(CH_2)_2$ | C=N—NH$_2$ | H | Cl |
| 4.269 | $CH_3$ | $CH_3$ | H | 0 | $(CH_2)_2$ | C=N—N(CH$_3$)$_2$ | H | Cl |
| 4.270 | $CH_3$ | $CH_3$ | H | 2 | $(CH_2)_2$ | C=N—N(CH$_3$)$_2$ | H | Cl |
| 4.271 | $CH_3$ | $CH_3$ | H | 0 | $(CH_2)_2$ | C(CH$_3$)—OCH$_3$ | H | Cl |
| 4.272 | $CH_3$ | $CH_3$ | H | 2 | $(CH_2)_2$ | C(CH$_3$)—OCH$_3$ | H | Cl |
| 4.273 | $CH_3$ | $CH_3$ | H | 0 | $(CH_2)_2$ | O | H | Cl |
| 4.274 | $CH_3$ | $CH_3$ | H | 2 | $(CH_2)_2$ | O | H | Cl |
| 4.275 | $C_2H_5$ | H | H | 0 | $(CH_2)_2$ | CH—NHCH$_3$ | H | Cl |
| 4.276 | $C_2H_5$ | H | H | 2 | $(CH_2)_2$ | CH—NHCH$_3$ | H | Cl |

TABLE 4-continued

Compounds of the formula

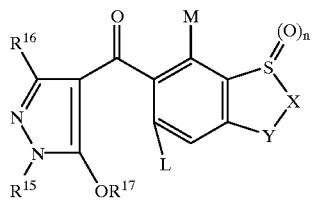

| No. | R$^{15}$ | R$^{16}$ | R$^{17}$ | n | X | Y | M | L |
|---|---|---|---|---|---|---|---|---|
| 4.277 | C$_2$H$_5$ | H | H | 0 | (CH$_2$)$_2$ | CH—NHC$_2$H$_5$ | H | Cl |
| 4.278 | C$_2$H$_5$ | H | H | 2 | (CH$_2$)$_2$ | CH—NHC$_2$H$_5$ | H | Cl |
| 4.279 | C$_2$H$_5$ | H | H | 0 | (CH$_2$)$_2$ | CH—N(CH$_3$)$_2$ | H | Cl |
| 4.280 | C$_2$H$_5$ | H | H | 2 | (CH$_2$)$_2$ | CH—N(CH$_3$)$_2$ | H | Cl |
| 4.281 | C$_2$H$_5$ | H | H | 0 | (CH$_2$)$_2$ | CH—NHOC$_2$H$_5$ | H | Cl |
| 4.282 | C$_2$H$_5$ | H | H | 2 | (CH$_2$)$_2$ | CH—NHOC$_2$H$_5$ | H | Cl |
| 4.283 | C$_2$H$_5$ | H | H | 0 | (CH$_2$)$_2$ | CH—N(CH$_3$)OC$_2$H$_5$ | H | Cl |
| 4.284 | C$_2$H$_5$ | H | H | 2 | (CH$_2$)$_2$ | CH—N(CH$_3$)OC$_2$H$_5$ | H | Cl |
| 4.285 | C$_2$H$_5$ | H | H | 0 | (CH$_2$)$_2$ | C=N—NH$_2$ | H | Cl |
| 4.286 | C$_2$H$_5$ | H | H | 2 | (CH$_2$)$_2$ | C=N—NH$_2$ | H | Cl |
| 4.287 | C$_2$H$_5$ | H | H | 0 | (CH$_2$)$_2$ | C=N—N(CH$_3$)$_2$ | H | Cl |
| 4.288 | C$_2$H$_5$ | H | H | 2 | (CH$_2$)$_2$ | C=N—N(CH$_3$)$_2$ | H | Cl |
| 4.289 | C$_2$H$_5$ | H | H | 0 | (CH$_2$)$_2$ | C(CH$_3$)—OCH$_3$ | H | Cl |
| 4.290 | C$_2$H$_5$ | H | H | 2 | (CH$_2$)$_2$ | C(CH$_3$)—OCH$_3$ | H | Cl |
| 4.291 | C$_2$H$_5$ | H | H | 0 | (CH$_2$)$_2$ | O | H | Cl |
| 4.292 | C$_2$H$_5$ | H | H | 2 | (CH$_2$)$_2$ | O | H | Cl |

PREPARATION EXAMPLES

A) Preparation of the Starting Materials and Intermediates 1. 3-Thio-2-methylbenzoic acid 100 g (0.66 mol) of 3-amino-2-methylbenzoic acid together with 270 g of ice and 127 ml of concentrated HCl are introduced into the reaction vessel. 45.7 g (0.66 mol) of sodium nitrite in 270 ml of water are then added dropwise at 0–10° C.

In a second vessel, 84.2 g (0.79 mol) of sodium carbonate and 106 g (0.66 mol) of potassium methyl xanthogenate are dissolved in 450 ml of water, and the solution was heated at 60–70° C. The diazonium solution is carefully added dropwise. Stirring is continued for 1 hour. 106 g (2.65 mol) of sodium hydroxide in 270 ml of water are subsequently added, the solution is stirred for a further 2 hours and acidified using hydrochloric acid, and the precipitate which forms is filtered off with suction. The solid is washed with water and dried.

Yield: 110 g (100% of theory) of 3-thio-2-methylbenzoic acid; melting point: 155° C.; $^1$H NMR (d$^6$-DMSO): δ [ppm]=13.0 (1H, bs), 7.7 (2H, m), 7.3 (1H, tr), 2.4 (3H, s).

2. Methyl 3-thio-2-methylbenzoate 110 g (0.66 mol) of 3-thio-2-methylbenzoate are dissolved in 1.6 l of methanol containing 5% of sulfuric acid, and the mixture is refluxed for 5 hours. The alcohol is subsequently distilled off, the residue is taken up in ethyl acetate, and the organic phase is washed with water and sodium carbonate solution, dried using sodium sulfate and evaporated on a rotary evaporator.

Yield: 104 g (87% of theory) of methyl 3-thio-2-methylbenzoate; $^1$H NMR (CDCl$_3$): δ [ppm]=7.6 (1H, d), 7.4 (1H, d), 7.1 (1H, d), 3.9 (3H, s), 3.4 (1H, s), 2.5 (3H, s).

3. Methyl 3-carboxyethylthio-2-methylbenzoate

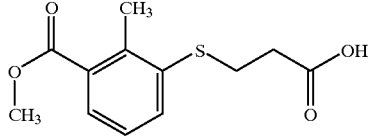

70 g (0.38 mol) of methyl 3-thio-2-methylbenzoate are dissolved in 400 ml of water and refluxed for 7 hours together with 30.8 g (0.77 mol) of sodium hydroxide solution and 58.8 g (0.45 mol) of bromopropionic acid. After cooling, the aqueous phase is washed using methyl tert-butyl ether. The aqueous phase is subsequently acidified using 2N HCl, the precipitate which has formed is filtered off with suction and washed with water, and the product is dried.

Yield: 75.5 g (78% of theory) of methyl 2-methyl-3-carboxyethylthiobenzoate; $^1$H NMR (CDCl$_3$): δ [ppm]=7.66 (1H, d), 7.51 (1H, d), 7.20 (1H, tr), 3.96 (3H, s), 3.18 (2H, tr), 2.70 (2H, tr), 2.63 (3H, s).

4. Methyl 8-methylthiochroman-4-one-7-carboxylate

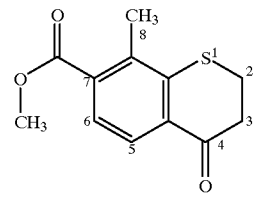

4 g (15.8 mmol) of methyl 2-methyl-3-carboxyethylthiobenzoate are stirred for 15 minutes in 40 g of polyphosphoric acid at 70° C. The reaction solution is then poured into ice-water and the precipitate which has formed is filtered off with suction. The product is washed with water and dried in a drying oven. The cyclization may give methyl 8-methylthiochromen-4-onecarboxylate, which can be removed by chromatography.

Yield: 3.1 g (83% of theory) of methyl 8-methylthiochroman-4-one-7-carboxylate; $^1$H NMR (CDCl$_3$): δ [ppm]=8.00 (1H, d), 7.30 (1H, d), 3.94 (3H, s), 3.15 (2H, m), 2.98 (2H, m), 2.50 (3H, s);

Secondary Product

Methyl 8-methylthiochromen-4-onecarboxylate: $^1$H NMR (CDCl$_3$): δ [ppm]=8.4 (1H, d), 7.9 (1H, d), 7.8 (1H, d), 7.0 (1H, d), 4.0 (3H, s), 2.7 (3H, s).

5. 8-Methylthiochroman-4-one-7-carboxylic acid 41.1 g (0.17 mol) of methyl 8-methyl thiochroman-4-one-7-carboxylate are hydrolyzed at reflux temperature in a mixture of 400 ml of water and methanol using 10.3 g (0.26 mol) of NaOH. The methanol is subsequently distilled off, and the residue is diluted with water and acidified with 2N hydrochloric acid. The product of interest precipitates and is filtered off with suction, washed with water and dried.

Yield: 34.4 g (89% of theory) of 8-methylthiochroman-4-one-7-carboxylic acid; melting point: 243–246° C.

6. 8-Methyl-1,1-dioxothiochroman-4-one-7-carboxylic acid

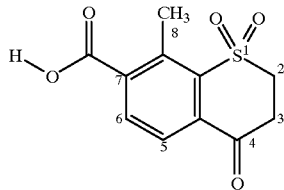

20 g (0.09 mol) of 8-methylthiochroman-4-one-7-carboxylic acid are dissolved in 100 ml of acetic acid. One spatula-tip full of sodium tungstate is added. 24.9 g (0.22 mol) of 30% strength hydrogen peroxide solution are then added dropwise at 50° C. Stirring is continued for one hour at RT. The reaction solution is then poured into water, during which process a precipitate is formed, which is filtered off with suction. The product is washed with water and then dried.

Yield: 18.4 g (80% of theory) of 8-methyl-1,1-dioxothiochroman-4-one-7-carboxylic acid; melting point: 224–225° C.

7. Methyl 4-hydroxy-8-methylthiochromane-7-carboxylate

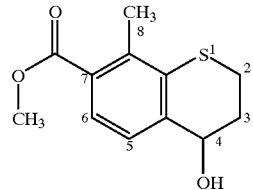

30 g (0.127 mol) of methyl 8-methylthiochroman-4-one-7-carboxylate are dissolved in a mixture of 120 ml of methylene chloride and 60 ml of methanol and the solution is cooled to 0–5° C. 2.4 g (0.064 mol) of sodium borohydride are then added a little at a time. Stirring is continued at this temperature for one hour. 200 ml of 2N hydrochloric acid are added to the reaction solution. This gives two phases. The organic phase is separated off and dried and the solvent is distilled off. The crude product is further reacted directly without further purification.

Yield: 27.6 g (91% of theory) of methyl 4-hydroxy-8-methylthiochromane-7-carboxylate.

8. Methyl 4-ethoxy-8-methylthiochromane-7-carboxylate 13.8 g (0.058 mol) of methyl 4-hydroxy-8-methylthiochromane-7-carboxylate are heated below boiling point for 4 hours in 60 ml of ethanol with 1 g of sulfuric acid added. The solvent is then distilled off and the residue is taken up in water. The aqueous phase is extracted using ethyl acetate. The organic phase is washed using sodium hydrogen carbonate solution, dried and concentrated. The product is purified by chromatography.

Yield: 10.1 g (60% of theory) of methyl 4-ethoxy-8-methylthiochromane-7-carboxylate; $^1$H NMR (CDCl$_3$): δ [ppm] =7.44 (1H, d), 7.13 (1H, d), 4.40 (1H, m), 3.90 (3H, s), 3.60 (2H, m), 3.38 (1 H, dtr), 2.90 (1H, m), 2.50 (3H, s), 2.40 (1H, m ), 1.98 (1H, m) 1.10 (3H, tr).

Methyl 4-methoxy-8-methylthiochroman-4-one-7-carboxylate and methyl 4-isopropoxy-8-methylthiochroman-4-one-7-carboxylate are obtained by a reaction similar to the above protocol, but methanol was substituted for ethanol in the case of methyl 4-methoxy-8-methylthiochroman-4-one-7-carboxylate and isopropanol for ethanol in the case of methyl 4-isopropoxy-8-methylthiochroman-4-one-7-carboxylate.

9. 4-Ethoxy-8-methylthiochromane-7-carboxylic acid 2.1 g of sodium hydroxide solution are dissolved in 20 ml of water. Methyl 4-ethoxy-8-methylthiochroman-4-one-7-carboxylate, dissolved in 20 ml of methanol, is added dropwise at about 20° C. The mixture is refcluxed for 2 hours. The solvent is subsequently distilled off and the residue poured into 2N hydrochloric acid. The aqueous phase is extracted using methylene chloride. The organic phase is dried and concentrated.

Yield: 9.3 g (100% of theory) of 4-ethoxy-8-methylthiochromane-7-carboxylic acid; melting point: 89–98° C.

The hydrolysis of the corresponding esters to obtain 4-methoxy-8-methylthiochromane-7-carboxylic acid and 4-isopropoxy-8-methylthiochromane-7-carboxylic acid proceeds similarly. The same applies to the hydrolysis of the corresponding benzo(b]thiophene derivatives given below.

10. 8-Methyl-4-ethoxy-1,1-dioxothiochromane-7-carboxylic acid 8.4 g (0.033 mol) of 4-ethoxy-8-methylthiochromane-7-carboxylic acid are introduced into 60 ml of acetic acid. one spatula-tip full of sodium tungstate is added. 7.9 g (0.07 mol) of 30% strength hydrogen peroxide solution are slowly added dropwise at 50° C. Stirring is continued for 2 hours. The reaction batch is then poured into water and the aqueous phase is extracted using ethyl acetate. The organic phase is washed using bisulfite solution and then dried and concentrated.

Yield: 9.5 g (100% of theory) of 8-methyl-4-ethoxy-1,1-dioxothiochromane-7-carboxylic acid; melting point: 150° C.

11. 8-Methylthiochroman-4-one-7-carboxylic acid O-ethyloxime

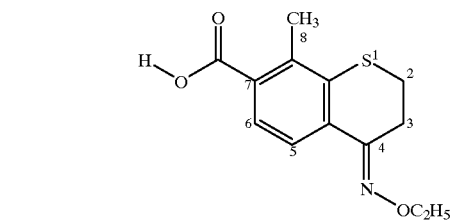

0.88 g (9 mmol) of ethylhydroxylamine are introduced into 20 ml of methanol. 0.62 g (4.5 mmol) of potassium carbonate are then added. 2.0 g (9 mmol) of 8-methylthiochroman-4-one-7-carboxylic acid are subsequently added. The reaction [sic] is stirred for 10 days at about 20° C. Work-up is carried out by adding water and 2N HCl. The precipitate which forms is filtered off with suction and dried.

Yield: 2.2 g (92% of theory) of 8-methylthiochroman-4-one-7-carboxylic acid O-ethyloxime; melting point: 166° C.

12. 8-Methyl-1,1-dioxothiochroman-4-one-7-carboxylic acid O-ethyloxime 3.0 g (0.011 mol) of 8-methylthiochroman-4-one-7-carboxylic acid O-ethyloxime together with one spatula-tip full of sodium tungstate are introduced into 30 ml of acetic acid. 2.8 g (0.024 mol) of a 30% strength hydrogen peroxide solution are added dropwise at 50° C. After the reaction mixture has been stirred for one hour, it is poured into ice-water and the precipitate which forms is filtered off with suction. The product is washed with water and dried.

Yield: 2.5 g (74% of theory) of 8-methyl-1,1-dioxothiochroman-4-one-7-carboxylic acid O-ethyloxime; melting point 198° C.

13. 8-Methyl-1-oxothiochroman-4-one-7-carboxylic acid 7.0 g (31.5 mmol) of 8-methylthiochroman-4-one-7-carboxylic acid together with one spatula-tip full of sodium tungstate are introduced into 70 ml of acetic acid. 3.6 g (31.5 mmol) of a 30% strength hydrogen peroxide solution are added dropwise at 50° C. Stirring is continued for 3 hours. The reaction solution is then stirred into water. The product is extracted using ethyl acetate. The organic phase is dried and the solvent is removed. The product is purified by chromatography.

Yield: 5.4 g (72% of theory) of 8-methyl-1-oxothiochroman-4-one-7-carboxylic acid; $^1$H NMR (d$^6$-DMSO): δ [ppm]=8.0 (2H, m), 3.5 (3H, m), 2.8 (1H, m), 2.7 (3H,s).

14. Methyl 2-methyl-3-carboxymethylthiobenzoate

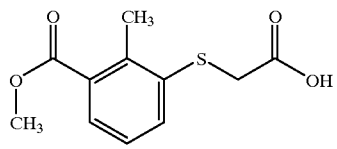

12.4 g (0.068 mol) of methyl 3-thio-2-methylbenzoate in 80 ml of dimethylformamide are added dropwise to 1.6 g (0.068 mol) of NaH in 40 ml of dimethylformamide. The mixture is stirred for 60 minutes at about 20° C. 8 g (0.068 mol) of chloroacetic acid are then added. The mixture is stirred for 4 hours at about 20° C.

Work-up is carried out by stirring the reaction mixture into ice-water/HCl.

The precipitate which forms is filtered off with suction, washed with water and dried.

Yield: 14.6 g (89% of theory) of methyl 2-methyl-3-carboxymethylthiobenzoate; $^1$H NMR (d$^6$-DMSO): δ [ppm]=7.55 (1H, d), 7.45 (1H, d), 7.21 (1H, tr), 3.82 (2H,s), 2.50 (3H,s).

15. Methyl 7-methylbenzo[b]thiophen-3[2H]-one-6-carboxylate

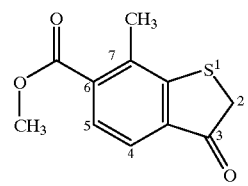

14.3 g (0.06 mmol) of 2-methyl-3-carboxymethylthiobenzoic acid are dissolved in 300 ml of methylene chloride., 13.1 g (0.11 mmol) of thionyl chloride are added dropwise. The mixture is refluxed for one hour. The solvent and excess thionyl chloride are then distilled off. The residue is taken up in 100 ml of methylene chloride and treated with 31.8 g (0.24 mmol) of aluminum trichloride. The reaction [sic] is stirred for 1 hour at about 20° C. The mixture is subsequently poured into ice-water and the organic phase is separated off. After the organic phase has been washed and dried, the solvent is removed. The product is reacted further without purification.

Yield: 12.9 g (97% of theory) of methyl 7-methyl-benzo[b]-thiophen-3[2H]-one-6-carboxylate; $^1$H NMR (CDCl$_3$): δ [ppm]=7.65 (2H, m), 3.93 (3H, s), 3.88 (2H, s), 2.50 (3H, s).

16. Methyl 7-methyl-3-hydroxybenzo[b]thiophene-[2H]-6-carboxylate

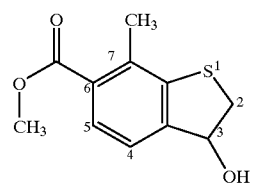

12.8 g (0.058 mol) of 7-methyl-benzo[b]thiophen-3[2H]-one-6-carboxylate are dissolved in 120 ml of methylene chloride and 60 ml of methanol and the solution is cooled to 0° C. 1.1 g (0.029 mol) of sodium borohydride are added a little at a time. The mixture is stirred for 3 hours. The reaction is stopped by adding water. The phases are separated and the aqueous phase is extracted using methylene chloride. The combined organic phases are dried. The solvent is distilled off. The crude product is reacted further.

Yield: 13.2 g (100% of theory) of methyl 7-methyl-3-hydroxybenzo-[b]thiophene-[2H]-6-carboxylate; $^1$H NMR (CDCl$_3$): δ [ppm] 7.6 (2H, m), 5.3 (1H, m), 3.9 (3H, s), 3.7 (1H, m), 3.3 (1H, m), 2.4 (3H, s).

17. Methyl 7-methyl-3-methoxybenzo[b]thiophene-[2H]-6-carboxylate 2.4 g (0.059 mol) of NaH is dissolved in 50 ml of DMF. 13.2 g of methyl 7-methyl-3-hydroxybenzo[b]thiophene-[2H]-6-carboxylate, dissolved in 50 ml [lacuna], are added dropwise. The mixture is subsequently stirred for 2 hours at about 20° C. 8.4 g (0.059 mol) of iodomethane are then added and the mixture is stirred for a further 2 hours.

The reaction solution is poured into ice-water and extracted using ethyl acetate. The organic phase is dried and subsequently concentrated. The product is purified by chromatography.

Yield: 3.5 g (25% of theory) of methyl 7-methyl-3-methoxybenzo[b]thiophene-[2H]-6-carboxylate; $^1$H NMR (CDCl$_3$): δ [ppm]=7.60 (1H, d), 7.20 (1H, d), 5.04 (1H, m), 3.90 (3H, s), 3.56 (1H, m), 3.40 (3H, s), 3.38 (1H, m), 2.50 (3H, s).

The corresponding benzothiophene acids are also obtained by methods similar to the above-described hydrolysis of the thiochromanone esters.

The compounds listed in the Tables which follow are obtained in a similar manner:

TABLE 5

Intermediates of the formula

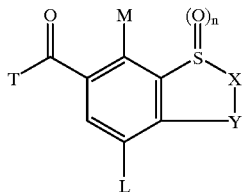

| No. | T | n | X | Y | L | M | Physical data |
|---|---|---|---|---|---|---|---|
| 5.1 | HO | 0 | (CH$_2$)$_2$ | C=O | H | H | m.p. [° C.]: 226–231 |
| 5.2 | HO | 2 | (CH$_2$)$_2$ | C=O | H | H | m.p. [° C.]: 217–220 |
| 5.3 | HO | 0 | (CH$_2$)$_2$ | C=O | H | CH$_3$ | m.p. [° C.]: 243–246 |
| 5.4 | HO | 2 | (CH$_2$)$_2$ | C=O | H | CH$_3$ | m.p. [° C.]: 224–225 |
| 5.5 | HO | 0 | (CH$_2$)$_2$ | CHOCH$_3$ | H | CH$_3$ | m.p. [° C.]: 117–118 |
| 5.6 | HO | 2 | (CH$_2$)$_2$ | CHOCH$_3$ | H | CH$_3$ | m.p. [° C.]: 167–172 |
| 5.7 | HO | 0 | (CH$_2$)$_2$ | CHOC$_2$H$_5$ | H | CH$_3$ | m.p. [° C.]: 89–98 |
| 5.8 | HO | 2 | (CH$_2$)$_2$ | CHOC$_2$H$_5$ | H | CH$_3$ | m.p. [° C.]: 150 |
| 5.9 | HO | 0 | (CH$_2$)$_2$ | CHOiPr | H | CH$_3$ | m.p. [° C.]: 138 |
| 5.10 | HO | 2 | (CH$_2$)$_2$ | CHOiPr | H | CH$_3$ | m.p. [° C.]: 142 |
| 5.11 | HO | 0 | (CH$_2$)$_2$ | C=NOC$_2$H$_5$ | H | CH$_3$ | m.p. [° C.]: 166 |
| 5.12 | HO | 2 | (CH$_2$)$_2$ | C=NOC$_2$H$_5$ | H | CH$_3$ | m.p. [° C.]: 198 |
| 5.13 | HO | 0 | (CH$_2$)$_2$ | C=NOCH$_2$CH=CHCl | H | CH$_3$ | m.p. [° C.]: 163 |
| 5.14 | HO | 2 | (CH$_2$)$_2$ | C=NOCH$_2$CH=CHCl | H | CH$_3$ | m.p. [° C.]: 174 |
| 5.15 | HO | 0 | (CH$_2$)$_2$ | C=NOCH$_2$C$_6$H$_5$ | H | CH$_3$ | m.p. [° C.]: 178 |
| 5.16 | HO | 2 | (CH$_2$)$_2$ | C=NOt-Bu | H | CH$_3$ | m.p. [° C.]: 217 |
| 5.17 | H$_3$CO | 0 | (CH$_2$)$_2$ | C(CH$_3$)$_2$ | H | CH$_3$ | m.p. [° C.]: 63–65 |
| 5.18 | HO | 2 | (CH$_2$)$_2$ | CHOCH$_3$ | H | Cl | m.p. [° C.]: 137–139 |
| 5.19 | HO | 2 | (CH$_2$)$_2$ | C=NOC$_2$H$_5$ | H | Cl | m.p. [° C.]: 205 |
| 5.20 | HO | 0 | (CH$_2$) | CHOCH$_3$ | H | CH$_3$ | $^1$H NMR, 300 MHz (d$^6$-DMSO): δ [ppm] = 13.0(1H, s), 7.55(1H, d), 7.25 (1H, d), 5.10(1H, s), 3.62(1H, m), 3.42(1H, m), 3.41(3H, s), 2.42(3H, s) |
| 5.21 | HO | 2 | (CH$_2$) | CHOCH$_3$ | H | CH$_3$ | $^1$H NMR, 300 MHz (d$^6$-DMSO): δ [ppm] = 13.5(1H, bs), 8.10(1H, d), 7.60 (1H, d), 5.18(1H, m), 4.07(1H, m), 3.75(1H, m), 3.40(3H, s), 2.70(3H, s) |
| 5.22 | HO | 2 | (CH$_2$)$_2$ | C=O | H | Cl | $^1$H NMR, 300 MHz (d$^6$-DMSO): δ [ppm] = 14.2(1H, bs), 8.10(1H, d), 7.98 (1H, d), 4.13(2H, m), 3.30 (2H, m) |
| 5.23 | HO | 0 | (CH$_2$)$_2$ | C=O | H | Cl | $^1$H NMR, 300 MHz (d$^6$-DMSO): δ [ppm] = 13.9(1H, bs), 8.10(1H, d), 7.52 (1H, d), 3.41(2H, m), 2.90 (2H, m) |
| 5.24 | H$_3$CO | 0 | (CH$_2$)$_2$ | CHOCH$_3$ | H | CH$_3$ | $^1$H NMR, 400 MHz (CDCl$_3$): δ [ppm] = 7.46, 7.13, 4.28, 3.87, 3.38, 3.30, 2.90, 2.48, 2.39, 1.91 |
| 5.25 | H$_3$CO | 0 | (CH$_2$)$_2$ | CHOC$_2$H$_5$ | H | CH$_3$ | m.p. [° C.]: 94–98 |
| 5.26 | H$_3$CO | 0 | (CH$_2$)$_2$ | CHOipropyl | H | CH$_3$ | $^1$H NMR, 250 MHz (CDCl$_3$): δ [ppm] = 7.47, 7.17, 4.48, 3.88, 3.79, 3.29, 2.90, 2.48, 2.29, 1.97, 1.21 |
| 5.27 | HO | 1 | (CH$_2$)$_2$ | C=O | H | CH$_3$ | m.p. [° C.]: 98(decomp.) |
| 5.28 | H$_3$CO | 0 | CH=CH | C=O | H | CH$_3$ | m.p. [° C.]: 128–130 |
| 5.29 | HO | 0 | CH=CH | C=O | H | CH$_3$ | $^1$H NMR, 250 MHz (d$^6$-DMSO): δ [ppm] = 13.52, 8.48, 8.30, 7.87, 7.03, 2.66 |
| 5.30 | HO | 0 | (CH$_2$)$_2$ | C=NOtbutyl | H | CH$_3$ | m.p. [° C.]: 217 |
| 5.31 | HO | 2 | (CH$_2$)$_2$ | C=NOC$_2$H$_5$ | H | Cl | m.p. [° C.]: 205 |
| 5.32 | HO | 0 | (CH$_2$)$_2$ | C(CH$_3$)$_2$ | H | CH$_3$ | m.p. [° C.]: 212 |
| 5.33 | HO | 0 | (CH$_2$)$_2$ | CH$_2$ | H | CH$_3$ | m.p. [° C.]: 155 |
| 5.34 | HO | 0 | (CH$_2$)$_2$ | CH(C$_6$H$_5$) | H | CH$_3$ | m.p. [° C.]: 175 |

TABLE 5-continued

Intermediates of the formula

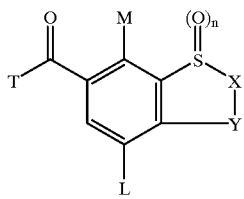

| No. | T | n | X | Y | L | M | Physical data |
|---|---|---|---|---|---|---|---|
| 5.35 | HO | 2 | (CH$_2$)$_2$ | CH$_2$ | H | CH$_3$ | m.p. [° C.]: 204 |
| 5.36 | H$_3$CO | 0 | (CH$_2$)$_2$ | CH(C$_6$H$_5$) | H | CH$_3$ | m.p. [° C.]: 103 |
| 5.37 | HO | 2 | (CH$_2$)$_2$ | CH(C$_6$H$_5$) | H | CH$_3$ | m.p. [° C.]: 145 |
| 5.38 | HO | 0 | (CH$_2$)$_2$ | CHSC$_6$H$_5$ | H | CH$_3$ | m.p. [° C.]: 77 |
| 5.39 | HO | 2 | (CH$_2$)$_2$ | CHSO$_2$C$_6$H$_5$ | H | CH$_3$ | m.p. [° C.]: 239 |
| 5.40 | HO | 0 | (CH$_2$)$_2$ | C=O | Cl | Cl | $^1$H NMR, 250 MHz (CDCl$_3$): δ [ppm] = 7.69, 3.31, 3.01 |
| 5.41 | HO | 2 | (CH$_2$)$_2$ | C=O | Cl | Cl | $^1$H NMR, 250 MHz (d$^6$-DMSO): δ [ppm] = 8.04, 4.16, 3.31 |
| 5.42 | H$_3$CO | 0 | (CH$_2$)$_2$ | CHOH | Cl | Cl | $^1$H NMR, 250 MHz (CDCl$_3$): δ [ppm] = 7.50, 5.20, 4.92, 3.36, 2.89, 2.53, 1.85 |
| 5.43 | HO | 2 | (CH$_2$)$_2$ | CHOH | Cl | Cl | $^1$H NMR, 250 MHz (d$^6$-DMSO): δ [ppm] = 8.03, 6.96, 5.08, 3.87, 3.62, 2.54, 2.37 |
| 5.44 | HO | 0 | (CH$_2$)$_2$ | CHOH | H | CH$_3$ | m.p. [° C.]: 209 |

TABLE 5a

Intermediates

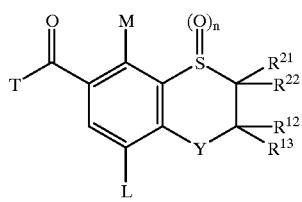

| No. | T | n | R$^{12}$ | R$^{13}$ | R$^{21}$ | R$^{22}$ | Y | L | M | Physical data |
|---|---|---|---|---|---|---|---|---|---|---|
| 5.45 | H$_3$CO | 0 | CH$_3$ | CH$_3$ | H | H | C=O | H | CH$_3$ | $^1$H NMR, 270 MHz (CDCl$_3$): δ [ppm] = 8.02, 7.50, 3.92, 3.09, 2.50, 1.33 |
| 5.46 | H$_3$CO | 0 | H | CH$_3$ | H | H | C=O | H | CH$_3$ | m.p. [° C.]: 79 |
| 5.47 | H$_3$CO | 0 | CH$_3$ | CH$_3$ | H | H | CHOCH$_3$ | H | CH$_3$ | $^1$H NMR, 270 MHz (CDCl$_3$): δ [ppm] = 7.44, 7.02, 3.89, 3.59, 3.33, 3,28, 2.50, 2.48, 1.21, 0.88 |
| 5.48 | H$_3$CO | 0 | H | H | CH$_3$ | H | C=O | H | CH$_3$ | m.p. [° C.]: 83 |
| 5.49 | H$_3$CO | 0 | H | H | CH$_3$ | H | CHOCH$_3$ | H | CH$_3$ | $^1$H NMR, 270 MHz (CDCl$_3$): δ [ppm] = 7.46, 7.11, 4.31, 3.89, 3.65, 3.37, 2.48, 2.44, 1.64, 1.44 |
| 5.50 | HO | 0 | H | CH$_3$ | H | H | CHOCH$_3$ | H | CH$_3$ | m.p. [° C.]: 124 |
| 5.51 | HO | 0 | CH$_3$ | CH$_3$ | H | H | CHOCH$_3$ | H | CH$_3$ | m.p. [° C.]: 168 |
| 5.52 | HO | 0 | H | H | CH$_3$ | H | CHOCH$_3$ | H | CH$_3$ | m.p. [° C.]: 145 |
| 5.53 | HO | 2 | H | CH$_3$ | H | H | CHOCH$_3$ (trans) | H | CH$_3$ | m.p. [° C.]: 184 |
| 5.54 | HO | 2 | CH$_3$ | CH$_3$ | H | H | CHOCH$_3$ | H | CH$_3$ | m.p. [° C.]: 161 |
| 5.55 | HO | 2 | H | H | CH$_3$ | H | CHOCH$_3$ | H | CH$_3$ | m.p. [° C.]: 182 |

Preparation of the End Products 1. 1,3-Dimethyl-4-(8-methyl-1,1-dioxothiochroman-4-one-7-carbonyl)-5-hydroxypyrazole a) 17.4 g (0.0685 mmol) of 8-methyl-1,1-dioxothiochroman-4-one-7-carboxylic acid are dissolved in 170 ml of toluene, the mixture is treated with one drop of dimethylformamide, and 8.96 g (0.0753 mol) of thionyl chloride are added. After the reaction mixture has been refluxed for 4 hours, it is concentrated. The reaction product is directly reacted further.

Yield: 18.6 g (99% of theory) of 8-methyl-1,1-dioxothiochroman-4-one-7-carbonyl chloride b) 0.82 g (7.3 mmol) of 1,3-dimethylpyrazolone and 0.74 g (7.3 mmol) of triethylamine are dissolved in 10 ml of acetonitrile. 2.0 g (7.3 mmol) of acid chloride from a), dissolved in 20 ml of acetonitrile, are added dropwise to this mixture. The mixture is stirred for one hour at room temperature. 0.42 g (4.9 mmol) of acetonecyanohydrin and 3.7 g (36.7 mmol) of triethylamine are then added. The mixture is stirred for 6 hours. work-up is carried out by adding 2N hydrochloric acid and extracting the mixture using ethyl acetate. The organic phase is then washed using sodium carbonate solution, the aqueus phase is acidified, and the precipitate which forms is filtered off with suction and dried.

Yield: 0.2 g (8% of theory) of 1,3-dimethyl-4-(8-methyl-1,1-dioxothiochroman-4-one-7-carbonyl)-5-hydroxypyrazole, melting point: 83° C.

2. 7-(1,3-dimethyl-5-hydroxypyrazole-4-carbonyl)-8-methylthiochroman-4-one O-ethyloxime

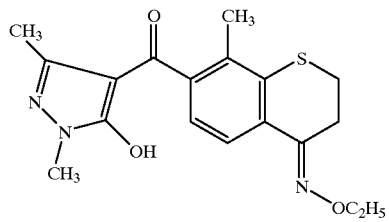

1 g (3.77 mnmol) of 7-carboxy-8-methylthiochroman-4-one O-ethyloxime are stirred for 2 hours at RT in tert-amyl alcohol together with 0.46 g (4.07 mmol) of 1,3-dimethylpyrazolone and 0.84 g (4.07 mmol) of dicyclohexylcarbodiimide (DCC). 0.78 g (5.66 mmol) of potassium carbonate are subsequently added, and the mixture is heated at 90° C. and stirred for 5 hours at this temperature. It is worked up by stirring the reaction batch into water followed by extraction using ethyl acetate. The organic phase is discarded. The uoaqueus phase is acidified using HCl and the product of interest is extracted using ethyl acetate. The extractant is removed. The product is purified by chromatography.

Yield: 0.35 g (26% of theory) of 7-(1,3-dimethyl-5-hydroxypyrazole-4-carbonyl)-8-methylthio-chroman-4-one O-ethyloxime; $^1$H NMR (CDCl$_3$): δ [ppm]=7.95 (1H, d), 6.99 (1H, d), 4.28 (2H, q), 3.69 (3H, s), 3.10 (2H, m), 2.97 (2H, m), 2.30 (3H, s), 1.75 (3H, s), 1.38 (3H, tr).

3. 7-(1,3-dimethyl-5-hydroxypyrazole-4-carbonyl)-8-methyl-1,1-dioxothiochroman 0.35 g (1 mmol) of 1,3-dimethyl-4-(8-methylthiochroman-4-one-7-carbonyl O-ethyloxime)-5-hydroxypyrazole are introduced into the reaction vessel together with 5 ml of acetic acid and one spatula tip full of sodium tungstate and the mixture is heated at 50° C. 0.24 g (2.1 mmol) of 30% strength hydrogen peroxide solution is then added and the mixture is stirred for 4 hours. Water is then added and the mixture is extracted using ethyl acetate. The organic phase is washed using thiosulfate solution and evaporated on a rotary evaporator.

Yield: 0.35 g (89% of theory) of 7-(1,3 dimethyl-5-hydroxypyrazole-4-carbonyl)-8-methyl-1,1-dioxo-thio-chroman O-ethyloxime)-5-hydroxypyrazole; $^1$H NMR (CDCl$_3$): δ [ppm]=9.90 (1H, bs), 8.12 (1H, d), 7.35 (1H, d), 4.32 (2H, q), 3.65 (3H, s), 3.44 (4H, m), 2.70 (3H, s), 1.73 (3H, s), 1.38 (3H, tr).

TABLE 6

Compounds of the formula

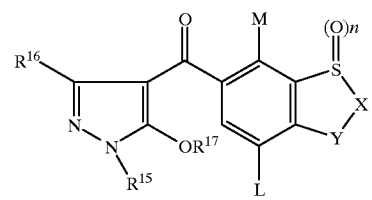

| No. | $R^{15}$ | $R^{16}$ | $R^{17}$ | n | X | Y | L | M | M.p. [° C.] |
|---|---|---|---|---|---|---|---|---|---|
| 6.1 | CH$_3$ | CH$_3$ | H | 2 | (CH$_2$)$_2$ | C=O | H | CH$_3$ | 83 |
| 6.2 | CH$_3$ | CH$_3$ | H | 2 | (CH$_2$)$_2$ | CHOCH$_3$ | H | CH$_3$ | 85 |
| 6.3 | CH$_3$ | CH$_3$ | H | 2 | (CH$_2$)$_2$ | CHOC$_2$H$_5$ | H | CH$_3$ | 75 |
| 6.4 | CH$_3$ | CH$_3$ | H | 2 | (CH$_2$)$_2$ | CHOiPr | H | CH$_3$ | 82 |
| 6.5 | CH$_3$ | CH$_3$ | H | 2 | (CH$_2$)$_2$ | C=NOC$_2$H$_5$ | H | CH$_3$ | 189–191 |
| 6.6 | C$_2$H$_5$ | H | H | 2 | (CH$_2$)$_2$ | C(CH$_3$)$_2$ | H | CH$_3$ | 89–91 |
| 6.7 | C$_2$H$_5$ | H | H | 2 | (CH$_2$)$_2$ | CHOCH$_3$ | H | CH$_3$ | 64 |
| 6.8 | C$_2$H$_5$ | H | H | 0 | CH=CH | C=O | H | CH$_3$ | 135 |
| 6.9 | C$_2$H$_5$ | H | H | 2 | (CH$_2$)$_2$ | CH$_2$ | H | CH$_3$ | 162 |
| 6.10 | C$_2$H$_5$ | H | H | 0 | (CH$_2$)$_2$ | CH(C$_6$H$_5$) | H | CH$_3$ | 132–133 |
| 6.11 | C$_2$H$_5$ | H | H | 2 | (CH$_2$)$_2$ | CH(C$_6$H$_5$) | H | CH$_3$ | 106 |

TABLE 6-continued

Compounds of the formula

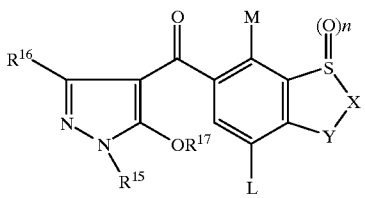

| No. | $R^{15}$ | $R^{16}$ | $R^{17}$ | n | X | Y | L | M | M.p. [° C.] |
|---|---|---|---|---|---|---|---|---|---|
| 6.12 | $C_2H_5$ | H | H | 2 | $(CH_2)_2$ | $CHNHOC_2H_5$ | H | $CH_3$ | 74 |
| 6.13 | $C_2H_5$ | H | H | 2 | $(CH_2)_2$ | $CHSO_2C_6H_5$ | H | $CH_3$ | 119 |
| 6.14 | $C_2H_5$ | R | $SO_2C_3H_7$ | 2 | $(CH_2)_2$ | $C(CH_3)_2$ | H | $CH_3$ | 93 |
| 6.15 | $C_2H_5$ | H | $SO_2$-(p-$CH_3$—$C_6H_4$) | 2 | $(CH_2)_2$ | $C(CH_3)_2$ | H | $CH_3$ | 141 (decomp.) |
| 6.16 | $C_2H_5$ | H | $SO_2C_4H_9$ | 2 | $(CH_2)_2$ | $C(CH_3)_2$ | H | $CH_3$ | $^1$H NMR(250 MHz, $CDCl_3$, δ in ppm): 7.48, 7.42, 7.37, 4.30, 4.21, 3.80, 3.47, 3.11, 2.86, 2.38, 2.04, 1.47, 1.02, 0.96 |

TABLE 7

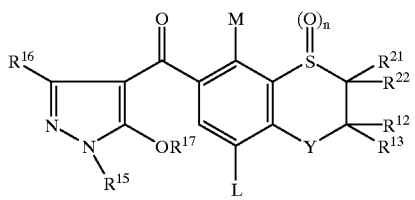

| No. | $R^{15}$ | $R^{16}$ | $R^{17}$ | n | $R^{12}$ | $R^{13}$ | $R^{21}$ | $R^{22}$ | Y | L | M | M.p. [° C.] |
|---|---|---|---|---|---|---|---|---|---|---|---|---|
| 7.1 | $C_2H_5$ | H | H | 2 | H | H | $CH_3$ | H | $CHOCH_3$ | H | $CH_3$ | 74–77 |
| 7.2 | $C_2H_5$ | H | H | 2 | H | $CH_3$ | H | H | $CHOCH_3$(cis) | H | $CH_3$ | 72 |

The compounds I and their agriculturally useful salts—both as isomer mixtures and in the form of the pure isomers—are suitable as herbicides. The herbicidal compositions comprising I effect very good control of vegetation on non-crop areas, especially at high rates of application. In crops such as wheat, rice, maize, soya beans and cotton, they act against broad-leaved weeds and grass weeds without substantially damaging the crop plants. This effect is observed mainly at low rates of application.

Taking into consideration the versatility of the application method, the compounds I or compositions comprising them can also be employed in a further number of crop plants for eliminating undesirable plants. Examples of suitable crops are the following:

*Allium cepa, Ananas comosus, Arachis hypogaea, Asparagus officinalis, Beta vulgaris* spec. altissima, *Beta vulagris* spec. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre* [sic], *Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

Moreover, the compounds I can also be used in crops which have been made tolerant to the action of herbicides by means of breeding, including genetic engineering methods.

The herbicidal compositions or the active ingredients can be applied pre- or post-emergence. If the active ingredients are less well tolerated by certain crop plants, application techniques can be used where the herbicidal compositions are sprayed, with the aid of the spraying apparatus, in such a way that the active ingredients come into as little contact as possible with the leaves of the sensitive crop plants while reaching the leaves of undesirable plants which grow underneath, or the naked soil surface (post-directed, lay-by).

The compounds I or the herbicidal compositions comprising them can be used for example in the form of ready-to-spray aqueous solutions, powders, suspensions, also highly concentrated aqueus oily or other suspensions or dispersions, emulsions, oil dispersions, pastes, dusts, materials for spreading or granules by means of spraying, atomizing, dusting, spreading or pouring. The use forms depend on the intended purposes; in any case, they should guarantee the finest possible distribution of the active ingredients according to the invention.

Suitable inert additives are mineral oil fractions of medium to high boiling point, such as kerosene or diesel oil, furthermore coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone, or strongly polar solvents such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substrates [sic], as such or dissolved in an oil or solvent, can be homogenized in water by means of wetting agent, tackifier, dispersant or emulsifier. However, it is also possible to prepare concentrates composed of active ingredient, wetting agent, tackifier, dispersant or emulsifier and, if desired, solvent or oil, and these concentrates are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin, such as cereal meal, tree bark meal, wood meal and nutshell meal, cellulose powder or other solid carriers.

The concentrations of the active ingredients I in the ready-to-use preparations can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR spectrum).

The compounds I according to the invention can be formulated for example as follows:

I. 20 parts by weight of the compound No. 6.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. 6.2 are dissolved in a mixture composed of 40 parts by weight of cyclohexanone, parts by weight of isobutanol, 20 parts by weight of the adduct of 40 mol of isooctylphenol [lacuna] and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 6.3 are dissolved in a mixture composed of 25 parts by weight of cyclohexanone, 65 parts by weight of a mineral oil fraction of boiling point 210 to 80° C. [sic] and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 6.4 are mixed thoroughly with 3 parts by weight of sodium diisobutylnaphthalene-a-sulfonate [sic], 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 6.5 are mixed with 97 parts by weight of finely divided kaolin. This gives a dust which comprises 3% by weight of the active ingredient.

VI. 20 parts by weight of the active ingredient No. 6.8 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This give a stable oily dispersion.

VII. 1 part by weight of the active ingredient No. 6.9 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active ingredient No. 6.10 is dissolved in a mixture composed of 80 parts by weight of cyclohexanone and 20 parts by weight of Wettol® EM 31 (=non-ionic emulsifier based on ethoxylated castor oil). This gives a stable emulsion concentrate.

To widen the spectrum of action and to achieve synergistic effects, the pyrazol-4-ylbenzene derivatives I may be mixed with a large number of representatives of other groups of herbicidal or growth-regulating active ingredients and then be applied together. Examples of suitable components in the mixtures are 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanedione, heteroaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazins, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, also together with further crop protection agents, for example with pesticides or agents for controlling phytopathogenic fungi or bacteria. Also of interest is the miscibility with mineral salt solutions, which are employed for treating nutrient and trace element deficiencies. Non-phytotoxic oil and oil concentrates may also be added.

Depending on the intended aim, the season, the target plants and the growth stage, the application rates are from 0.001 to 3.0, preferably 0.01 to 1.0, kg of active ingredient (a.i.)/ha.

Use Examples

The herbicidal action of the pyrazol-4-yl-benzoyl derivatives of the formula I was demonstrated by greenhouse experiments:

The culture containers used were plastic flowerpots containing loamy sand with approximately 3.0% of humus as the substrate. The seeds of the test plants were sown separately for each species.

For the pre-emergence treatment, the active ingredients which had been suspended or emulsified in water were applied directly after sowing by means of finely distributing nozzles. The containers were irrigated gently to promote germination and growth and subsequently covered with translucent plastic hoods until the plants had rooted. This cover causes uniform germination of the test plants, unless this was adversely affected by the active ingredients.

For the post-emergence treatment, the test plants were first grown to a plant height of 3 to 15 cm, depending on the growth habit, and only then treated with the active ingredients which had been suspended or emulsified in water. To this end, the test plants were either sown directly and grown in the same containers or first grown separately as seedlings and transplanted into the test containers a few days prior to treatment. The rate of application for the post-emergence treatment was 0.5 or 0.25 kg of a.i./ha.

Depending on the species, the plants were kept at from 10 to 25° C. or 20 to 35° C. The test period extended over 2 to 4 weeks. During this time, the plants were tended, and their response to the individual treatments was evaluated.

Evaluation was carried out using a scale from 0 to 100. 100 means no emergence of the plants or complete destruction of at least the aerial parts and 0 means no damage or normal course of growth.

The plants used in the greenhouse experiments were composed of the following species:

| Scientific Name | Common Name |
| --- | --- |
| Zea mays | Indian corn |
| Chenopodium album | lambsquarters (goosefoot) |
| Sinapis alba | white mustard |
| Solanum nigrum | black nightshade |

TABLE 7

Herbicidal activity when used post-emergence in the greenhouse

Ex. No. 6.3

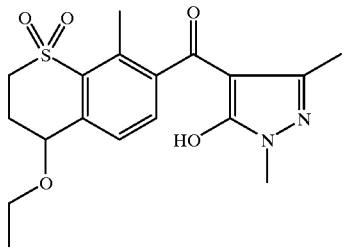

| | Rate of application (kg of a.i./ha) | |
| --- | --- | --- |
| | 0.5 | 0.25 |
| Test plants | Damage in % | |
| ZEAMX | 0 | 0 |
| CHEAL | 90 | 85 |
| SINAL | 85 | 80 |
| SOLNI | 100 | 75 |

We claim:
1. A pyrazol-4-yl-benzoyl compound of the formula I

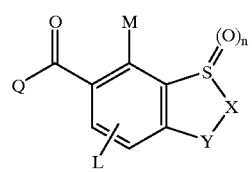

where the substituents have the following meanings:
L, M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy;
halogen, cyano, nitro, a group —$(A)_m$—$S(O)_n R^1$ or a group —$(A)_m$—CO—$R^2$;
Y is

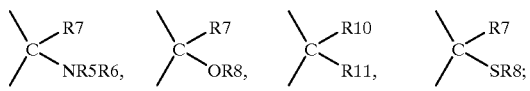

or is oxygen or sulfur;

X is $CR^{12}R^{13}$, $CR^{12}R^{13}$—$CR^{21}R^{22}$ or $CR^{12}$=$CR^{13}$;

the bond between X and Y can be saturated or unsaturated;

A is oxygen or $NR^{14}$;

m is zero or one;

n is two;

$R^1$ is $C_1$–$C_4$-alkyl, $C_1$–$C_4$-haloalkyl or $NR^{14}$;

$R^2$ is $C_1$–$C_4$-alkyl, $C_1$–$C_4$-haloalkyl, $C_1$–$C_4$-alkoxy or $NR^{14}$;

$R^3$ is hydrogen, —$NR^9R^4$;

$C_1$–$C_6$-alkyl, $C_1$–$C_6$-haloalkyl, $C_1$–$C_6$-alkoxy, $C_1$–$C_6$-haloalkoxy, $C_2$–$C_6$-alkenyl, $C_2$–$C_6$-haloalkenyl, $C_2$–$C_6$-alkynyl;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyloxy, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^4$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^9$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^5$, $R^6$ independently of one another are hydrogen, $C_1$–$C_6$-alkyl, $C_2$–$C_6$-alkenyl, $C_1$–$C_4$-haloalkyl, $C_2$–$C_6$-haloalkenyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^7$ is hydrogen, $C_1$–$C_6$-alkyl, $C_1$–$C_4$-alkoxy, $C_1$–$C_4$-haloalkyl, $C_1$–$C_4$-haloalkoxy;

unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^7$ and $R^{21}$ or $R^7$ and $R^{12}$ can form a bond;

$R^8$ is hydrogen, $C_1$–$C_6$-alkyl, $C_1$–$C_4$-haloalkyl, unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{10}$, $R^{11}$ independently of one another are hydrogen, $C_1$–$C_6$-alkyl;

unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^{10}$ and $R^{12}$ or $R^{10}$ and $R^{21}$ can form a bond;

$R^{10}$ and $R^{11}$ together can form a 1,4-dioxabutane-1,4-diyl, 1,3-dioxabutane-1,4-diyl, 1,5-dioxapentane-1,5-diyl, 1,3-dioxapentane-1,5-diyl or 2,4-dioxapentane-1,5-diyl chain which is substituted by hydrogen or $C_1$–$C_4$-alkyl;

$R^{12}$, $R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{14}$ is $C_1$–$C_4$-alkyl;

$R^{21}$ is hydrogen, $C_1$–$C_6$-alkyl, $C_1$–$C_6$-haloalkyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{22}$ is hydrogen, $C_1$–$C_6$-alkyl, $C_1$–$C_6$-haloalkyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

Q is a pyrazole ring, linked in the 4-position, of the formula II

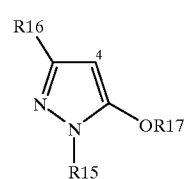

where $R^{15}$ is $C_1$–$C_4$-alkyl, $R^{16}$ is hydrogen, $C_1$–$C_4$-alkyl or $C_1$–$C_4$-haloalkyl and $R^{17}$ is hydrogen, $C_1$–$C_4$-alkylsulfonyl, phenylsulfonyl or alkylphenylsulfonyl, or an agriculturally useful salt thereof.

2. A pyrazol-4-ylbenzoyl compound of the formula Ia

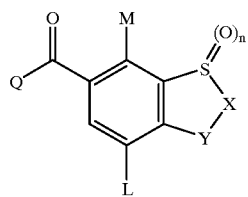

where
L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano, M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano, n is two;
X is $CR^{12}R^{13}$, $CR^{12}R^{13}$—$CR^{21}R^{22}$ or $CR^{12}$=$CR^{13}$;
Y is

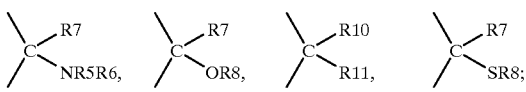

or is oxygen or sulfur;

$R^3$ is hydrogen, —$NR^9R^4$;
  $C_1$–$C_6$-alkyl, $C_1$–$C_6$-haloalkyl, $C_1$–$C_6$-alkoxy, $C_1$–$C_6$-haloalkoxy, $C_2$–$C_6$-alkenyl, $C_2$–$C_6$-haloalkenyl, $C_2$–$C_6$-alkynyl;
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
  unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
  unsubstituted or substituted benzyloxy, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^4$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
  unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^9$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
  unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^5$, $R^6$ independently of one another are hydrogen, $C_1$–$C_6$-alkyl, $C_2$–$C_6$-alkenyl, $C_1$–$C_4$-haloalkyl, $C_2$–$C_6$-haloalkenyl, $C_1$–$C_6$-alkoxy, $C_1$–$C_6$-haloalkoxy;
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
  unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^7$ is hydrogen, $C_1$–$C_6$-alkyl, $C_1$–$C_4$-alkoxy, $C_1$–$C_4$-haloalkyl, $C_1$–$C_4$-haloalkoxy;
  unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^7$ and $R^{21}$ or $R^7$ and $R^{12}$ can form a bond;

$R^8$ is hydrogen, $C_1$–$C_6$-alkyl, $C_1$–$C_4$-haloalkyl,
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
  unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{10}$, $R^{11}$ independently of one another are hydrogen, $C_1$–$C_6$-alkyl;
  unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^{10}$ and $R^{12}$ or $R^{10}$ and $R^{21}$ can form a bond;

$R^{10}$ and $R^{11}$ together can form a 1,4-dioxabutane-1,4-diyl, 1,3-dioxabutane-1,4-diyl, 1,5-dioxapentane-1,5-diyl, 1,3-dioxapentane-1,5-diyl or 2,4-dioxapentane-1,5-diyl chain which is substituted by hydrogen or $C_1$–$C_4$-alkyl;

$R^{12}$, $R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy;
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{14}$ is $C_1$–$C_4$-alkyl;

$R^{21}$ is hydrogen, $C_1$–$C_6$-alkyl, $C_1$–$C_6$-haloalkyl, $C_1$–$C_6$-alkoxy, $C_1$–$C_6$-haloalkoxy;
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{22}$ is hydrogen, $C_1$–$C_6$-alkyl, $C_1$–$C_6$-haloalkyl, $C_1$–$C_6$-alkoxy, $C_1$–$C_6$-haloalkoxy;
  unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

Q is a pyrazole ring, linked in the 4-position, of the formula II

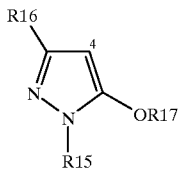

where $R^{15}$ is $C_1$–$C_4$-alkyl, $R^{16}$ is hydrogen, $C_1$–$C_4$-alkyl or $C_1$–$C_4$-haloalkyl and $R^{17}$ is hydrogen, $C_1$–$C_4$-alkylsulfonyl, phenylsulfonyl or alkylphenylsulfonyl, or an agriculturally useful salt thereof.

3. A pyrazol-4-ylbenzoyl compound of the formula Ib

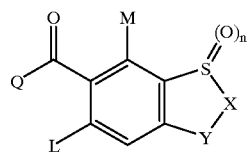

where

L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, n is two;

X is $CR^{12}R^{13}$, $CR^{12}R^{13}R^{21}R^{22}$ or $CR^{12}$=$CR^{13}$;

Y is

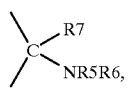 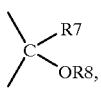 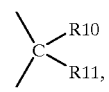 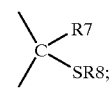

or is oxygen or sulfur;

$R^3$ is hydrogen, —$NR^9R^4$;

$C_1$–$C_6$-alkyl, $C_1$–$C_6$-haloalkyl, $C_1$–$C_6$-alkoxy, $C_1$–$C_6$-haloalkoxy, $C_2$–$C_6$-alkenyl, $C_2$–$C_6$-haloalkenyl, $C_2$–$C_6$-alkynyl;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyloxy, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^4$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^9$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^5$, $R^6$ independently of one another are hydrogen, $C_1$–$C_6$-alkyl, $C_2$–$C_6$-alkenyl, $C_1$–$C_4$-haloalkyl, $C_2$–$C_6$-haloalkenyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^7$ is hydrogen, $C_1$–$C_6$-alkyl, $C_1$–$C_4$-alkoxy, $C_1$–$C_4$-haloalkyl, $C_1$–$C_4$-haloalkoxy;

unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^7$ and $R^{21}$ or $R^7$ and $R^{12}$ can form a bond;

$R^8$ is hydrogen, $C_1$–$C_6$-alkyl, $C_1$–$C_4$-haloalkyl, unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{10}$, $R^{11}$ independently of one another are hydrogen, $C_1$–$C_6$-alkyl;

unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^{10}$ and $R^{12}$ or $R^{10}$ and $R^{21}$ can form a bond;

$R^{10}$ and $R^{11}$ together can form a 1,4-dioxabutane-1,4-diyl, 1,3-dioxabutane-1,4-diyl, 1,5-dioxapentane-1,5-diyl, 1,3-dioxapentane-1,5-diyl or 2,4-dioxapentane-1,5-diyl chain which is substituted by hydrogen or $C_1$–$C_4$-alkyl;

$R^{12}$, $R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{14}$ is $C_1$–$C_4$-alkyl;

$R^{21}$ is hydrogen, $C_1$–$C_6$-alkyl, $C_1$–$C_6$-haloalkyl, $C_1$–$C_6$-alkoxy, $C_1$–$C_6$-haloalkoxy;

unsubstituted or substituted phenyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

$R^{22}$ is hydrogen, $C_1-C_6$-alkyl, $C_1-C_6$-haloalkyl, $C_1-C_6$-alkoxy, $C_1-C_6$-haloalkoxy;

unsubstituted or substituted phenyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

Q is a pyrazole ring, linked in the 4-position, of the formula II

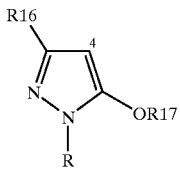

where $R^{15}$ is $C_1-C_4$-alkyl, $R^{16}$ is hydrogen, $C_1-C_4$-alkyl or $C_1-C_4$-haloalkyl and $R^{17}$ is hydrogen, $C_1-C_4$-alkylsulfonyl, phenylsulfonyl or alkylphenylsulfonyl, or an agriculturally useful salt thereof.

4. The pyrazol-4-ylbenzoyl compound of the formula I as defined in claim 1 where the radicals L and M are hydrogen, methyl, methoxy, chlorine, cyano, nitro or trifluoromethyl.

5. A pyrazol-4-ylbenzoyl compound of the formula Ic

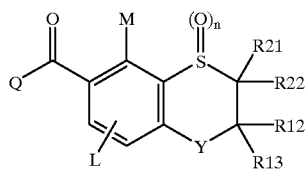

where

L is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, nitro or cyano, M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, nitro or cyano, n is two;

Y is

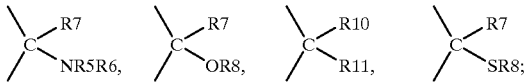

or is oxygen or sulfur;

$R^3$ is hydrogen, $-NR^9R^4$;

$C_1-C_6$-alkyl, $C_1-C_6$-haloalkyl, $C_1-C_6$-alkoxy, $C_1-C_6$-haloalkoxy, $C_2-C_6$-alkenyl, $C_2-C_6$-haloalkenyl, $C_2-C_6$-alkynyl;

unsubstituted or substituted phenyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

unsubstituted or substituted benzyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

unsubstituted or substituted benzyloxy, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

$R^4$ is hydrogen, $C_1-C_6$-alkyl, $C_1-C_6$-haloalkyl, $C_2-C_6$-alkenyl, $C_2-C_4$alkynyl, $C=O-NR^{14}$;

unsubstituted or substituted phenyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

unsubstituted or substituted benzyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

$R^9$ is hydrogen, $C_1-C_6$-alkyl, $C_1-C_6$-haloalkyl, $C_2-C_6$-alkenyl, $C_2-C_6$-alkynyl, $C=O-NR^{14}$;

unsubstituted or substituted phenyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

unsubstituted or substituted benzyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

$R^5$, $R^6$ independently of one another are hydrogen, $C_1-C_6$-alkyl, $C_2-C_6$-alkenyl, $C_1-C_4$-haloalkyl, $C_2-C_6$-haloalkenyl, $C_1-C_6$-alkoxy, $C_1-C_6$-haloalkoxy;

unsubstituted or substituted phenyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

unsubstituted or substituted benzyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

$R^7$ is hydrogen, $C_1-C_6$-alkyl, $C_1-C_4$-alkoxy, $C_1-C_4$-haloalkyl, $C_1-C_4$-haloalkoxy;

unsubstituted or substituted phenyl, wherein the substituents are selected from the group consisting of one to three halogens, $C_1-C_4$-alkyl, $C_1-C_4$-alkoxy, $C_1-C_4$-haloalkoxy and nitro;

$R^7$ and $R^{21}$ or $R^7$ and $R^{12}$ can form a bond;

$R^8$ is hydrogen, $C_1-C_6$-alkyl, $C_1-C_4$-haloalkyl, unsubstituted or substituted phenyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

unsubstituted or substituted benzyl, wherein the substituents are selected from the group consisting of $C_1-C_4$-alkyl, $C_1-C_4$-alkoxy, $C_1-C_4$-haloalkoxy, $C_1-C_4$-haloalkyl, halogen, cyano and nitro;

$R^{10}$, $R^{11}$ independently of one another are hydrogen, $C_1-C_6$-alkyl;

unsubstituted or substituted phenyl, wherein the substituents are selected from the group consisting of one to three halogens, $C_1-C_4$-alkyl, $C_1-C_4$-alkoxy, $C_1-C_4$-haloalkoxy and nitro;

$R^{10}$ and $R^{12}$ or $R^{10}$ and $R^{21}$ can form a bond;

$R^{10}$ and $R^{11}$ together can form a 1,4-dioxabutane-1,4-diyl, 1,3-dioxabutane-1,4-diyl, 1,5-dioxapentane-1,5-diyl, 1,3-dioxapentane-1,5-diyl or 2,4-dioxapentane-1,5-diyl chain which is substituted by hydrogen or $C_1-C_4$-alkyl;

$R^{12}$, $R^{13}$ independently of one another are hydrogen, $C_1-C_6$-alkyl, $C_1-C_6$-haloalkyl, $C_1-C_6$-alkoxy, $C_1-C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{14}$ is $C_1$–$C_4$-alkyl;

$R^{21}$ is hydrogen, $C_1$–$C_6$-alkyl, $C_1$–$C_6$-haloalkyl, $C_1$–$C_6$-alkoxy, $C_1$–$C_6$-haloalkoxy;
unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{22}$ is hydrogen, $C_1$–$C_6$-alkyl, $C_1$–$C_6$-haloalkyl, $C_1$–$C_6$-alkoxy, $C_1$–$C_6$-haloalkoxy;
unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

Q is a pyrazole ring, linked in the 4-position, of the formula II

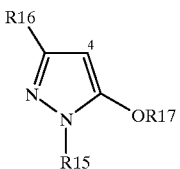

II where $R^{15}$ is $C_1$–$C_4$-alkyl, $R^{16}$ is hydrogen, $C_1$–$C_4$-alkyl or $C_1$–$C_4$-haloalkyl and $R^{17}$ is hydrogen, $C_1$–$C_4$-alkylsulfonyl, phenylsulfonyl or alkylphenylsulfonyl, or an agriculturally useful salt thereof.

6. A pyrazol-4-ylbenzoyl compound of the formula Id

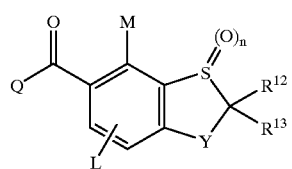

Id where

L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–C4-haloalkoxy, halogen, nitro or cyano, M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, n is zero, one or two;

Y is 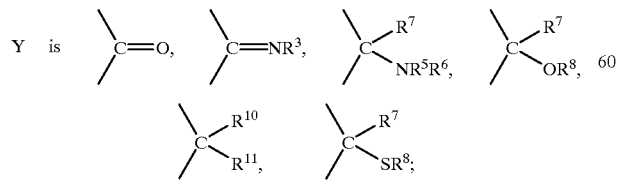

or is oxygen or sulfur;

$R^3$ is hydrogen, —$NR^9R^4$;
$C_1$–$C_6$-alkyl, $C_1$–$C_6$-haloalkyl, $C_1$–$C_6$-alkoxy, $C_1$–$C_6$-haloalkoxy, $C_2$–$C_6$-alkenyl, $C_1$–$C_6$-haloalkenyl, $C_2$–$C_6$-alkynyl;
unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
unsubstituted or substituted benzyloxy, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^4$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;
unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^9$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;
unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^5$, $R^6$ independently of one another are hydrogen, $C_1$–$C_6$-alkyl, $C_2$–$C_6$-alkenyl, $C_1$–$C_4$-haloalkyl, $C_2$–$C_6$-haloalkenyl, $C_1$–$C_6$-alkoxy, $C_1$–$C_6$-haloalkoxy;
unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^7$ is hydrogen, $C_1$–$C_6$-alkyl, $C_1$–$C_4$-alkoxy, $C_1$–$C_4$-haloalkyl, $C_1$–$C_4$-haloalkoxy;
unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^7$ and $R^{21}$ or $R^7$ and $R^{12}$ can form a bond:

$R^8$ is hydrogen, $C_1$–$C_6$-alkyl, $C_1$–$C_4$-haloalkyl,
unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{10}$, $R^{11}$ independently of one another are hydrogen, $C_1$–$C_6$-alkyl;
unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^{10}$ and $R^{12}$ or $R^{10}$ and $R^{21}$ can form a bond;

$R^{10}$ and $R^{11}$ together can form a 1,4-dioxabutane-1,4-diyl, 1,3-dioxabutane-1,4-diyl, 1,5-dioxapentane-1,5-diyl, 1,3-dioxapentane-1,5-diyl or 2,4-dioxapentane-1,5-diyl chain which is substituted by Hydrogen or $C_1$–$C_4$-alkyl;

$R^{12}$, $R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{14}$ is $C_1$–$C_4$-alkyl;

O is a pyrazole ring, linked in the 4-position, of the formula II

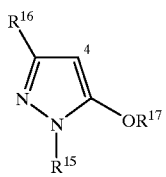

II where $R^{15}$ is $C_1$–$C_4$-alkyl, $R^{16}$ is hydrogen, $C_1$–$C_4$-alkyl or $C_1$–$C_4$-haloalkyl and $R^{17}$ is hydrogen, $C_1$–$C_4$-alkylsulfonyl, phenylsulfonyl or alkylphenylsulfonyl, or an agriculturally useful salt thereof.

7. A pyrazol-4-ylbenzoyl compound of the formula Ie

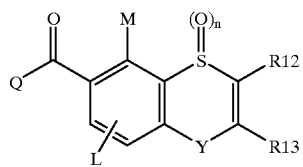

Ie where

L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, n is two;

Y is

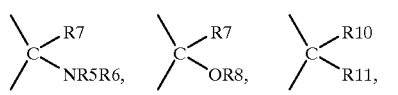

or is oxygen or sulfur;

$R^3$ is hydrogen, —$NR^9R^4$;

$C_1$–$C_6$-alkyl, $C_1$–$C_6$-haloalkyl, $C_1$–$C_6$-alkoxy, $C_1$–$C_6$-haloalkoxy, $C_2$–$C_6$-alkenyl, $C_2$–$C_6$-haloalkenyl, $C_2$–$C_6$-alkynyl;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyloxy, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^4$ is hydrogen, $C_1$–$C_6$-alkyl, $C_1$–$C_6$-haloalkyl, $C_2$–$C_8$-alkenyl, $C_2$–$C_6$-alkynyl, C=O—$NR^{14}$;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^9$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^5$, $R^6$ independently of one another are hydrogen, $C_1$–$C_6$-alkyl, $C_2$–$C_6$-alkenyl, $C_1$–$C_4$-haloalkyl, $C_2$–$C_6$-haloalkenyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^7$ is hydrogen, $C_1$–$C_6$-alkyl, $C_1$–$C_4$-alkoxy, $C_1$–$C_4$-haloalkyl, $C_1$–$C_4$-haloalkoxy;

unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^7$ and $R^{21}$ or $R^7$ and $R^{12}$ can form a bond;

$R^8$ is hydrogen, $C_1$–$C_6$-alkyl, $C_1$–$C_6$-haloalkyl, unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{10}$, $R^{11}$ independently of one another are hydrogen, $C_1$–$C_6$-alkyl;

unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro;

$R^{10}$ and $R^{12}$ or $R^{10}$ and $R^{21}$ can form a bond;

$R^{10}$ and $R^{11}$ together can form a 1,4-dioxabutane-1,4-diyl, 1,3-dioxabutane-1,4-diyl, 1,5-dioxapentane-1,5-diyl, 1,3-dioxapentane-1,5-diyl or 2,4-dioxapentane-1,5-diyl chain which is substituted by hydrogen or $C_1$–$C_4$-alkyl;

$R^{12}$, $R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy;

unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

$R^{14}$ is $C_1$–$C_4$-alkyl;

Q is a pyrazole ring, linked in the 4-position, of the formula II

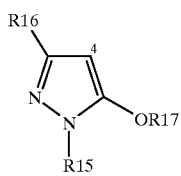

where $R^{15}$ is $C_1$–$C_4$-alkyl, $R^{16}$ is hydrogen, $C_1$–$C_4$-alkyl or $C_1$–$C_4$-haloalkyl and $R^{17}$ is hydrogen, $C_1$–$C_4$-alkylsulfonyl, phenylsulfonyl or alkylphenylsulfonyl, or an agriculturally useful salt thereof.

8. The pyrazol-4-ylbenzoyl compound of the formula I as defined in claim 1 where n is two and Y is

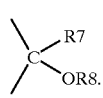

9. A process for the preparation of a compound of the formula I as defined in claim 1, which comprises acylating a pyrazole of the formula IIa

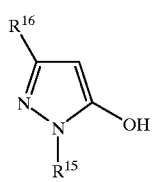

with an acid chloride of the formula IIIa or an acid IIIb

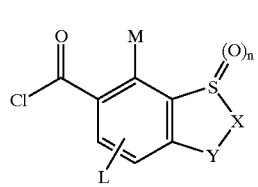

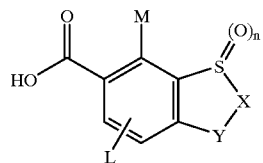

and subjecting the acylation product to a rearrangement reaction in the presence of a catalyst to give the compound I.

10. A herbicidal composition comprising at least one pyrazol-4-ylbenzoyl compound of the formula I as defined in claim 1 and customary inert additives.

11. A method of controlling undesirable vegetation, which comprises treating the plants or their environment with a herbicidally active amount of a pyrazol-4-ylbenzoyl compound of the formula I as defined in claim 1.

12. The pyrazol-4-ylbenzoyl compound of the formula I as defined in claim 1 where X is $CR^{12}R^{13}$ or $CR^{12}=CR^{13}$.

13. The pyrazol-4-ylbenzoyl compound of the formula I as defined in claim 1 wherein Y is

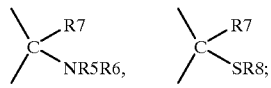

or is oxygen or sulfur.

14. The pyrazol-4-ylbenzoyl compound of the formula I as defined in claim 1 wherein Y is

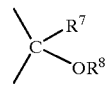

and $R^8$ is $C_1$–$C_4$-haloalkyl, unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro.

15. The pyrazol-4-ylbenzoyl compound of the formula Ia as defined in claim 2 where X is $CR^{12}R^{13}$ or $CR^{12}=CR^{13}$.

16. The pyrazol-4-ylbenzoyl compound of the formula Ib as defined in claim 3 where X is $CR^{12}R^{13}$ or $CR^{12}=CR^{13}$.

17. The pyrazol-4-ylbenzoyl compound of the formula Ic as defined in claim 5 wherein Y is

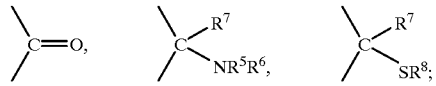

or is oxygen or sulfur.

18. The pyrazol-4-ylbenzoyl compound of the formula Ic as defined in claim 5 wherein Y is

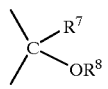

and $R^8$ is $C_1$–$C_4$-haloalkyl, unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;

unsubstituted or substituted benzyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro.

* * * * *

UNITED STATES PATENT AND TRADEMARK OFFICE
CERTIFICATE OF CORRECTION

PATENT NO. : 6,291,682 B1
DATED : September 18, 2001
INVENTOR(S) : Otten et al.

It is certified that error appears in the above-identified patent and that said Letters Patent is hereby corrected as shown below:

Column 75, claim 6,
Line 51, "$C_1$-C4-" should be -- $C_1$-$C_4$- --.

Column 76, claim 6,
Line 3, "$C_1$-$C_6$-haloalkenyl" should be -- $C_2$-$C_6$-haloalkenyl --.

Column 78, claim 7,
Line 13, "$C_2$-$C_8$-" should be -- $C_2$-$C_6$- --.

Column 82, claim 18,
Last line, delete "62".

Signed and Sealed this

Twenty-sixth Day of February, 2002

Attest:

JAMES E. ROGAN
*Attesting Officer*     *Director of the United States Patent and Trademark Office*